(12) United States Patent
Greshock et al.

(10) Patent No.: US 10,519,147 B2
(45) Date of Patent: Dec. 31, 2019

(54) DIAMINO-ALKYLAMINO-LINKED ARYLSULFONAMIDE COMPOUNDS WITH SELECTIVE ACTIVITY IN VOLTAGE-GATED SODIUM CHANNELS

(71) Applicants: Merck Sharp & Dohme Corp., Rahway, NJ (US); Thomas J. Greshock, Collegeville, PA (US); James Mulhearn, Elkins Park, PA (US); Liangqin Guo, Edison, NJ (US); Ting Zhang, Princeton Junction, NJ (US); Deping Wang, Furlong, PA (US); Ronald M. Kim, Summit, NJ (US); Mark E. Layton, Harleysville, PA (US); Michael J. Kelly, III, Paoli, PA (US); Rajan Anand, Fanwood, NJ (US); Philippe Nantermet, Landsdale, PA (US); Tianying Jian, Westfield, NJ (US); Anthony J. Roecker, Harleysville, PA (US); Walter Won, Alpine, NJ (US); Gang Zhou, Bridgewater, NJ (US)

(72) Inventors: Thomas J. Greshock, Collegeville, PA (US); James Mulhearn, Elkins Park, PA (US); Liangqin Guo, Edison, NJ (US); Ting Zhang, Princeton Junction, NJ (US); Deping Wang, Furlong, PA (US); Ronald M. Kim, Summit, NJ (US); Mark E. Layton, Harleysville, PA (US); Michael J. Kelly, III, Paoli, PA (US); Rajan Anand, Fanwood, NJ (US); Philippe Nantermet, Landsdale, PA (US); Tianying Jian, Westfield, NJ (US); Anthony J. Roecker, Harleysville, PA (US); Walter Won, Alpine, NJ (US); Gang Zhou, Bridgewater, NJ (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 16/061,815

(22) PCT Filed: Dec. 15, 2016

(86) PCT No.: PCT/US2016/066765
§ 371 (c)(1),
(2) Date: Jun. 13, 2018

(87) PCT Pub. No.: WO2017/106409
PCT Pub. Date: Jun. 22, 2017

(65) Prior Publication Data
US 2018/0362518 A1 Dec. 20, 2018

Related U.S. Application Data

(60) Provisional application No. 62/422,182, filed on Nov. 15, 2016, provisional application No. 62/417,040, (Continued)

(51) Int. Cl.
*C07D 417/12* (2006.01)
*A61K 45/06* (2006.01)
(Continued)

(52) U.S. Cl.
CPC ............ *C07D 417/12* (2013.01); *A61K 45/06* (2013.01); *A61P 11/14* (2018.01); *A61P 17/04* (2018.01);
(Continued)

(58) Field of Classification Search
CPC .................................................... C07D 417/12
See application file for complete search history.

(56) References Cited

U.S. PATENT DOCUMENTS

2009/0143358 A1  6/2009  Marron et al.
2010/0197655 A1  8/2010  Beaudoin et al.

FOREIGN PATENT DOCUMENTS

WO        2005013914 A2    2/2005
WO    WO2015181797 A1    12/2015
(Continued)

OTHER PUBLICATIONS

PCT Search Report and Written Opinion for PCT/US2016/066765 dated Mar. 2, 2017; 11 pages.

*Primary Examiner* — Andrew D Kosar
*Assistant Examiner* — John S Kenyon
(74) *Attorney, Agent, or Firm* — Patricia A. Shatynski; John C. Todaro

(57) ABSTRACT

Disclosed are compounds of Formula A, or a salt thereof, where Q, X, R1 and R2 are as defined herein, which compounds have properties for inhibiting $Na_v$ 1.7 ion channels found in peripheral and sympathetic neurons. Also described are pharmaceutical formulations comprising the compounds of Formula A or their salts, and methods of treating pain (acute, post-operative, neuropathic), or cough or itch disorders using the same.

A

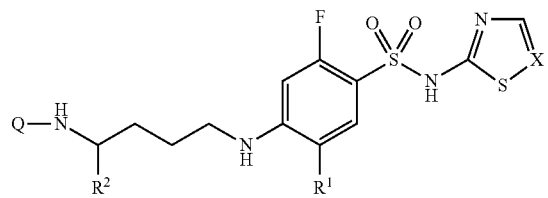

18 Claims, No Drawings

Related U.S. Application Data filed on Nov. 3, 2016, provisional application No. 62/269,648, filed on Dec. 18, 2015.

(51) Int. Cl.
| | | |
|---|---|---|
| *C07D 277/52* | (2006.01) | |
| *C07D 285/135* | (2006.01) | |
| *A61P 25/02* | (2006.01) | |
| *A61P 25/04* | (2006.01) | |
| *A61P 11/14* | (2006.01) | |
| *A61P 17/04* | (2006.01) | |

(52) U.S. Cl.
CPC ............... *A61P 25/02* (2018.01); *A61P 25/04* (2018.01); *C07D 277/52* (2013.01); *C07D 285/135* (2013.01)

(56) References Cited

FOREIGN PATENT DOCUMENTS

| WO | WO2016009303 A1 | 1/2016 | |
|---|---|---|---|
| WO | WO-2017106226 A1 * | 6/2017 | ........... C07D 417/12 |

* cited by examiner

DIAMINO-ALKYLAMINO-LINKED ARYLSULFONAMIDE COMPOUNDS WITH SELECTIVE ACTIVITY IN VOLTAGE-GATED SODIUM CHANNELS

CROSS-REFERENCE TO RELATED APPLICATIONS

This application is a U.S. National Phase application under 35 U.S.C. § 371 of PCT Application No. PCT/US2016/066765, filed Dec. 15, 2016, which claims the priority of each of the following U.S. Provisional Applications: Ser. No. 62/269,648 filed Dec. 18 2015; Ser. No. 62/417,040 filed Nov. 3, 2016; and Ser. No. 62/422,182 filed Nov. 15, 2016, each of which applications are incorporated herein by reference.

BACKGROUND

Voltage-gated sodium channels play a central role in initiating and propagating action potentials in electrically excitable cells such as neurons and muscle, see for example Yu and Catterall, Genome Biology 4:207 (2003) and references therein. Voltage-gated sodium channels are multimeric complexes characterized by an Alpha-subunit which encompasses an ion-conducting aqueous pore, and is the site of the essential features of the channel, and at least one Beta-subunit that modifies the kinetics and voltage-dependence of the channel gating. These structures are ubiquitous in the central and peripheral nervous system where they play a central role in the initiation and propagation of action potentials, and also in skeletal and cardiac muscle where the action potential triggers cellular contraction. (see Goldin, Ann NY Acad Sci. 30; 868:38-50 (1999).

Sensory neurons are also responsible for conveying information from the periphery e.g. skin, muscle and joints to the central nervous system (spinal cord). Sodium channels are integral to this process as sodium channel activity is required for initiation and propagation of action potentials triggered by noxious stimuli (thermal, mechanical and chemical) activating peripheral nociceptors.

Nine different Alpha-subunits have been identified and characterized in mammalian voltage-gated sodium channels. These structures are designated $Na_v$ 1.X sodium channels (X=1 to 9) in accordance with currently accepted nomenclature practice, designating their ion selectivity (Na), the physiological regulator ('v', potential, i.e. voltage), and the gene subfamily encoding them (1.), with the number designator X (1 to 9) being assigned for the alpha subunit present in the structure (see Aoldin et al., Neuron, 28:365-368 (2000)). $Na_v$ 1.7 voltage-gated sodium ion channels (herein designated "Nav 1.7 channels" in some instances for convenience) are expressed primarily in sensory and sympathetic neurons, are believed to play a role in various maladies, for example, nociception, cough, and itch, and in particular have a central role in inflammatory pain perception, (see Wood et al. J. Neurobiol. 61: pp 55-71 (2004), Nassar et al., *Proc. Nat. Acad. Sci.* 101(34): pp 12706-12711 (2004), Klinger et. al., Molecular Pain, 8:69 (2012), see Devigili et. al., Pain, 155(9); pp 1702-7 (2014), Lee et. al., Cell, 157:1-12 (2014), Muroi et. al., Lung, 192:15-20 (2014), Muroi et. al., Am J Physiol Regul Integr Comp Physiol 304:R1017-R1023 (2013)).

Loss of function mutations in NaV1.7 lead to Cogenital Insensitivity to Pain (CIP), where patients exhibit a lack of pain sensation for a variety of noxious stimuli (Goldberg et al., Clinical Genetics, 71(4): 311-319 (2007)). Gain of function mutations in NaV1.7, NaV1.8, and NaV1.9 manifest in a variety of pain syndromes where patients experience pain without an external stimulus (Fischer and Waxman, Annals of the New York Academy of Sciences, 1184: 196-207 (2010), Faber et al., PNAS 109(47): 19444-19449 (2012), Zhang et al., American Journal of Human Genetics, 93(5):957-966 (2013)).

Accordingly, it is believed that identification and administration of agents which interact to block $Na_v$ 1.7 voltage-gated sodium ion channels represents a rational approach which may provide treatment or therapy for disorders involving $Na_v$ 1.7 receptors, for example, but not limited to, acute pain, preoperative pain, perioperative pain, post-operative pain, neuropathic pain, cough, or itch disorders, as well as those stemming specifically from dysfunction of $Na_v$ 1.7 voltage-gated sodium ion channels, see Clare et al., Drug Discovery Today, 5: pp 506-520 (2000)).

It has been shown in human patients as well as in animal models of neuropathic pain that damage to primary afferent sensory neurons can lead to neuroma formation and spontaneous activity, as well as evoked activity in response to normally innocuous stimuli. [Carter, G. T. and Galer, B. S., Advances in the Management of Neuropathic Pain, Physical Medicine and Rehabilitation Clinics of North America, 2001, 12(2): pp 447 to 459]. Injuries of the peripheral nervous system often result in neuropathic pain persisting long after an initial injury resolves. Examples of neuropathic pain include, for example, post herpetic neuralgia, trigeminal neuralgia, diabetic neuropathy, chronic lower back pain, phantom limb pain, pain resulting from cancer and chemotherapy, chronic pelvic pain, complex regional pain syndrome and related neuralgias. The ectopic activity of normally silent sensory neurons is thought to contribute to the generation and maintenance of neuropathic pain, which is generally assumed to be associated with an increase in sodium channel activity in the injured nerve. [Baker, M. D. and Wood, J. N., Involvement of Na Channels in Pain Pathways, TRENDS is Pharmacological Sciences, 2001, 22(1): pp 27 to 31].

Nociception is essential for survival and often serves a protective function. However, the pain associated with surgical procedures and current therapies to relieve that pain, can delay recovery after surgery and increase the length of hospital stays. As many as 80% of surgical patients experience post-operative pain, which arises as a result of tissue damage, including damage to peripheral nerves and subsequent inflammation). Furthermore, 10-50% of surgical patients will develop chronic pain after surgery often because the nerve damage results in lasting neuropathic pain once the wound has healed (Meissner et al., Current Medical Research and Opinion, 31(11):2131-2143 (2015)).

Cough is one of the most prevalent symptoms for which patients seek the attention of their primary care physicians; chronic cough for example is estimated to affect approximately 40% of the population. The fundamental mechanisms of the cough reflex are complex and involve an array of events initiated by the activation of airway sensory nerves that physically results in a forced expiration of the airways. This protective reflex is necessary to remove foreign material and secretions from the airways, however, chronic, non-protective cough results in a dramatic negative impact on quality of life (see Nasra et. al., Pharmacology & Therapeutics, 124(3):354-375 (2009)).

Cough symptoms can arise from the common cold, allergic and vasomotor rhinitis, acute and chronic bacterial sinusitis, exacerbation of chronic obstructive pulmonary disease, *Bordetella pertussis* infection, asthma, postnasaldrip syndromes, gastroesophageal reflux disease, eosinophilic and chronic bronchitis, and angiotensin-converting-enzyme inhibitors, cough is categorically described as acute, subacute, or chronic, respectively lasting less than three weeks, three to eight weeks, and more than eight weeks in duration (see Irwin et. al., The New England Journal of Medicine, 343(23):1715-1721 (2000)).

Current standard of care for the treatment of cough consists of centrally and peripherally acting suppressants such as opioids and local anesthetics respectively, both of which are dose-limited by side-effects (see Cox et. al., Best Practice & Research Clinical Anaesthesiology, 117(1):111-136 (2003) and Benyamin et. al., Pain Physician, 11:S105-S120 (2008)). Opioids primarily act on µ-opioid receptors of the central nervous system, and in some reports, also on peripheral afferents of the cough reflex arc—they exhibit varied degrees of efficacy and are limited by side-effects such as sedation, physical dependence, and gastrointestinal problems; morphine has shown to be an effective treatment for chronic cough (see Morice et. al., Am J Respir Crit Care Med 175:312-315 (2007) and Takahama et. al., Cough 3:8 (2007)), but is generally restricted to patients with terminal illness such as lung cancer. Codeine, found in some cough syrups, and also administered systemically, was found no more effective than placebo (see Smith et. al., Journal of Allergy and Clinical Immunology, 117:831-835 (2006). Local anesthetics act peripherally by reducing the generation of action potentials in sensory nerves of the airway as a result of non-selectively inhibiting all voltage gated sodium channel subtypes and have demonstrated varied degrees of efficacy in treating cough. These compounds are often found in over-the-counter lozenges and have been shown to relieve cough when administered via nebulisation (see Nasra et. al., Pharmacology & Therapeutics, 124(3):354-375 (2009) and Hansson et. al., Thorax, 49(11):1166-1168 (1994)). However, in a study with chronic obstructive pulmonary disease patients, lidocaine was not effective (see Chong et. al., Emerg Med J, 22(6):429-32 (2005)).

In pre-clinical animals, $Na_v$ 1.7, $Na_v$ 1.8 Nav1.8, and NaV1.9 were determined to be the primary voltage-gated sodium channels expressed in the afferent nerves of the respiratory tract (see Muroi et. al., Lung, 192:15-20 (2014)) and in animal models of cough, suppression of NaV1.7 function resulted in a marked decrease in number of coughs (see Muroi et. al., Am J Physiol Regul integr Comp Physiol, 304:R1017-R0123 (2013)), thus, combined with previous evidence that local anesthetics can be effective antitussive agents, the targeted blockade of NaV1.7 channels is believed to represent a rational approach for the treatment of cough with a preferential side-effect profile as compared to local anesthetics. Local anesthetics undesirably inhibit all voltage gated sodium channels, such as NaV1.5 channels which are found in heart muscle (see Rook et. al., Cardiovascular Research 93:12-23 (2012)).

Pruritus, also commonly known as itch, affects approximately 4% of the global population (see Flaxman et. al., Lancet, 380:2163-2196 (2012)) is "an unpleasant sensation that elicits the desire or reflex to scratch" and is regarded as closely related to pain. Theories on the origin of itch implicate the subtle, low-frequency activation of nociceptors (pain-sensing neurons), however, it has been described that some afferents preferentially respond to histamine, which induces itch (see Schmelz et. al., J Neuroscience, 17(20): 8003-8008 (1997)). At the same time, it has been found that histamine-responding neurons also respond to capsaicin which produces pain (see McMahon et. al., Trends. Neurosci., 15:497-501 (1992)). Members of the transient receptor potential (TRP) family, and nerve growth factor (NGF) are both known to play a role in itch and pain, and clinically, both maladies are treated with therapeutic agents such as gabapentin and antidepressants—as such, it continues to be accepted that the underlying mechanisms of pain and itch are highly interwoven and complex, and distinguishing pan-selective or itch-selective pathways remains ambiguous (see Ikoma et. al., Nature Reviews Neuroscience, 7:535-547 (2006)).

Itch, both chronic and acute, can arise from many different insults and diseases and may be classified as dermal or pruriceptive, neurogenic, neuropathic, or psychogenic: itch can arise from both systemic disorders, skin disorders, as well as physical or chemical insult to the dermis. Pathologically, conditions such as dry skin, eczema, psoriasis, varicella zoster, urticaria, scabies, renal failure, cirrhosis, lymphoma, iron deficiency, diabetes, menopause, polycythemia, uremia, and hyperthyroidism can cause itch, as can diseases of the nervous system such as tumors, multiple sclerosis, peripheral neuropathy, nerve compression, and delusions related to obsessive-compulsive disorders. In skin, pruritogens are released from keratinocytes, lymphocytes, mast cells, and eosinophils during inflammation. These molecules act directly on free nerve endings to induce itch; medicines such as opioids and chloroquine can also trigger itch (see Ikoma et. al., Nature Reviews Neuroscience, 7:535-547 (2006)). Itching following burn is also an extremely serious clinical problem as it hampers the healing process, results in permanent scaring, and negatively impacts quality of life (see Loey et. al., British Journal of Dermatology, 158:95-100 (2008)).

Gain of function mutations of NaV1.7 have been found in approximately 28% of patients with idiopathic small fiber neuropathy (I-SFN); these mutations were found to render dorsal root ganglia neurons hyperexcitable, reducing the threshold of activation and increasing the frequency of evoked firing (see Waxman et. al., Neurology, 78(21):1635-1643 (2012)). Severe, uncontrollable itch has also been genetically linked to a gain-of-function mutation (I739V) in the sodium channel NaV1.7 in man (see Devigili et. al., Pain, 155(9); pp 1702-7 (2014)). Additionally, the sea-anemone toxin ATX-II has been found to elicit pain and itch in human volunteers after intradermal injection on the forearm; electrophysiology studies revealed that ATX-II enhanced NaV1.7 and NaV1.6 resurgent currents (see Klinger et. al., Molecular Pain, 8:69 (2012)). It has been demonstrated in animal models that selective blockade of NaV1.7 channels can effectively suppress both inflammatory and neuropathic pain, as well as acute and chronic itch, thus blockade of NaV1.7 channels is believed to represent a rational approach to treatment of pain and itch disorders (see Lee et. al., Cell, 157:1-12 (2014)).

Because voltage gated sodium ion channels are ubiquitous in the central and peripheral nervous system, as well as in both cardiac and skeletal muscle, and conservation of structures in the various Alpha-subunits characterizing voltage-gated sodium ion channels implicates the potential for producing serious side effects when utilizing therapeutic agents having a mechanism of action that target inhibition of voltage-gated sodium ion channels, for example, therapeutic agents suitable for use in addressing nociception, cough, or itch disorders, requires therapeutic agents having specificity in their action, for example, discriminating between action upon $Na_v$ 1.5 sodium ion channels, thought to be important in regulation of cardiac function and action upon $Na_v$ 1.7 sodium ion channels, thought to be central in inflammatory nociception, cough, or itch and disorders arising from dysfunctional Na$_v$ 1.7 sodium ion channels.

There remains a need for additional compounds having high potency for inhibiting Na$_v$ 1.7 sodium ion channels and selective activity for Na$_v$ 1.7 sodium ion channels providing structural variety to facilitate rational development of therapeutic agents for use as a selective Nav 1.7 sodium ion channel inhibitor.

SUMMARY OF THE INVENTION

In one aspect, the invention provides compounds having selective activity as Na$_v$ 1.7 sodium ion channel inhibitors which have the structure of Formula A, or a salt thereof:

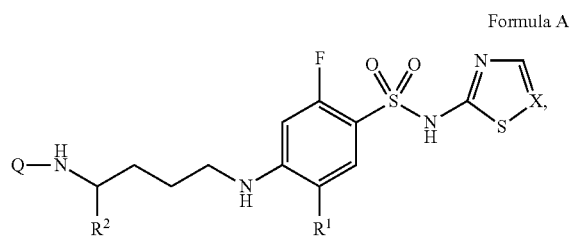

Formula A wherein:
R$^1$ is —Cl, —Br, or —F;
R$^2$ is —H or —CH$_3$;
X is:
—N═; or
—C(R$^3$)═, wherein R$^3$ is: (i) —H; (ii) —Cl; or (iii) —F; and
Q is:
(a) a moiety of the formula:

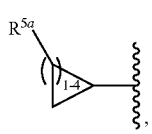

wherein one of R$^{5a}$ is NH$_2$ and the others are —H; or
(b) a moiety of the formula:

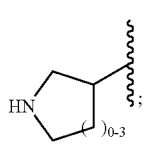

(c) a moiety of the formula:

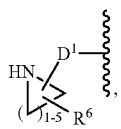

wherein
D$^1$ is a linear- or branched-alkyl, or a geminal-cycloalkyl moiety of up to 6 carbon atoms; and
R$^6$ is optionally present as a single substituent and is linear or branched alkyl of up to 4 carbon atoms,
which is optionally substituted on one or more carbon atoms thereof with one or more —F, and in some embodiments when present is preferably —CF$_3$; or
(d) R$^4$—NH-D$^2$-, wherein R$^4$ is H, lower alkyl, or lower cycloalkyl and D$^2$ is a linear alkyl of at least two up to 6 carbon atoms, a branched-alkyl of up to 6 carbon atoms, or a geminal-cycloalkyl moiety of up to 8 carbon atoms.

In some embodiments, it is preferred to select X in a compound of Formula A to be —CH═.

In some embodiments, it is preferred to select X in a compound of Formula A to be —C(Cl)═.

In some embodiments, it is preferred to select X in a compound of Formula A to be —C(F)═.

In some embodiments, it is preferred to select X in a compound of Formula A to be —N═.

In some embodiments, it is preferred to select R$^1$ to be —Cl.

In some embodiments, it is preferred to select R$^1$ to be —Br.

In some embodiments, it is preferred to select R$^1$ to be —F.

In some embodiments it is preferred to select R$^2$ to be —H.

In some embodiments it is preferred for Q in the compound of Formula A to be a moiety of the Formula R$^4$—NH-D$^2$-, wherein R$^4$ is: —H or a linear, branched, or cyclic alkyl of up to 6 carbon atoms and D$^2$ is a linear- or branched-alkyl of up to 6 carbon atoms or a geminalcycloalkyl of up to 6 carbon atoms.

In some embodiments, where Q is selected to be a moiety of the Formula:

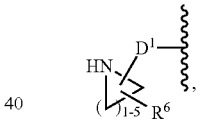

it is preferred to select D$^1$ to be a geminalcycloalkyl, of the formula:

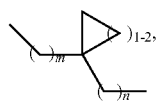

wherein m and n are 0 or 1 and m+n is at least 1.

In some embodiments it is preferred for the inventive compound to be:
5-chloro-2-fluoro-4-[(4-{[(2S)-piperidin-2-ylmethyl]amino}butyl)amino]-N-1,3-thiazol-2-ylbenzenesulfonamide;
5-chloro-2-fluoro-4-[(4-{[(2R)-piperidin-2-ylmethyl]amino}butyl)amino]-N-1,3-thiazol-2-ylbenzenesulfonamide;
5-chloro-2-fluoro-4-[(4-{[(2S)-pyrrolidin-2-ylmethyl]amino}butyl)amino]-N-1,3-thiazol-2-ylbenzenesulfonamide;
4-[(4-{[(1S,2S)-2-aminocyclohexyl]amino}butyl)amino]-5-chloro-2-fluoro-N-1,3-thiazol-2-ylbenzenesulfonamide;
4-({4-[(2-amino-1,1-dimethylethyl)amino]butyl}amino)-5-chloro-2-fluoro-N-1,3-thiazol-2-ylbenzenesulfonamide;

4-({4-[(2-aminoethyl)(methyl)amino]butyl}amino)-5-chloro-2-fluoro-N-1,3-thiazol-2-ylbenzenesulfonamide;
5-chloro-2-fluoro-4-{[4-({(1S)-1-[(2S)-pyrrolidin-2-yl]ethyl}amino)butyl]amino}-N-1,3-thiazol-2-ylbenzenesulfonamide;
4-[(4-{[(1R,2R)-2-aminocyclohexyl]amino}butyl)amino]-5-chloro-2-fluoro-N-1,3-thiazol-2-ylbenzenesulfonamide;
4-[(4-{[(1S,2R)-2-aminocyclopentyl]amino}butyl)amino]-5-chloro-2-fluoro-N-1,3-thiazol-2-ylbenzenesulfonamide;
4-[(4-{[(1R,2S)-2-aminocyclohexyl]amino}butyl)amino]-5-chloro-2-fluoro-N-1,3-thiazol-2-ylbenzenesulfonamide;
4-({4-[(2-aminoethyl)amino]butyl}amino)-5-chloro-2-fluoro-N-1,3-thiazol-2-ylbenzenesulfonamide;
5-chloro-2-fluoro-4-({4-[(3R)-pyrrolidin-3-ylamino]butyl}amino)-N-1,3-thiazol-2-ylbenzenesulfonamide;
5-chloro-2-fluoro-4-({4-[(3S)-pyrrolidin-3-ylamino]butyl}-amino)-N-1,3-thiazol-2-ylbenzenesulfonamide;
$N^1$-(2-chloro-5-fluoro-4-((thiazol-2-ylmethyl)sulfonyl)phenyl)-$N^4$—((S)-pyrrolidin-2-ylmethyl)pentane-1,4-diamine;
(R) $N^1$-(2-chloro-5-fluoro-4-((thiazol-2-ylmethyl)sulfonyl)phenyl)-$N^4$—((S)-pyrrolidin-2-ylmethyl)pentane-1,4-diamine;
(S) $N^1$-(2-chloro-5-fluoro-4-((thiazol-2-ylmethyl)sulfonyl)phenyl)-$N^4$—((S)-pyrrolidin-2-ylmethyl)pentane-1,4-diamine;
4-((4-((azetidin-3-ylmethyl)amino)butyl)amino)-5-chloro-2-fluoro-N-(thiazol-2-yl)benzenesulfonamide;
5-chloro-2-fluoro-4-[(4-{[2-(methylamino)ethyl]amino}butyl)amino]-N-1,3-thiazol-2-ylbenzenesulfonamide;
(R)-5-chloro-2-fluoro-4-((4-((pyrrolidin-2-ylmethyl)amino)butyl)amino)-N-(thiazol-2-yl)benzenesulfonamide;
2,5-difluoro-4-[(4-{[(2S)-pyrrolidin-2-ylmethyl]amino}butyl)amino]-N-1,2,4-thiadiazol-5-ylbenzenesulfonamide;
5-chloro-2-fluoro-4-[(4-{[(2S)-pyrrolidin-2-ylmethyl]amino}butyl)amino]-N-1,2,4-thiadiazol-5-ylbenzenesulfonamide;
5-chloro-N-(5-chloro-1,3-thiazol-2-yl)-2-fluoro-4-[(4-{[(2S)-pyrrolidin-2-ylmethyl]amino}butyl)amino]benzenesulfonamide;
5-bromo-2-fluoro-4-[(4-{[(2S)-pyrrolidin-2-ylmethyl]amino}butyl)amino]-N-1,3-thiazol-2-ylbenzenesulfonamide;
5-chloro-2-fluoro-N-(5-fluoro-1,3-thiazol-2-yl)-4-[(4-{[(2S)-pyrrolidin-2-ylmethyl]amino}butyl)amino]benzenesulfonamide;
5-chloro-2-fluoro-4-{[4-({[(2S,4S)-4-methylpyrrolidin-2-yl]methyl}amino)butyl]amino}-N-1,3-thiazol-2-ylbenzenesulfonamide;
5-chloro-2-fluoro-4-{[4-({[(2S,5S)-5-methylpyrrolidin-2-yl]methyl}amino)butyl]amino}-N-1,3-thiazol-2-ylbenzenesulfonamide;
5-chloro-2-fluoro-N-1,3-thiazol-2-yl-4-{[4-({[(2S,4S)-4-(trifluoromethyl)pyrrolidin-2-yl]methyl}amino)butyl]amino}benzenesulfonamide;
4-[(4-{[(1R,2R)-2-aminocyclo-pentyl]amino}butyl)amino]-5-chloro-2-fluoro-N-1,2,4-thiadiazol-5-yl-benzenesulfonamide;
4-[(4-{[(2R)-azetidin-2-ylmethyl-amino}butyl)amino]-5-chloro-2-fluoro-N-1,2,4-thiadiazol-5-yl-benzene-sulfonamide;
4-[(4-{[(2S)-azetidin-2-ylmethyl-amino}butyl)amino]-5-chloro-2-fluoro-N-1,2,4-thiadiazol-5-ylbenzene-sulfonamide;
4-[(4-{[(2S)-2-aminopropyl]amino}butyl)amino]-5-chloro-2-fluoro-N-1,2,4-thiadiazol-5-ylbenzenesulfonamide;
4-{[4-(azetidin-3-ylamino)butyl]-amino}-5-chloro-2-fluoro-N-1,2,4-thiadiazol-5-ylbenzenesulfonamide;
5-bromo-2-fluoro-N-(5-fluoro-1,3-thiazol-2-yl)-4-[(4-{[(2R)-piperidin-2-ylmethyl]amino}butyl)amino]benzene-sulfonamide;
4-[(4-{[(1R,2R)-2-aminocyclopentyl]-amino}butyl)amino]-5-chloro-2-fluoro-N-(5-fluoro-1,3-thiazol-2-yl)benzenesulfonamide;
4-[(4-1{[2R)-2-aminopropyl]amino}-butyl)amino]-5-chloro-2-fluoro-N-(5-fluoro-1,3-thiazol-2-yl)benzene-sulfonamide;
4-[(4-{[(1R)-2-amino-1-methylethyl]-amino}butyl)amino]-5-chloro-2-fluoro-N-1,3-thiazol-2-ylbenzenesulfonamide;
4-[(4-{[(1R,2R)-2-aminocyclopentyl]amino}butyl)amino]-5-chloro-2-fluoro-N-1,3-thiazol-2-ylbenzenesulfonamide;
4-[(4-{[(2S)-2-aminopropyl]-amino}butyl)amino]-5-chloro-2-fluoro-N-1,3-thiazol-2-ylbenzenesulfonamide;
5-chloro-2-fluoro-N-(5-fluoro-1,3-thiazol-2-yl)-4-[(4-{[(2R)-pyrrolidin-2-yl-methyl]amino}-butyl)-amino]benzenesulfonamide;
5-chloro-2-fluoro-4-{[4-({2-[(2R)-pyrrolidin-2-yl]ethyl}-amino)-butyl]-amino}-N-1,3-thiazol-2-yl-benzenesulfonamide;
5-chloro-2-fluoro-4-[(4-{[(2R)-piperidin-2-yl-methyl]amino}butyl)-amino]-N-1,2,4-thiadiazol-5-yl-benzenesulfonamide;
5-chloro-2-fluoro-N-(5-fluoro-1,3-thiazol-2-yl)-4-[(4-{[(2R)-piperidin-2-yl-methyl]amino}butyl)-amino]benzenesulfonamide;
5-chloro-2-fluoro-4-[(4-{[(2R)-pyrrolidin-2-yl-methyl]amino}butyl)amino]-N-1,2,4-thiadiazol-5-yl-benzenesulfonamide;
5-chloro-2-fluoro-N-(5-fluoro-1,3-thiazol-2-yl)-4-{[4-({2-[(2R)-pyrrolidin-2yl]-ethyl}amino)butyl]-amino}benzenesulfonamide;
5-chloro-2-fluoro-4-({4-[(3R)-pyrrolidin-3-ylamino]-butyl}amino)-N-1,2,4-thiadiazol-5-ylbenzene-sulfonamide;
5-chloro-2-fluoro-4-{[4-({2-[(2R)-pyrrolidin-2-yl]ethyl}-amino)butyl]amino}-N-1,2,4-thiadiazol-5-ylbenzene-sulfonamide;
5-chloro-2-fluoro-4-{[4-({2-[(2S)-pyrrolidin-2-yl]ethyl}-amino)butyl]amino}-N-1,2,4-thiadiazol-5-ylbenzene-sulfonamide;
4-{[4-(azetidin-3-ylamino)-butyl]amino}-5-chloro-2-fluoro-N-(5-fluoro-1,3-thiazol-2-yl)benzene-sulfonamide;
5-chloro-2-fluoro-N-(5-fluoro-1,3-thiazol-2-yl)-4-{[4-({2-[(2S)-pyrrolidin-2-yl]ethyl}amino)butyl]amino}benzenesulfonamide;
4-[(4-{[(1R)-3-amino-1-methylpropyl]amino}butyl)amino]-5-chloro-2-fluoro-N-(5-fluoro-1,3-thiazol-2-yl)-benzenesulfonamide;
4-[(4-{[(1R)-3-amino-1-methylpropyl]amino}butyl)amino]-5-chloro-2-fluoro-N-1,3-thiazol-2-ylbenzene-sulfonamide;
4-({4-[(3-amino-1,1-dimethylpropyl)amino]butyl}amino)-5-chloro-2-fluoro-N-(5-fluoro-1,3-thiazol-2-yl)-benzenesulfonamide;

5-chloro-2-fluoro-N-(5-fluoro-1,3-thiazol-2-yl)-4-[(4-{[3-(methylamino)-propyl]amino}butyl)amino]-benzenesulfonamide;
4-[(4-{[(1R)-3-amino-1-methylpropyl]amino}butyl)-amino]-5-chloro-2-fluoro-N-1,2,4-thiadiazol-5-yl-benzenesulfonamide;
4-[(4-{[(3R)-3-amino-butyl]amino}butyl)amino]-5-chloro-2-fluoro-N-(5-fluoro-1,3-thiazol-2-yl)benzene-sulfonamide;
4-({4-[(3-aminopropyl)-amino]butyl}amino)-5-chloro-2-fluoro-N-1,2,4-thiadiazol-5-ylbenzene-sulfonamide;
4-({4-[(2-aminoethyl)-amino]butyl}amino)-5-chloro-2-fluoro-N-1,2,4-thiadiazol-5-ylbenzene-sulfonamide;
4-[(4-{[(3R)-3-aminobutyl]-amino}butyl)amino]-5-chloro-2-fluoro-N-1,3-thiazol-2-ylbenzene-sulfonamide;
4-({4-[(3-aminopropyl)amino]-butyl}amino)-5-chloro-2-fluoro-N-(5-fluoro-1,3-thiazol-2-yl)benzene-sulfonamide;
5-bromo-2-fluoro-N-(5-fluoro-1,3-thiazol-2-yl)-4-({4-[(3R)-pyrrolidin-3-yl-amino]butyl}amino)benzene-sulfonamide;
5-bromo-2-fluoro-4-({4-[(3R)-pyrrolidin-3-ylamino]-butyl}amino)-N-1,3-thiazol-2-ylbenzenesulfonamide;
4-{[4-(azepan-3-ylamino)-butyl]amino}-5-chloro-2-fluoro-N-1,2,4-thiadiazol-5-yl-benzenesulfonamide;
5-chloro-2-fluoro-4-[(4-{[2-(methylamino)ethyl]amino}-butyl)amino]-N-1,2,4-thiadiazol-5-ylbenzene-sulfonamide;
5-chloro-N-(5-chloro-1,3-thiazol-2-yl)-2-fluoro-4-[(4-{[2-(methylamino)ethyl]-amino}butyl)amino]benzene-sulfonamide;
5-bromo-2-fluoro-4-[(4-{[2-(methylamino)ethyl]amino}-butyl)amino]-N-1,3-thiazol-2-ylbenzenesulfonamide;
5-bromo-2-fluoro-4-[(4-{[3-(methylamino)propyl]amino}butyl)amino]-N-1,3-thiazol-2-ylbenzenesulfonamide;
5-bromo-2-fluoro-N-(5-fluoro-1,3-thiazol-2-yl)-4-[(4-{[3-(methylamino)-propyl]amino}butyl)amino]-benzenesulfonamide;
4-({4-[(2-aminoethyl)-amino]butyl}amino)-5-chloro-2-fluoro-N-(5-fluoro-1,3-thiazol-2-yl)benzene-sulfonamide;
5-chloro-2-fluoro-4-{[4-({3-[(2-fluoroethyl)amino]-propyl}amino)butyl]amino}-N-1,2,4-thiadiazol-5-yl-benzenesulfonamide;
4-[(4-{[(1R)-2-amino-1-methylethyl]amino}butyl)-amino]-5-chloro-2-fluoro-N-(5-fluoro-1,3-thiazol-2-yl)-benzenesulfonamide;
4-[(4-{[(1R)-2-amino-1-methylethyl]amino}butyl)-amino]-5-chloro-2-fluoro-N-1,2,4-thiadiazol-5-yl-benzenesulfonamide;
4-({4-[(2-amino-1,1-dimethylethyl)amino]butyl}amino)-5-chloro-2-fluoro-N-(5-fluoro-1,3-thiazol-2-yl)benzenesulfonamide;
4-[(4-{[1-(aminomethyl)cyclobutyl]amino}butyl)amino]-5-chloro-2-fluoro-N-(5-fluoro-1,3-thiazol-2-yl)benzenesulfonamide;
4-[(4-{[(1-aminocyclopropyl)methyl]amino}butyl)amino]-5-chloro-2-fluoro-N-(5-fluoro-1,3-thiazol-2-yl)benzenesulfonamide;
4-[(4-{[(1R,2S)-2-aminocyclopentyl]amino}butyl)amino]-5-chloro-2-fluoro-N-(5-fluoro-1,3-thiazol-2-yl)benzenesulfonamide;
5-chloro-2-fluoro-N-(5-fluoro-1,3-thiazol-2-yl)-4-[(4-{[(2R)-2-(methylamino)propyl]-amino}butyl)amino]benzenesulfonamide;
4-[(4-{[(1 S)-2-amino-1-methylethyl]amino}butyl)amino]-5-chloro-2-fluoro-N-(5-fluoro-1,3-thiazol-2-yl)benzenesulfonamide;
4-[(4-{[(1S)-2-amino-1-methylethyl]amino}butyl)amino]-5-chloro-2-fluoro-N-1,2,4-thiadiazol-5-ylbenzenesulfonamide;
4-[(4-{[(1S)-2-amino-1-methylethyl]amino}butyl)amino]-5-chloro-2-fluoro-N-1,3-thiazol-2-ylbenzenesulfonamide;
4-[(4-{[(1-aminocyclobutyl)methyl]amino}butyl)amino]-5-chloro-2-fluoro-N-(5-fluoro-1,3-thiazol-2-ylbenzenesulfonamide;
4-[(4-{[(1S,2S)-2-aminocyclopentyl]amino}butyl)amino]-5-chloro-2-fluoro-N-1,2,4-thiadiazol-5-ylbenzenesulfonamide;
4-[(4-{[(1S,2S)-2-aminocyclopentyl]amino}butyl)amino]-5-chloro-2-fluoro-N-(5-fluoro-1,3-thiazol-2-yl)benzenesulfonamide;
4-[(4-{[(1S,2S)-2-aminocyclopentyl]amino}butyl)amino]-5-chloro-2-fluoro-N-1,3-thiazol-2-ylbenzenesulfonamide;
4-[(4-{[(2R)-azetidin-2-ylmethyl]amino}butyl)amino]-5-chloro-2-fluoro-N-(5-fluoro-1,3-thiazol-2-yl)benzenesulfonamide;
4-[(4-{[(2S)-azetidin-2-ylmethyl]amino}butyl)amino]-5-chloro-2-fluoro-N-1,3-thiazol-2-ylbenzenesulfonamide;
4-[(4-{[(2R)-azetidin-2-ylmethyl]amino}butyl)amino]-5-chloro-2-fluoro-N-1,3-thiazol-2-ylbenzenesulfonamide;
4-[(4-{[(2S)-azetidin-2-ylmethyl]amino}butyl)amino]-5-bromo-2-fluoro-N-1,2,4-thiadiazol-5-ylbenzenesulfonamide;
4-[(4-{[(2R)-azetidin-2-ylmethyl]amino}butyl)amino]-5-bromo-2-fluoro-N-1,2,4-thiadiazol-5-ylbenzenesulfonamide;
4-[4-[[(1R)-3-amino-1-methyl-propyl]amino]butylamino]-5-bromo-2-fluoro-N-(1,2,4-thiadiazol-5-yl)benzenesulfonamide;
4-[4-[[(2S)-2-aminopropyl]amino]butylamino]-5-bromo-2-fluoro-N-(1,2,4-thiadiazol-5-yl)benzenesulfonamide;
4-[4-[(2-aminocyclobutyl)amino]butylamino]-5-chloro-2-fluoro-N-(1,2,4-thiadiazol-5-yl)benzenesulfonamide;
4-((4-(((1R,2R)-2-aminocyclobutyl)amino)butyl)amino)-5-chloro-2-fluoro-N-(1,2,4-thiadiazol-5-yl)benzenesulfonamide;
4-((4-(((1S,2S)-2-aminocyclobutyl)amino)butyl)amino)-5-chloro-2-fluoro-N-(1,2,4-thiadiazol-5-yl)benzenesulfonamide;
4-((4-(((S)-2-((R)-1-aminoethyl)-4-methylpentyl)amino)butyl)amino)-5-chloro-2-fluoro-N-(5-fluorothiazol-2-yl)benzenesulfonamide;
4-((4-(((S)-2-((R)-1-aminoethyl)-4-methylpentyl)amino)butyl)amino)-5-chloro-2-fluoro-N-(1,2,4-thiadiazol-5-yl)benzenesulfonamide;
4-[4-[[(1R,2R)-2-aminocyclopentyl]amino]butylamino]-2,5-difluoro-N-(1,2,4-thiadiazol-5-yl)benzenesulfonamide;
4-[4-(2-aminoethylamino)butylamino]-5-bromo-2-fluoro-N-(1,2,4-thiadiazol-5-yl)benzenesulfonamide;
4-[4-[(1-aminocyclopropyl)methylamino]butylamino]-5-bromo-2-fluoro-N-(1,2,4-thiadiazol-5-yl)benzenesulfonamide;
5-bromo-2-fluoro-4-[4-[2-(methylamino)ethylamino]butylamino]-N-(1,2,4-thiadiazol-5-yl)benzenesulfonamide;
5-bromo-2-fluoro-4-[4-[3-(methylamino)propylamino]butylamino]-N-(1,2,4-thiadiazol-5-yl)benzenesulfonamide;
5-bromo-4-[4-[2-(ethylamino)ethylamino]butylamino]-2-fluoro-N-(1,2,4-thiadiazol-5-yl)benzenesulfonamide;

4-[4-[[(1S,2R)-2-aminocyclopentyl]amino]butylamino]-5-bromo-2-fluoro-N-(1,2,4-thiadiazol-5-yl)benzenesulfonamide;

4-[4-[[(1R,2R)-2-aminocyclopentyl]amino]butylamino]-5-bromo-2-fluoro-N-(1,2,4-thiadiazol-5-yl)benzenesulfonamide;

4-[4-[[(1S,3S)-3-aminocyclopentyl]amino]butylamino]-5-bromo-2-fluoro-N-(1,2,4-thiadiazol-5-yl)benzenesulfonamide;

5-bromo-2-fluoro-4-[4-[(3-methylpyrrolidin-3-yl)amino]butylamino]-N-(1,2,4-thiadiazol-5-yl)benzenesulfonamide;

4-[4-(3-aminopropylamino)butylamino]-5-bromo-2-fluoro-N-(1,2,4-thiadiazol-5-yl)benzenesulfonamide;

4-[4-[[1-(aminomethyl)cyclopropyl]amino]butylamino]-5-bromo-2-fluoro-N-(1,2,4-thiadiazol-5-yl)benzenesulfonamide;

4-[4-[[(2R)-2-aminopropyl]amino]butylamino]-5-bromo-2-fluoro-N-(1,2,4-thiadiazol-5-yl)benzenesulfonamide;

(S)-5-bromo-2-fluoro-4-((4-(pyrrolidin-3-ylamino)butyl)amino)-N-(1,2,4-thiadiazol-5-yl)benzenesulfonamide; or 4-[(4-{[(1R)-2-amino-1-methylethyl]amino}butyl)amino]-5-bromo-2-fluoro-N-1,2,4-thiadiazol-5-ylbenzenesulfonamide, or a pharmaceutically acceptable salt of any thereof.

In one aspect the invention provides a pharmaceutical composition comprising at least one compound of Formula A, or a salt thereof, and at least one pharmaceutically acceptable excipient adapted for administration to a patient via any pharmaceutically acceptable route, including dosage forms for oral, intravenous, infusion, subcutaneous, transcutaneous, intramuscular, intradermal, transmucosal, or intramucosal routes of administration.

In one aspect this invention provides also a pharmaceutical composition comprising a pharmaceutical carrier, an effective amount of at least one compound of Formula A, or a salt thereof, an effective amount of at least one other pharmaceutically active ingredient which is: (i) an opioid agonist or antagonist; (ii) a calcium channel antagonist; (iii) an NMDA receptor agonist or antagonist; (iv) a COX-2 selective inhibitor; (v) an NSAID (non-steroidal anti-inflammatory drug); or (vi) paracetamol (APAP, acetaminophen), and a pharmaceutically acceptable carrier.

In one aspect the invention provides also a method of treatment, management, alleviation or amelioration of conditions or disease states which can be treated, managed, alleviated or ameliorated by specific inhibiting of Nav 1.7 channel activity, the method comprising administering to a patient in need thereof a composition comprising at least one compound of Formula A, or a salt thereof, in an amount providing a serum level of at least one said compound sufficient to effect said treatment, management, alleviation or amelioration of said conditions or disease states. Preferably the condition or disease state to be treated, managed, alleviated or ameliorated include itch, cough, or pain, for example, acute pain or a chronic pain disorder. In some embodiments, the condition is preferably pain, more preferably, chronic pain or acute pain.

DETAILED DESCRIPTION OF THE INVENTION

As mentioned above, the invention provides compounds believed to have selective activity as $Na_v$ 1.7 sodium ion channel inhibitors which have the structure of Formula A, or a salt thereof:

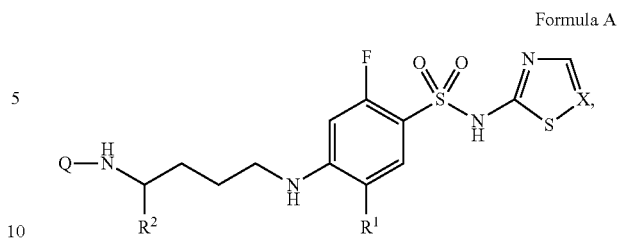

Formula A wherein Q, X, $R^1$ and $R^2$ are defined herein above.

Preferred compounds of the invention exhibit a potency ($IC_{50}$) of less than about 500 nanomolar when assayed in accordance with IonWorks® assay technique described herein, and exhibit at least 50-fold selectivity for $Na_v$ 1.7 sodium channels over $Na_v$ 1.5 sodium channels, more preferably at least 500-fold selectivity for $Na_v$ 1.7 sodium channels over $Na_v$ 1.5 sodium channels when functional potency for each channel are compared using the IonWorks® assay technique described herein.

Compounds of the invention and formulations comprising compounds of the invention are believed to be useful in providing treatment, management, alleviation or amelioration of conditions or disease states which can be treated, managed, alleviated or ameliorated by specific inhibiting of Nav 1.7 channel activity. Examples of disease states which are believed to be desirably affected using such therapy include, but are not limited to, inhibiting acute pain, perioperative, post-operative and neuropathic pain, for example, postherpetic neuralgia, trigeminal neuralgia, diabetic neuropathy, chronic lower back pain, phantom limb pain, pain resulting from cancer and chemotherapy, chronic pelvic pain, complex regional pain syndrome and related neuralgias, pruritus or cough.

As described herein, unless otherwise indicated, the use of a compound in treatment means that an amount of the compound, generally presented as a component of a formulation that comprises other excipients, is administered in aliquots of an amount, and at time intervals, which provides and maintains at least a therapeutic serum level of at least one pharmaceutically active form of the compound over the time interval between dose administration.

Absolute stereochemistry is illustrated by the use of hashed and solid wedge bonds. As shown in Illus-I and Illus-II. Accordingly, the methyl group of Illus-I is emerging from the page of the paper and the ethyl group in Illus-II is descending into the page, where the cyclohexene ring resides within the plane of the paper. It is assumed that the hydrogen on the same carbon as the methyl group of Illus-I descends into the page and the hydrogen on the same carbon as the ethyl group of Illus-II emerges from the page. The convention is the same where both a hashed and solid rectangle are appended to the same carbon as in Illus-III, the Methyl group is emerging from the plane of the paper and the ethyl group is descending into the plane of the paper with the cyclohexene ring in the plane of the paper.

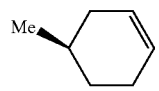

Illus-I

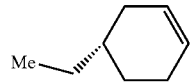

Illus-2

-continued

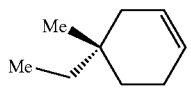

Illus-3

As is conventional, unless otherwise noted in accompanying text, ordinary "stick" bonds or "wavy" bonds indicate that all possible stereochemistry is represented, including, pure compounds, mixtures of isomers, and racemic mixtures.

As used herein, unless otherwise specified, the following terms have the following meanings:

The phrase "at least one" used in reference to the number of components comprising a composition, for example, "at least one pharmaceutical excipient" means that one member of the specified group is present in the composition, and more than one may additionally be present. Components of a composition are typically aliquots of isolated pure material added to the composition, where the purity level of the isolated material added into the composition is the normally accepted purity level for a reagent of the type.

"at least one" used in reference to substituents on a compound or moiety appended to the core structure of a compound means that one substituent of the group of substituents specified is present, and more than one substituent may be bonded to any of the chemically accessible bonding points of the core.

Whether used in reference to a substituent on a compound or a component of a pharmaceutical composition the phrase "one or more", means the same as "at least one";

"concurrently" and "contemporaneously" both include in their meaning (1) simultaneously in time (e.g., at the same time); and (2) at different times but within the course of a common treatment schedule;

"consecutively" means one following the other;

"sequentially" refers to a series administration of therapeutic agents that awaits a period of efficacy to transpire between administering each additional agent; this is to say that after administration of one component, the next component is administered after an effective time period after the first component; the effective time period is the amount of time given for realization of a benefit from the administration of the first component;

"effective amount" or "therapeutically effective amount" is meant to describe the provision of an amount of at least one compound of the invention or of a composition comprising at least one compound of the invention which is effective in treating or inhibiting a disease or condition described herein, and thus produce the desired therapeutic, ameliorative, inhibitory or preventative effect. For example, in treating central nervous system diseases or disorders with one or more of the compounds described herein "effective amount" (or "therapeutically effective amount") means, for example, providing the amount of at least one compound of Formula A that results in a therapeutic response in a patient afflicted with a central nervous system disease or disorder ("condition"), including a response suitable to manage, alleviate, ameliorate, or treat the condition or alleviate, ameliorate, reduce, or eradicate one or more symptoms attributed to the condition and/or long-term stabilization of the condition, for example, as may be determined by the analysis of pharmacodynamic markers or clinical evaluation of patients afflicted with the condition;

"patient" and "subject" means an animal, such as a mammal (e.g., a human being) and is preferably a human being;

"prodrug" means compounds that are rapidly transformed, for example, by hydrolysis in blood, in vivo to the parent compound, e.g., conversion of a prodrug of Formula A to a compound of Formula A, or to a salt thereof; a thorough discussion is provided in T. Higuchi and V. Stella, Pro-drugs as Novel Delivery Systems, Vol. 14 of the A.C.S. Symposium Series, and in Edward B. Roche, ed., Bioreversible Carriers in Drug Design, American Pharmaceutical Association and Pergamon Press, 1987, both of which are incorporated herein by reference; the scope of this invention includes prodrugs of the novel compounds of this invention;

The term "substituted" means that one or more of the enumerated substituents can occupy one or more of the bonding positions on the substrate typically occupied by "—H", provided that such substitution does not exceed the normal valency rules for the atom in the bonding configuration presented in the substrate, and that the substitution ultimately provides a stable compound, which is to say that such substitution does not provide compounds with mutually reactive substituents located geminal or vicinal to each other; and wherein the substitution provides a compound sufficiently robust to survive isolation to a useful degree of purity from a reaction mixture.

Where optional substitution of a moiety is described (e.g. "optionally substituted") the term means that if substituents are present, one or more of the enumerated substituents for the specified substrate can be present on the substrate in a bonding position normally occupied by the default substituent normally occupying that position. For example, a default substituent on the carbon atoms of an alkyl moiety is a hydrogen atom, an optional substituent can replace the default substituent.

As used herein, unless otherwise specified, the following terms used to describe moieties, whether comprising the entire definition of a variable portion of a structural representation of a compound of the invention or a substituent appended to a variable portion of a structural representation of a group of compounds of the invention have the following meanings, and unless otherwise specified, the definitions of each term (i.e., moiety or substituent) apply when that term is used individually or as a component of another term (e.g., the definition of aryl is the same for aryl and for the aryl portion of arylalkyl, alkylaryl, arylalkynyl moieties, and the like); moieties are equivalently described herein by structure, typographical representation or chemical terminology without intending any differentiation in meaning, for example, an "acyl" substituent may be equivalently described herein by the term "acyl", by typographical representations "R'—(C═O)—" or "R'—C(O)—", or by a structural representation:

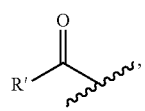

equally, with no differentiation implied using any or all of these representations;

"alkyl" (including the alkyl portions of other moieties, such as trifluoromethyl-alkyl- and alkoxy-) means an aliphatic hydrocarbon moiety comprising up to about 20 carbon atoms (for example, a designation of "$C_{1-20}$-alkyl"

indicates an aliphatic hydrocarbon moiety of from 1 to 20 carbon atoms). In some embodiments, alkyls preferably comprise up to about 10 carbon atoms, unless the term is modified by an indication that a shorter chain is contemplated, for example, an alkyl moiety of from 1 up to 8 carbon atoms and may also be designated herein "$C_{1-8}$-alkyl". The term "alkyl" is further defined by "Linear", "Branched" or "Cyclic. Where the term "alkyl" is indicated with two hyphens (i.e., "-alkyl-" it indicates that the alkyl moiety is bonded in a manner that the alkyl moiety connects the substituents on either side of it, for example, "-alkyl-Cl" indicates an alkyl moiety connecting a chloride substituent to the moiety to which the alkyl is bonded on the other end.

The term "linear-alkyl" includes alkyl moieties which comprise a hydrocarbon chain with no aliphatic hydrocarbon "branches" appended to it, although other substituents may replace a C—H bond on the hydrocarbon chain. Examples of linear alkyl include, but are not limited to, methyl-, ethyl-, n-propyl-, n-butyl-, n-pentyl- or n-hexyl-.

The term "branched-alkyl" is a moiety comprising a main hydrocarbon chain of up to the maximum specified number of carbon atoms with a lower-alkyl chain appended to one or more of the carbon atoms comprising, but not terminating, the main hydrocarbon chain. A branched alkyl moiety therefore comprises at least 3 carbon atoms in the main chain. Examples of branched alkyl moieties include, but are not limited to, t-butyl-, neopentyl-, or 2-methyl-4-ethyl-hexyl- The term "cyclic-alkyl" (equivalently "cycloalkyl") means a moiety having a main hydrocarbon chain forming a mono- or bicyclo-cyclic aliphatic moiety comprising at least 3 carbon atoms (the minimum number necessary to provide a monocyclic moiety) up to the maximum number of specified carbon atoms, generally 8 for a monocyclic moiety and 10 for a bicyclic moiety. Examples of cycloalkyl moieties include, but are not limited to, cyclopropyl, cyclobutyl, cyclopentyl or cyclohexyl. The term cyclic-alkyl (equivalently "cycloalkyl") also includes non-aromatic, fused multicyclic ring system comprising up to 20 carbon atoms which may optionally be substituted. Suitable multicyclic cycloalkyls are, for example, but are not limited to: 1-decalin; norbornyl; adamantly; and the like;

The term "lower cyclic alkyl" means a cycloalkyl comprising less than 6 carbon atoms, e.g., cyclopropyl, cyclobutyl, cyclopentyl, cyclohexyl;

As used here, the term "geminal-cycloalkyl" means a cycloalkyl moiety in which one of the ring carbons is bonded through at least one methylene group and two bonds to form a "link" between two portions of the molecule, giving the structure:

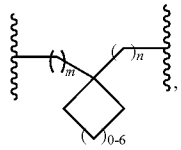

wherein at least one of m or n is 1 and the sum of m+n is four or less, for example, for example, but not limited to:

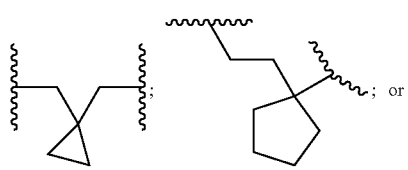

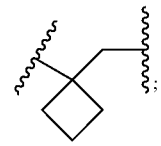

As used herein, when the term "alkyl" is modified by "substituted" or "optionally substituted", it means that one or more C—H bonds in the alkyl moiety group is substituted, or optionally may be substituted, by a substituent bonded to the alkyl substrate which is called out in defining the moiety.

"lower alkyl" means a linear, branched, or cycloalkyl moiety comprising up to 6 carbon atoms; non-limiting examples of suitable lower alkyl groups include methyl, ethyl, n-propyl, isopropyl, n-butyl, t-butyl, n-pentyl, isopentyl, neopentyl, n-hexyl, and the like;

Heterocycloalkyl- means a non-aromatic saturated monocyclic or multicyclic ring system comprising 3 to 10 ring atoms, preferably 5 to 10 ring atoms, in which one or more of the atoms in the ring system is an element other than carbon, for example nitrogen (e.g. piperidyl- or pyrrolidinyl), oxygen (e.g. furanyl and tetrahydropyranyl) or sulfur (e.g. tetrahydrothiophenyl and tetrahydrothiopyranyl); and wherein the heteroatoms can be alone or in combination provided that the moiety does not contain adjacent oxygen and/or sulfur atoms present in the ring system, for example:

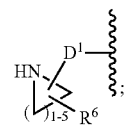

where a structural formula represents bonding between a moiety and a substrate using a the bonding line that terminates in the middle of the structure, for example the following representations:

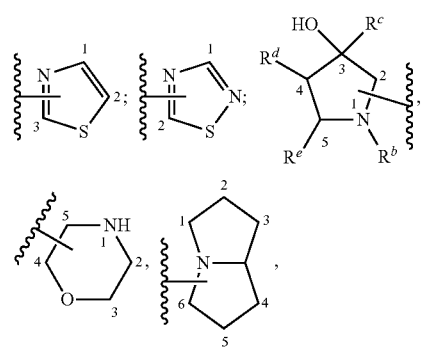

whether or not numbered the structure indicates that unless otherwise defined the moiety may be bonded to the substrate through any of available ring atom, for example, the numbered atoms of the example moieties;

"halogen" means fluorine, chlorine, bromine, or iodine; preferred halogens, unless specified otherwise where the term is used, are fluorine, chlorine and bromine, a substituent which is a halogen atom means —F, —Cl, —Br, or I, and "halo" means fluoro, chloro, bromo, or iodo substituents bonded to the moiety defined, for example, "haloalkyl" means an alkyl, as defined above, wherein one or more of the bonding positions on the alkyl moiety typically occupied by hydrogen atoms are instead occupied by a halo group, perhaloalkyl (or "fully halogenated" alkyl) means that all bonding positions not participating in bonding the alkyl substituent to a substrate are occupied by a halogen, for example, where the alkyl is selected to be methyl, the term perfluoroalkyl means $-CF_3$; and bonding sequence is indicated by hyphens where moieties are represented in text, for example alkyl, indicates a single bond between a substrate and an alkyl moiety, -alkyl-X, indicates that an alkyl group bonds an "X" substituent to a substrate, and in structural representation, bonding sequence is indicated by a wavy line terminating a bond representation, for example:

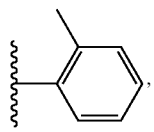 [SMILES: *c1ccccc1C]

indicates that the methylphenyl moiety is bonded to a substrate through a carbon atom ortho to the methyl substituent, while a bond representation terminated with a wavy line and drawn into a structure without any particular indication of a atom to which it is bonded indicates that the moiety may be bonded to a substrate via any of the atoms in the moiety which are available for bonding as described in the examples above.

Unsatisfied valences in the text, schemes, examples, structural formulae, and any Tables herein is assumed to have a hydrogen atom or atoms of sufficient number to satisfy the valences.

One or more compounds of the invention may also exist as, or optionally be converted to, a solvate. Preparation of solvates is generally known. Thus, for example, M. Caira et al, *J. Pharmaceutical Sci.*, 93(3), 601-611 (2004) describe the preparation of the solvates of the antifungal fluconazole in ethyl acetate as well as from water. Similar preparations of solvates, and hemisolvate, including hydrates (where the solvent is water or aqueous-based) and the like are described by E. C. van Tonder et al, *AAPS PharmSciTech.*, 5(1), article 12 (2004); and A. L. Bingham et al, *Chem. Commun.*, 603-604 (2001). A typical, non-limiting, process involves dissolving the inventive compound in desired amounts of the desired solvent (for example, an organic solvent, an aqueous solvent, water or mixtures of two or more thereof) at a higher than ambient temperature, and cooling the solution, with or without an antisolvent present, at a rate sufficient to form crystals which are then isolated by standard methods. Analytical techniques such as, for example I.R. spectroscopy, show the presence of the solvent (including water) in the crystals as a solvate (or hydrate in the case where water is incorporated into the crystalline form).

This invention also includes the compounds of this invention in isolated and purified form obtained by routine techniques. Polymorphic forms of the compounds of Formula A, and of the salts, solvates and prodrugs of the compounds of Formula A, are intended to be included in the present invention. Certain compounds of the invention may exist in different isomeric forms (e.g., enantiomers, diastereoisomers, atropisomers). The inventive compounds include all isomeric forms thereof, both in pure form and admixtures of two or more, including racemic mixtures.

In the same manner, unless indicated otherwise, presenting a structural representation of any tautomeric form of a compound which exhibits tautomerism is meant to include all such tautomeric forms of the compound.

In the same manner, unless indicated otherwise, presenting a structural representation of any tautomeric form of a compound which exhibits tautomerism is meant to include all such tautomeric forms of the compound. Accordingly, where compounds of the invention, their salts, and solvates and prodrugs thereof, may exist in different tautomeric forms or in equilibrium among such forms, all such forms of the compound are embraced by, and included within the scope of the invention. Examples of such tautomers include, but are not limited to, ketone/enol tautomeric forms, imine-enamine tautomeric forms, and for example heteroaromatic forms such as the following moieties:

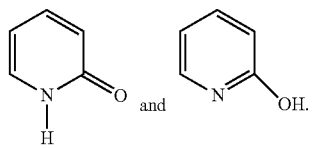 [SMILES: O=c1cccc[nH]1 ; Oc1ccccn1]

In particular, compounds of the invention are presented herein having a portion of their structure represented by the structural drawing A is contemplated as including also tautomeric form B:

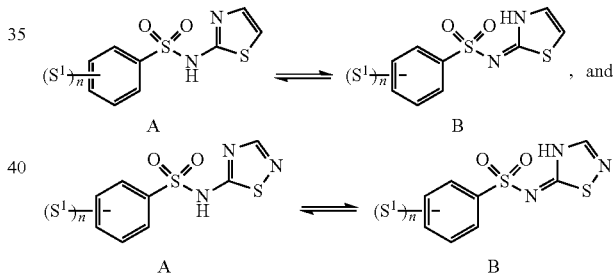

where (S1)n is one to five substituents on the aryl ring, thus, any structural drawing representation where tautomerism is possible is intended to include all tautomeric forms within the scope of the structures represented thereby.

Lone pairs of electrons having base character, for example, oxygen and nitrogen atoms in a structure, may be illustrated in either a free-base form or as coordinated to a cation having acidic character. When either structural representation is presented it contemplates both forms, as shown in the example structures A and B below:

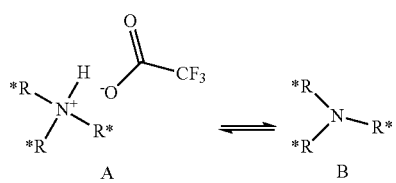

All stereoisomers of the compounds of the invention (including salts and solvates of the inventive compounds and their prodrugs), such as those which may exist due to asymmetric carbons present in a compound of the invention, and including enantiomeric forms (which may exist even in the absence of asymmetric carbons), rotameric forms, atropisomers, and diastereomeric forms, are contemplated within the scope of this invention. Individual stereoisomers of the compounds of the invention may be isolated in a pure form, for example, substantially free of other isomers, or may be isolated as an admixture of two or more stereoisomers or as a racemate. The chiral centers of the present invention can have the S or R configuration as defined by the IUPAC 1974 Recommendations. The use of the terms "salt", "solvate" "prodrug" and the like, is intended to equally apply to salts, solvates and prodrugs of isolated enantiomers, stereoisomer pairs or groups, rotamers, tautomers, or racemates of the inventive compounds.

Where diastereomeric mixtures can be separated into their individual diastereomers on the basis of their physical chemical differences by known methods, for example, by chiral chromatography and/or fractional crystallization, simple structural representation of the compound contemplates all diastereomers of the compound. As is known, enantiomers may also be separated by converting the enantiomeric mixture into a diasteromeric mixture by reaction with an appropriate optically active compound (e.g., chiral auxiliary such as a chiral alcohol or Mosher's acid chloride), separating the diastereomers and converting (e.g., hydrolyzing) the individually isolated diastereomers to the corresponding purified enantiomers.

As the term is employed herein, salts of the inventive compounds, whether acidic salts formed with inorganic and/or organic acids, basic salts formed with inorganic and/or organic bases, salts formed which include zwitterionic character, for example, where a compound contains both a basic moiety, for example, but not limited to, a nitrogen atom, for example, an amine, pyridine or imidazole, and an acidic moiety, for example, but not limited to a carboxylic acid, are included in the scope of the inventive compounds described herein. The formation of pharmaceutically useful salts from basic (or acidic) pharmaceutical compounds are discussed, for example, by S. Berge et al., Journal of Pharmaceutical Sciences (1977) 66(1) 1-19; P. Gould, International J. of Pharmaceutics (1986) 33 201-217; Anderson et al, The Practice of Medicinal Chemistry (1996), Academic Press, New York; in The Orange Book (Food & Drug Administration, Washington, D.C. on their website); and P. Heinrich Stahl, Camille G. Wermuth (Eds.), Handbook of Pharmaceutical Salts: Properties, Selection, and Use, (2002) Int'l. Union of Pure and Applied Chemistry, pp. 330-331. These disclosures are incorporated herein by reference.

The present invention contemplates all available salts, including salts which are generally recognized as safe for use in preparing pharmaceutical formulations (pharmaceutically acceptable salts) and those which may be formed presently within the ordinary skill in the art and are later classified as being "generally recognized as safe" for use in the preparation of pharmaceutical formulations, termed herein as "pharmaceutically acceptable salts". Examples of pharmaceutically acceptable acid addition salts include, but are not limited to, acetates, including trifluoroacetate salts, adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides, hydrobromides, hydroiodides, 2-hydroxyethanesulfonates, lactates, maleates, methanesulfonates, methyl sulfates, 2-naphthalenesulfonates, nicotinates, nitrates, oxalates, pamoates, pectinates, persulfates, 3-phenylpropionates, phosphates, picrates, pivalates, propionates, salicylates, succinates, sulfates, sulfonates (such as those mentioned herein), tartarates, thiocyanates, toluenesulfonates (also known as tosylates,) undecanoates, and the like.

Examples of pharmaceutically acceptable basic salts include, but are not limited to, ammonium salts, alkali metal salts such as sodium, lithium, and potassium salts, alkaline earth metal salts such as calcium and magnesium salts, aluminum salts, zinc salts, salts with organic bases (for example, organic amines) such as benzathines, diethylamine, dicyclohexylamines, hydrabamines (formed with N,N-bis(dehydroabietyl)ethylenediamine), N-methyl-D-glucamines, N-methyl-D-glucamides, t-butyl amines, piperazine, phenylcyclohexyl-amine, choline, tromethamine, and salts with amino acids such as arginine, lysine and the like. Basic nitrogen-containing groups may be converted to an ammonium ion or quarternized with agents such as lower alkyl halides (e.g. methyl, ethyl, propyl, and butyl chlorides, bromides and iodides), dialkyl sulfates (e.g. dimethyl, diethyl, dibutyl, and diamyl sulfates), long chain halides (e.g. decyl, lauryl, myristyl and stearyl chlorides, bromides and iodides), aralkyl halides (e.g. benzyl and phenethyl bromides), and others.

In general, salts of compounds are intended to be pharmaceutically acceptable salts within the scope of the invention and all acid and base salts are considered equivalent to the free forms of the corresponding compounds for purposes of the invention. Many of the compounds exemplified herein are isolated in the form of a hydrochloride, formate, or trifluoroacetate salts from the procedure by which they are synthesized. As described in the Examples, herein, for example, Ex 1-05, such salts may readily be converted to the free-base form of the compound by elution from an appropriate media using an appropriate base solution followed by chromatographic separation on a column of appropriate polarity.

The term "purified", "in purified form" or "in isolated and purified form" for a compound refers to the physical state of said compound after being isolated from a synthetic process or natural source or combination thereof. Thus, the term "purified", "in purified form" or "in isolated and purified form" for a compound refers to the physical state of said compound after being obtained from a purification process or processes described herein or well known to the skilled artisan, and in sufficient purity to be characterized by standard analytical techniques described herein or well known to the skilled artisan.

A functional group in a compound termed "protected" means that the group is in modified form to preclude undesired side reactions at the protected site when the compound is subjected to a reaction. Suitable protecting groups are known, for example, as by reference to standard textbooks, for example, T. W. Greene et al, Protective Groups in organic Synthesis (1991), Wiley, N.Y.

When a variable (e.g., aryl, cycloalkyl, $R^{XY}$, etc.) appears more than once in any moiety or in any compound of the invention, the selection of moieties defining that variable for each occurrence is independent of its definition at every other occurrence unless specified otherwise in the local variable definition.

The present invention also embraces isotopically-labeled compounds of the present invention which are structurally identical to those recited herein, but for the fact that a statistically significant percentage of one or more atoms in that form of the compound are replaced by an atom having an atomic mass or mass number different from the atomic mass or mass number of the most abundant isotope usually found in nature, thus altering the naturally occurring abundance of that isotope present in a compound of the invention. Examples of isotopes that can be preferentially incorporated into compounds of the invention include isotopes of hydrogen, carbon, nitrogen, oxygen, phosphorus, iodine, fluorine and chlorine, for example, but not limited to: $^{2}$H, $^{3}$H, $^{11}$C, $^{13}$C, $^{14}$C, $^{13}$N, $^{15}$N, $^{15}$O, $^{17}$O, $^{18}$O, $^{31}$P, $^{32}$P, $^{35}$S, $^{18}$F, and $^{36}$Cl, $^{123}$I and $^{125}$I. It will be appreciated that other isotopes may be incorporated by know means also.

Certain isotopically-labeled compounds of the invention (e.g., those labeled with $^{3}$H, $^{11}$C and $^{14}$C) are recognized as being particularly useful in compound and/or substrate tissue distribution assays using a variety of known techniques. Tritiated (i.e., $^{3}$H) and carbon-14 (i.e., $^{14}$C) isotopes are particularly preferred for their ease of preparation and detection. Further, substitution of a naturally abundant isotope with a heavier isotope, for example, substitution of protium with deuterium (i.e., $^{2}$H) may afford certain therapeutic advantages resulting from greater metabolic stability (e.g., increased in vivo half-life or reduced dosage requirements) and hence may be preferred in some circumstances. Isotopically labeled compounds of the invention can generally be prepared by following procedures analogous to those disclosed in the reaction Schemes and/or in the Examples herein below, by substituting an appropriate isotopically labeled reagent for a non-isotopically labeled reagent, or by well-known reactions of an appropriately prepared precursor to the compound of the invention which is specifically prepared for such a "labeling" reaction. Such compounds are included also in the present invention.

As used herein, the term "pharmaceutical composition" comprises at least one pharmaceutically active compound and at least one excipient, and is intended to encompass both the combination of the specified ingredients in the specified amounts, and any product which results, directly or indirectly, from combination of the specified ingredients in the specified amounts. As will be appreciated by the ordinarily skilled artisan, excipients are any constituent which adapts the composition to a particular route of administration or aids the processing of a composition into a dosage form without itself exerting an active pharmaceutical effect. A bulk composition is material that has not yet been formed into individual units for administration As mentioned above, in one aspect the invention provides compositions suitable for use in selectively inhibiting Nav 1.7 sodium channels found in sensory and sympathetic neurons, comprising at least one compound of the invention (as defined herein, for example one or more compounds of Formula A, or a salt thereof) and at least one pharmaceutically acceptable carrier (described below). It will be appreciated that pharmaceutical formulations of the invention may comprise more than one compound of the invention, for example, the combination of two or three compounds of the invention, each present by adding to the formulation the desired amount of the compound in a pharmaceutically acceptably pure form. It will be appreciated that compositions of the invention may comprise, in addition to one or more of the compounds of the invention, one or more additional compounds which also have pharmacological activity, for example, as described herein below. Such formulations are believed to have utility in the treatment, management, amelioration or in providing therapy for diseases or conditions related to pain, for example, acute pain, chronic pain, inflammatory pain, or neuropathic pain disorders, or related to pruritic disorders, or cough disorders.

In one aspect this invention provides also pharmaceutical compositions which comprise in addition to at least one pharmaceutically acceptable carrier and an effective amount of at least one compound of the invention (e.g, a compound of Formula A or a salt thereof), an effective amount of at least one other pharmaceutically active ingredient which is: (i) an opioid agonist or antagonist; (ii) a calcium channel antagonist; (iii) an NMDA receptor agonist or antagonist; (iv) a COX-2 selective inhibitor; (v) an NSAID (non-steroidal anti-inflammatory drug); or (vi) paracetamol (APAP, acetaminophen), and a pharmaceutically acceptable carrier.

While compositions of the invention may be employed in bulk form, it will be appreciated that for most applications compositions will be incorporated into a dosage form suitable for administration to a patient, each dosage form comprising an amount of the selected composition which contains an effective amount of said one or more compounds of Formula A. Examples of suitable dosage forms include, but are not limited to, dosage forms adapted for: (i) intravenous (IV) infusion, for example, over a prolonged period using an I.V. infusion pump; (ii) a dosage form adapted for intramuscular administration (IM), for example, an injectable solution or suspension, and which may be adapted to form a depot having extended release properties; (iii) a dosage form adapted for drip intravenous administration (IV), for example, a solution or suspension, for example, as an IV solution or a concentrate to be injected into a saline IV bag; or (iv) a dosage form adapted for subcutaneous administration. Other dosage forms which may be contemplated include, but are not limited to: (i) oral administration, e.g., a liquid, gel, powder, solid or semi-solid pharmaceutical composition which is loaded into a capsule or pressed into a tablet and may comprise additionally one or more coatings which modify its release properties, for example, coatings which impart delayed release or formulations which have extended release properties; (ii) a dosage form adapted for administration through tissues of the oral cavity, for example, a rapidly dissolving tablet, a lozenge, a solution, a gel, a sachets or a needle array suitable for providing intramucosal administration; (iii) a dosage form adapted for administration via the mucosa of the nasal or upper respiratory cavity, for example a solution, suspension or emulsion formulation for dispersion in the nose or airway; (iv) a dosage form adapted for transdermal administration, for example, a patch, cream or gel; (v) a dosage form adapted for intradermal administration, for example, a microneedle array; and (vi) a dosage form adapted for delivery via rectal or vaginal mucosa, for example, a suppository.

For preparing pharmaceutical compositions containing compounds of the invention, generally the compounds of the invention will be combined with one or more pharmaceutically acceptable excipients. These excipients impart to the composition properties which make it easier to handle or process, for example, lubricants or pressing aids in powdered medicaments intended to be tableted, or for example, solution stabilizing or emulsifying agents which may adapt the formulation to a desired route of administration, for example, which provide a formulation for injection, for example, intramuscular or intravenous routes of administration or administration via IV or diffusion pump infusion or other form parenteral administration, or for oral administration, for example, via absorption from the gastrointestinal tract, or for transdermal or transmucosal administration, for example, via adhesive skin "patch" or buccal administration.

These excipients are collectively termed herein "a carrier". Typically formulations may comprise up to about 95 percent active ingredient, although formulations with greater amounts may be prepared.

Pharmaceutical compositions can be solid, semi-solid or liquid. Solid form preparations can be adapted to a variety of modes of administration, examples of which include, but are not limited to, powders, dispersible granules, mini-tablets, beads, which can be used, for example, for tableting, encapsulation, or direct administration. Liquid form preparations include, but are not limited to, solutions, suspensions and emulsions which for example, but not exclusively, can be employed in the preparation of formulations intended for intravenous administration (IV), for example, but not limited to, administration via drip IV or infusion pump, intramuscular injection (IM), for example, of a bolus which is released over an extended duration, direct IV injection, or adapted to subcutaneous routes of administration. Other routes of administration which may be contemplated include intranasal administration, or for administration to some other mucosal membrane. Formulations prepared for administration to various mucosal membranes may also include additional components adapting them for such administration, for example, viscosity modifiers.

Although in some embodiments, compositions suitable for use in an IV administration, for example, IV drip or infusion pump or injection, or for subcutaneous routes of administration are preferable, a composition of the invention may be formulated for administration via other routes. Examples include aerosol preparations, for example, suitable for administration via inhalation or via nasal mucosa, may include solutions and solids in powder form, which may be in combination with a pharmaceutically acceptable propellant, for example, an inert compressed gas, e.g. nitrogen. Also included are solid form preparations which are intended to be converted, shortly before use, to a suspension or a solution, for example, for oral or parenteral administration. Examples of such solid forms include, but are not limited to, freeze dried formulations and liquid formulations adsorbed into a solid absorbent medium.

For example, the compounds of the invention may also be deliverable transdermally or transmucosally, for example, from a liquid, suppository, cream, foam, gel, or rapidly dissolving solid form. It will be appreciated that transdermal compositions can take also the form of creams, lotions, aerosols and/or emulsions and can be provided in a unit dosage form which includes a transdermal patch of any know in the art, for example, a patch which incorporates either a matrix comprising the pharmaceutically active compound or a reservoir which comprises a solid or liquid form of the pharmaceutically active compound.

Examples of pharmaceutically acceptable carriers and methods of manufacture for various compositions mentioned above may be found in A. Gennaro (ed.), Remington: The Science and Practice of Pharmacy, $20^{th}$ Edition, (2000), Lippincott Williams & Wilkins, Baltimore, Md.

The actual dosage employed may be varied depending upon the requirements of the patient and the severity of the condition being treated. Determination of the proper dosage regimen for a particular situation is within the skill in the art, for example, as described in the standard literature, for example, as described in the "Physicians' Desk Reference" (PDR), e.g., 1996 edition (Medical Economics Company, Montvale, N.J. 07645-1742, USA), the Physician's Desk Reference, $56^{th}$ Edition, 2002 (published by Medical Economics company, Inc. Montvale, N.J. 07645-1742), or the Physician's Desk Reference, $57^{th}$ Edition, 2003 (published by Thompson P D R, Montvale, N.J. 07645-1742); the disclosures of which is incorporated herein by reference thereto. For convenience, the total daily dosage may be divided and administered in portions during the day as required or delivered continuously.

In another embodiment the present invention is believed to provide for treatment, management, prevention, alleviation or amelioration of conditions or disease states which can be treated, managed, prevented, alleviated or ameliorated by specific inhibition of Nav 1.7 channel activity. Some examples are pain conditions, pruritic conditions and cough conditions. Examples of pain conditions include, but are not limited to, acute pain, perioperative pain, preoperative pain, postoperative pain, neuropathic pain, for example, post herpetic neuralgia, trigeminal neuralgia, diabetic neuropathy, chronic lower back pain, phantom limb pain, chronic pelvic pain, vulvodynia, complex regional pain syndrome and related neuralgias, pain associated with cancer and chemotherapy, pain associated with HIV, and HIV treatment-induced neuropathy, nerve injury, root avulsions, painful traumatic mononeuropathy, painful polyneuropathy, erythromelalgia, paroxysmal extreme pain disorder, small fiber neuropathy, burning mouth syndrome, central pain syndromes (potentially caused by virtually any lesion at any level of the nervous system), postsurgical pain syndromes (e.g., post mastectomy syndrome, post thoracotomy syndrome, stump pain)), bone and joint pain (osteoarthritis), repetitive motion pain, dental pain, myofascial pain (muscular injury, fibromyalgia), perioperative pain (general surgery, gynecological), chronic pain, dysmennorhea, pain associated with angina, inflammatory pain of varied origins (e.g. osteoarthritis, rheumatoid arthritis, rheumatic disease, teno-synovitis and gout), shoulder tendonitis or bursitis, gouty arthritis, and aolymyalgia rheumatica, primary hyperalgesia, secondary hyperalgesia, primary allodynia, secondary allodynia, or other pain caused by central sensitization, complex regional pain syndrome, chronic arthritic pain and related neuralgias acute pain, migraine, migraine headache, headache pain, cluster headache, non-vascular headache, traumatic nerve injury, nerve compression or entrapment, and neuroma pain, pruritic conditions, and cough conditions.

In some embodiments in which it is desired to treat a pain disorder, preferably the disorder is an acute pain, inflammatory pain or neuropathic pain disorder, more preferably an acute pain disorder.

Those skilled in the art will appreciate that treatment protocols utilizing at least one compound of the invention can be varied according to the needs of the patient. Thus, compounds of the invention used in the methods of the invention can be administered in variations of the protocols described above. For example, compounds of the invention can be administered discontinuously rather than continuously during the treatment cycle.

In accordance with the present invention, treatment, alleviation, amelioration, or management of a disease state amenable to treatment by inhibiting $Na_v$ 1.7 channel activity, for example, one or more of the conditions or disease states mentioned above, comprises administering to a patient in need thereof an effective amount of one or more compounds of the invention, as defined herein, for example, a compound of Formula A or a pharmaceutically acceptable salt thereof. In some embodiments, as mentioned above, it is preferred for the compound of the invention to be present in a pharmaceutical composition.

In general, in whatever form administered, the dosage form administered will contain an amount of at least one compound of the invention, or a salt thereof, which will provide a therapeutically effective serum level of the compound meeting or exceeding the minimum therapeutically effective serum level on a continuous basis throughout the period during which treatment is administered. As mentioned above, a composition of the invention can incorporate additional pharmaceutically active components or be administered simultaneously, contemporaneously, or sequentially with other pharmaceutically active compositions as may be additionally needed in the course of providing treatment.

In one aspect this invention provides also a pharmaceutical composition comprising a pharmaceutical carrier, an effective amount of at least one compound of the invention, for example, a compound of Formula A, and an effective amount of at least one other pharmaceutically active ingredient which is: (i) an opioid agonist or antagonist; (ii) a calcium channel antagonist; (iii) an NMDA receptor agonist or antagonist; (iv) a COX-2 selective inhibitor; (v) an NSAID (non-steroidal anti-inflammatory drug); or (vi) paracetamol (APAP, acetaminophen), and a pharmaceutically acceptable carrier.

Those skilled in the art will appreciate that treatment protocols utilizing at least one compound of the invention can be varied according to the needs of the patient. Thus, compounds of the invention used in the methods of the invention can be administered in variations of the protocols described above. For example, compounds of the invention can be administered discontinuously rather than continuously during the treatment cycle.

As mentioned above, the invention provides compounds believed to have selective activity as $Na_v$ 1.7 sodium ion channel inhibitors which have the structure of Formula A, or a salt thereof:

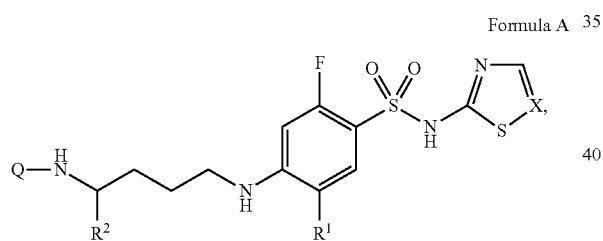

Formula A wherein $R^1$, $R^2$, Q and X are defined herein.

In some embodiments, a compound of the invention is preferably a compound of Formula AI:

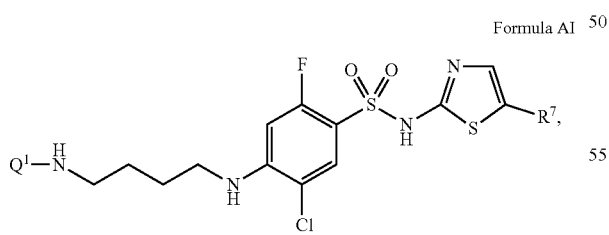

Formula AI wherein:
$R^7$ is —H, —F, or —CH$_3$, and in some embodiments is preferably —H; and
$Q^1$ is:
(i) an alkyl of up to four carbon atoms substituted on one carbon thereof with a heterocycloalkyl of up to 6 members comprising carbon and one nitrogen atom, and in some embodiments is preferably:

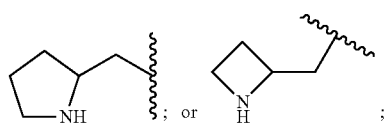

or (ii) a moiety of the formula:

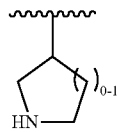

In some embodiments it is preferred for Q in the compound of Formula AI to be:

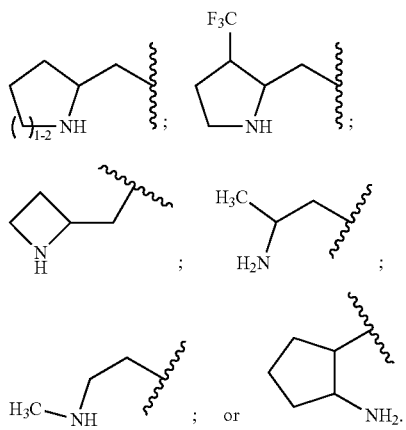

In some embodiments it is preferred for Q in the compound of Formula AI to be:

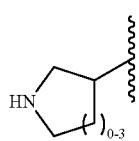

In some embodiments it is preferred for Q in the compound of Formula AI to be:

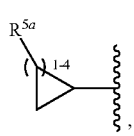

wherein one of $R^{5a}$ is NH$_2$ and the others are —H.

In some embodiments it is preferred for Q in the compound of Formula AI to be:

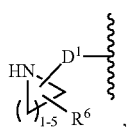

wherein
D¹ is a linear- or branched-alkyl, or a geminal-cycloalkyl moiety of up to 6 carbon atoms; and
R⁶ is optionally present as a single substituent and is linear or branched alkyl of up to 4 carbon atoms, which is optionally substituted on one or more carbon atoms thereof with —CF₃.

In some embodiments, a compound of the invention is preferably a compound of Formula AII:

Formula AII

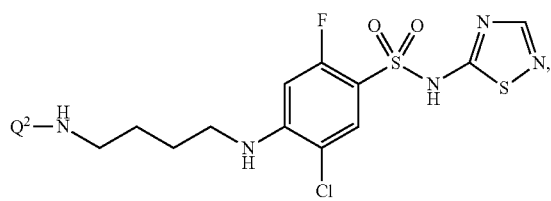

wherein Q² is:
(i) a linear, branched or cycloalkyl of up to four carbon atoms substituted on one carbon thereof with a heterocycloalkyl moiety of up to 6 members comprising carbon and one nitrogen atom, and in some embodiments is preferably:

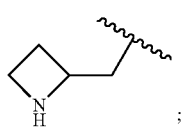 [SMILES: *CC1CCN1]

(ii) an alkyl of up to 5 carbon atoms which is substituted on one carbon atom thereof with —NH₂, and in some embodiments is preferably:

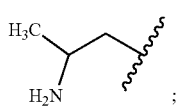

or
(iii) a cycloalkyl of up to 6 carbon atoms which is bonded via an unsubstituted ring carbon atom and wherein, one ring carbon atom thereof is substituted with NH₂, and in some embodiments R⁶ is preferably:

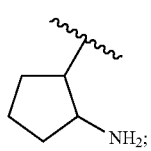

or
(iv) a moiety of the formula:

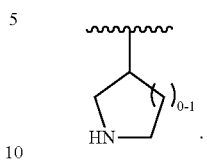

In the examples that follow certain of the exemplified compounds, or salts thereof, are prepared as pure enantiomers, or prepared from enantiopure precursors, or are isolated using chiral separation methods after synthesis, for example, chiral chromatography. After isolation of chiral compounds the absolute stereochemistry of the isolated compound was not determined in every example. Accordingly, where pure isomers have been prepared but the absolute configuration has not been verified, the enantiomer isolated in pure form is specified by the following convention.

Unless indicated otherwise in the text, where present, isomers of example compounds were not separated. Unless indicated otherwise in the text, where isomers were separated into fractions containing an excess of a particular isomer, for example, a fraction containing an excess of an optical isomer, which separation may be accomplished, for example, by super critical fluid chromatography, absolute stereochemistry of separated isomers was not determined unless indicated otherwise.

Where a reaction scheme appearing in an example employs a compound having one or more stereocenters, the stereocenters are indicated with an asterisk, as shown below in illustration compound Def-1.

Def-1

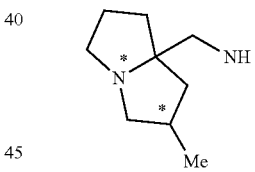

Accordingly, Def-1 consists of the following pairs of isomers: (i) Trans-isomers ((2R,7aS)-2-methylhexahydro-1H-pyrrolizin-7a-yl)methanamine (Compound ABC-1) and ((2S,7aR)-2-methylhexahydro-1H-pyrrolizin-7a-yl)methanamine (Compound ABC-2); and (ii) Cis-isomers ((2R,7aR)-2-methylhexahydro-1H-pyrrolizin-7a-yl)methanamine (Compound ABC-3) and ((2S,7aS)-2-methylhexahydro-1H-pyrrolizin-7a-yl)methanamine (Compound ABC-4).

ABC-1

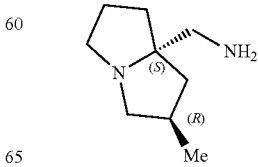

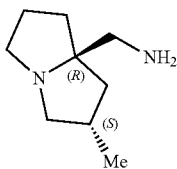
ABC-2

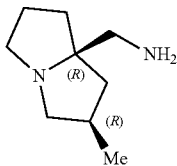
ABC-3

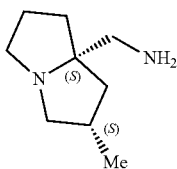
ABC-4

When the compound is prepared and separated into pure enantiomers, albeit without determining the absolute configuration of each enantiomer of the compound, the product will be identified in the title using both enantiomer names, e.g., where ABC-1 and ABC-2 are prepared and separated into pure enantiomers, the title will read "preparation of ((2R,7aS)-2-methylhexahydro-1H-pyrrolizin-7a-yl)methanamine and ((2S,7aR)-2-methylhexahydro-1H-pyrrolizin-7a-yl)methanamine. In some instances where enantiomeric compounds are prepared the designation (Cis) or (Trans) may be appended to the name to clarify the relationship of the stereo centers present in the two stereoisomers. As will be appreciated, identification of each product in the experimental preparation as "ABC-enantiomer A" or "ABC-enantiomer B" is not an association of the enantiomer prepared and isolated with any stereospecific name, only that both said enantiomers were prepared and isolated in increased enantiopurity without determination of the absolute configuration of either compound thus prepared.

Where enantiomeric compounds are prepared as pure enantiomers but the absolute configuration is not determined, they are reported as structures having asterisks indicating the chiral carbon(s) in the structural representation and the name of the compound references the stereochemistry in the alternative, for example, where ABC-3 and ABC-4 are prepared and separated the compounds will be reported with the following structure:

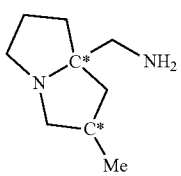
ABC-Enantiomer A

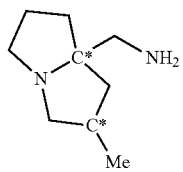
ABC-Enantiomer B and one will be named "((2R,7aR or 2S,7aS)-2-methylhexahydro-1H-pyrrolizin-7a-yl)methanamine" (e.g., ABC-enantiomer A in this example) and the other named "((2S, 7aS or 2R,7aR)-2-methylhexahydro-1H-pyrrolizin-7a-yl) methanamine" (e.g., ABC-enantiomer B in this example). In some instances where the compounds are reported as separate example numbers the associated data will be reported by example number rather than by reference to "Enantiomer A" or "Enantiomer B".

Those skilled in the art will appreciate that treatment protocols utilizing at least one compound of the invention, as described herein, may be varied according to the needs of the patient. Thus, compounds of the invention used in the methods of this invention may be administered in variations of the protocols described above. For example, the compounds of this invention may be administered discontinuously rather than continuously during the treatment cycle.

The following examples are presented to further illustrate compounds of the invention, but, with reference to the general formula presented above, they are not presented as limiting the invention to these specifically exemplified compounds.

EXAMPLES

Examples of the preparation of compounds of the invention are shown next. In each of the Examples, the identity of the compounds prepared were confirmed by a variety of techniques. In all cases the compounds were analyzed by LC/MS or HPLC.

In many of the examples, isolation of the compound is accomplished by a chromatographic technique which results in the isolation of a salt of the compound, for example, a trifluoroacetate, hydrochloride, or formate salt. It will be appreciated that the free-base of the compound may be prepared from such a salt form by ordinary techniques, for example, as shown in the following scheme.

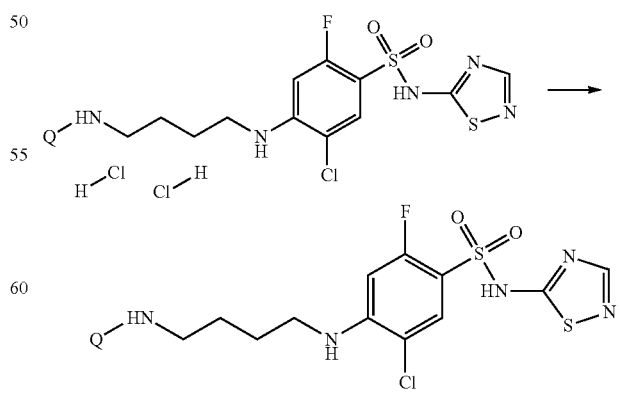

Dissolve an aliquot of the salt in a suitable quantity of a suitable solvent, for example, 500 mg of salt in 10 mL of methanol (MeOH). Load the solution onto a suitable substrate, for example, a Discovery DSC-SCX (polymerically bonded benzene sulfonic acid group on silica support) 10 g plug. Elute the substrate with a suitable solvent to was the plug onto which is absorbed the compound, for example, a suitable quantity of MeOH, followed by elution of the plug with a suitable base, for example, 2N $NH_3$ in MeOH. Collect the eluent and concentrate it to precipitate a solid material.

Re-dissolve the solid thus obtained in a suitably polar solvent, for example, water/DMSO, and load the solution onto a column of suitable polarity, for example, a 275 g C18 column. Elute the loaded column with 0-100% acetonitrile (AcCN) in water and collect the fractions containing freebase compound. Lyophylize the collected fractions to isolate the solid freebase form of the compound.

Where utilized, Prep HPLC was carried out on a Gilson 281 equipped with a Phenomenexd Synergi C18, 100 mm×21.2 mm×5 micron column. Conditions included a flow rate of 25 mL/min., eluted with a 0-40% acetonitrile/water eluent comprising 0.1% v/v TFA.

LC/MS determinations used either an Agilent YMC J'Sphere H-80 (3×50 mm) 5 μm column using mobile phase containing A: 0.1% Trifluoroacetic acid in water and B: acetonitrile with a gradient from 95:5 (A:B) to 0:100 (A:B) over 3.6 min and 0:100 (A:B) for 0.4 min at a flow rate of 1.4 mL/min, UV detection at 254 and 220 nm and Agilent 1100 quadrupole mass spectrometer or an Agilent TC-C18 (2.1×50 mm) 5 μm column using mobile phase containing A: 0.0375% Trifluoroacetic acid in water and B: 0.01875% Trifluoroacetic acid in acetonitrile with a gradient from 90:10 (A:B) for 0.4 min to 90:10 to 0:100 (A:B) over 3 min and 10:90 (A:B) for 0.6 min at a flow rate of 0.8 mL/min, UV detection at 254 and 220 nm and Agilent 6110 quadrupole mass spectrometer.

For some compounds, the identity of the compound was verified by proton NMR and high-resolution MS. Proton NMR was were acquired using a Varian Unity-Inova 400 MHz NMR spectrometer equipped with a either a Varian 400 ATB PFG 5 mm, Nalorac DBG 400-5 or a Nalorac IDG 400-5 probe in accordance with standard analytical techniques, unless specified otherwise, and results of spectral analysis are reported.

High resolving power accurate mass measurements were acquired by use of a Bruker Daltonics 7T Fourier transform ion cyclotron resonance (FTICR) mass spectrometer. Samples were dissolved in acetonitrile:water:acetic acid (50:50:0.1% v/v), and ionized by use of electrospray ionization (ESI) yielding [M+H]+ and/or [M+Na]+. External calibration was accomplished with oligomers of polypropylene glycol (PPG, average molecular weight 1000 Da).

Throughout the Examples section, the following abbreviations are used to indicate various reagents, substituents and solvents: AcCN=acetonitrile; AcOH=acetic acid; Boc=tert-butoxycarbonyl; $Boc_2O$=di-tert-butyl carbonate; Bn=Benzyl; DABCO=1,4-diazabicyclo[2.2.2]octane; DAST=diethylaminosulfur trifluoride; DCE=dichloroethane; DCM=dichloromethane; DEAD=diethylazodicarboxylate; DIPEA=diisopropylamine; DMAP=4-dimethylaminopyridine; DMB (2,4-dimethoxybenzyl-); DMF=dimethylformamide; DMP=Dess-Martin Periodinane; DMS=dimethylsulfide; DMSO=dimethylsulfoxide; DPPA=diphenylphosphoryl azide; dppf=1,1'-bis(diphenylphosphino)ferrocene; EtOAc=ethyl acetate; EtOH=ethanol; Fmoc=fluorenyloxycarbonyl; HATU=1-[Bis(dimethylamino)methylene]-1H-1,2,3-triazolo[4,5-b]pyridinium-3-oxide-hexafluorophosphate; Hex=hexanes; HMPA=hexamethylphosphoramide; HPLC=high-performance liquid chromatography; IPA=isopropyl alcohol; LC/MS=liquid chromatography/mass spectrometry; LDA=lithium diisopropylamide; LG=leaving group; LiHMDS=lithium bis(trimethylsilyl)amide; MeOH=methanol; LRMS=low resolution mass spectrometry???; MOM=methoxymethyl; MOMCl=methyl chloromethyl ether; MSCl=methanesulfonyl chloride; NMP=N-methylpyrrolidone; Pd/C=palladium on carbon; $Pd_2(dba)_3$=tris(dibenzylideneacetone)dipalladium(0); PE=petroleum ether; PG=protecting group; PMP=para-methoxybenzyl; PMBCl=para-methoxybenzyl chloride; Prep-TLC=preparative thin layer chromatography; Py=pyridine; Selectfluor=1-(chloromethyl)-4-fluoro-1,4-diazoniabicyclo[2.2.2]octane ditetrafluoroborate; SFC=Supercritical Fluid Chromatography; TBS=tert-butyldimethylsilyl; TBS-Cl=tert-butyldimethyl silyl chloride; THF=Tetrahydrofuran; TFA=trifluoroacetic acid; TFAA=trifluoroacetic acid anhydride; TsOH=para-toluenesulfonic acid; UV=ultraviolet; Xantphos=4,5-Bis(diphenylphosphino)-9,9-dimethylxanthene.

In general, compounds of the invention can be prepared by the methods outlined in Schemes A-D. Displacement of a leaving group (LG such as, but not limited to, F) in A-1 with an amine provides compounds like A-2, of which PG can then be deprotected to afford compounds A-3 (PG=protecting group such as, but not limited to, Boc, DMB, PMB, MOM, or unprotected as H).

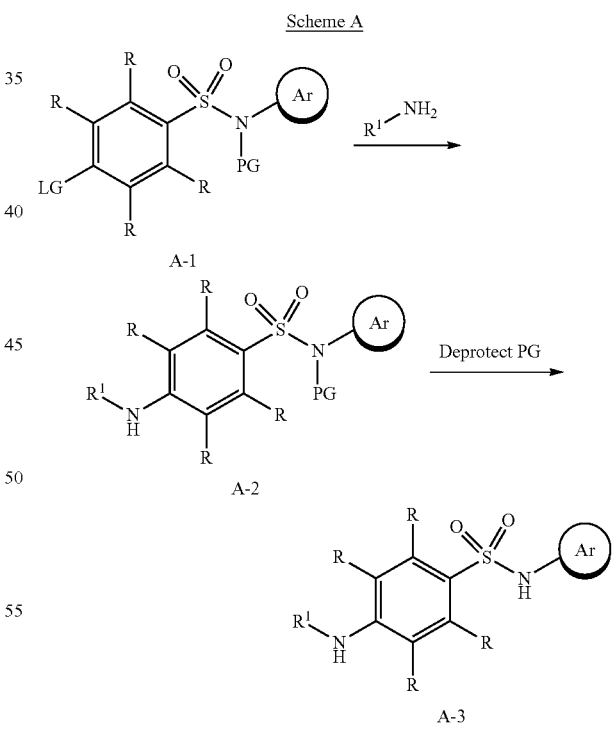

Scheme A

In addition, compounds such as A-3 that possess amine functionality on $R^1$, such as B-1, can be used in reductive amination reactions with an aldehyde B-2 followed by deprotection of a PG (PG=protecting group such as, but not limited to, Boc, DMB, PMB, MOM, or unprotected as H) to produce final compounds B-3.

Scheme B

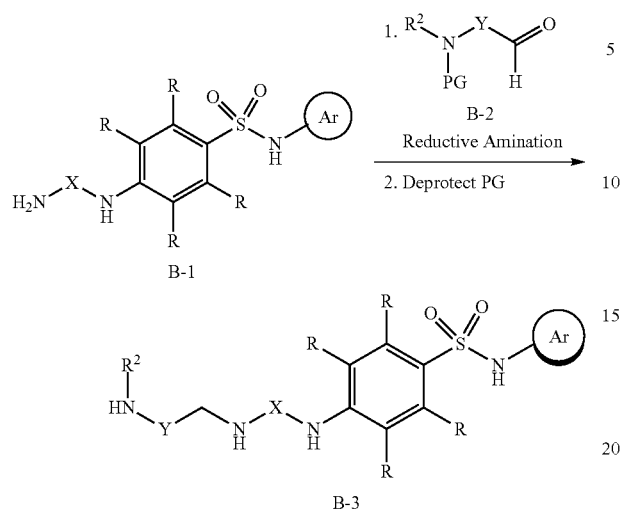

Scheme D

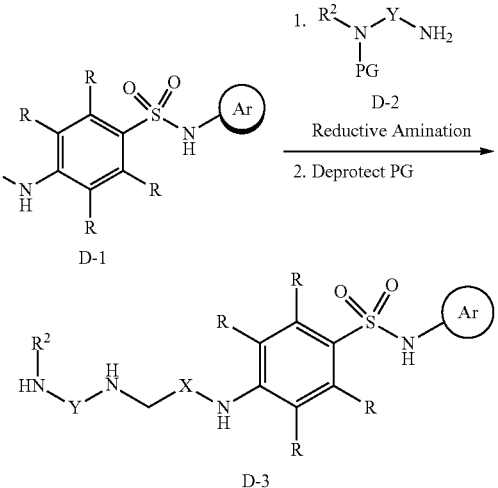

In addition, compounds with amine functionality, such as B-1, can undergo coupling reactions with acids C-1 to afford compounds such as C-2. Compounds C-2 can then be reduced and the PG (PG=protecting group such as, but not limited to, Boc, DMB, PMB, MOM, or unprotected as H) removed to afford final compounds C-3.

Scheme C

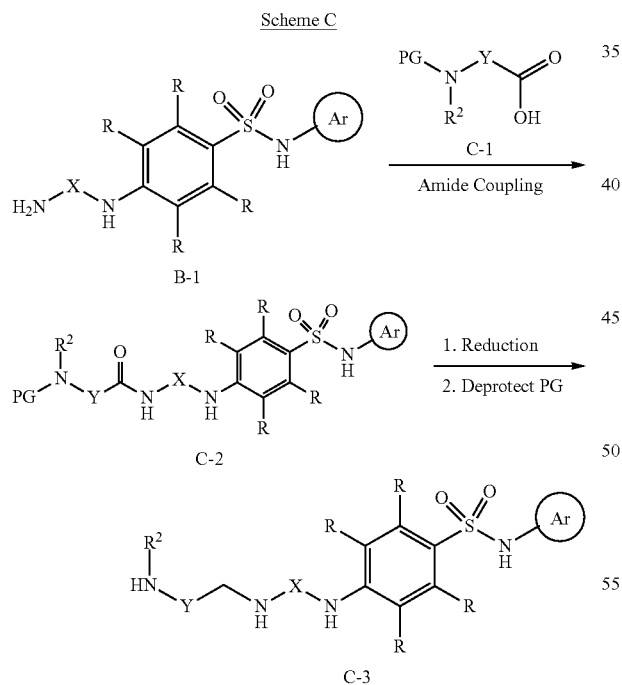

Finally, compounds such as A-3 that possess aldehyde functionality on $R^1$, such as D-1, can undergo reductive amination reactions with amines D-2, followed by deprotection of PG (PG=protecting group such as, but not limited to, Boc, DMB, PMB, MOM, or unprotected as H) to produce final compounds D-3.

Example 1: 5-chloro-2-fluoro-4-[(4-{[(2S)-piperidin-2-ylmethyl]amino}butyl)amino]-N-1,3-thiazol-2-yl-benzenesulfonamide (Ex1-04)

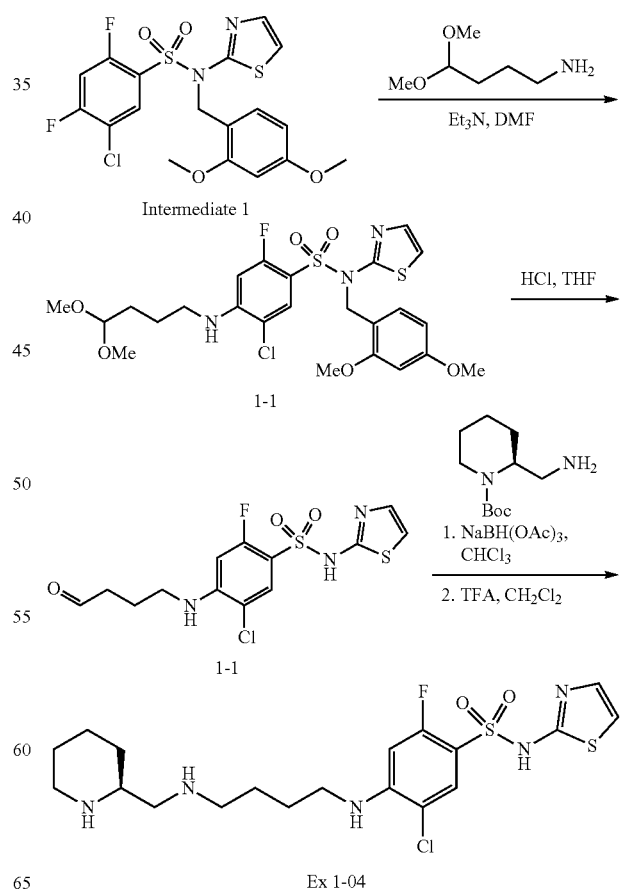

5-chloro-N-(2,4-dimethoxybenzyl)-4-((4,4-dimethoxybutyl)amino)-2-fluoro-N-(thiazol-2-yl)benzenesulfonamide (1-1)

To a solution of Intermediate 1 (5.00 g, 10.8 mmol) in DMF (31 ml) at rt was added 4-aminobutyraldehyde dimethyl acetal (1.81 g, 13.6 mmol) and Et$_3$N (4.54 ml, 32.5 mmol). The mixture was stirred at rt 3 h. The resulting mixture was quenched with 10% aq NaCl and extracted with ethyl acetate (2×). The combined extracts were washed with 10% aq NaCl (2×), dried with Na$_2$SO$_4$, filtered and concentrated. The mixture was then purified by isco silica gel chromatography (120 g RediSep Rf silica gel column, 0-50% ethyl acetate/hexanes) to give the desired product as a foam. LRMS m/z (M+H) 574.1 found, 574.1 calc'd.

5-chloro-2-fluoro-4-((4-oxobutyl)amino)-N-(thiazol-2-yl)benzenesulfonamide (1-2)

To a solution of 1-1 (5.75 g, 10.02 mmol) in THF (100 ml) at rt was added 2 N HCl (50.1 ml, 100 mmol). The mixture was stirred at rt 1 h. The reaction was quenched with water and extracted with DCM. The combined organic extracts were dried over Na2SO4, filtered and concentrated. The mixture was then purified by isco silica gel chromatography (120 g RediSep Rf silica gel column, 0-50% ethyl acetate/hexanes) to give the desired product as a solid. LRMS m/z (M+H) 378.0 found, 378.0 calc'd.

(S)-5-chloro-2-fluoro-4-((4-((piperidin-2-ylmethyl)amino)butyl)amino)-N-(thiazol-2-yl)benzenesulfonamide (Ex 1-04)

To a solution of 1-2 (100 mg, 0.265 mmol) in CHCl$_3$ (1.3 mL) was added tert-butyl (S)-2-(aminomethyl)piperidine-1-carboxylate (62 mg, 0.29 mmol), Na$_2$SO$_4$ (500 mg, 3.5 mmol), and acetic acid (30 µL, 0.53 mmol). The mixture was stirred for 1.5 h at rt. To the resulting solution was added sodium triacetoxyborohydride (112 mg, 0.53 mmol) and the reaction was stirred at rt for 30 min. The solids were filtered through a syringe filter and TFA (0.6 mL) was added to the organics. The mixture was stirred at rt an additional 30 min and then concentrated. The mixture was then purified by prep-HPLC to give the title compound which is also known as 5-chloro-2-fluoro-4-[(4-{[(2S)-piperidin-2-ylmethyl]amino}butyl)amino]-N-1,3-thiazol-2-yl-benzene-sulfonamide. $^1$H NMR (499 MHz, d$^6$-DMSO): δ 7.59 (d, J=7.1 Hz, 1H); 7.27 (d, J=4.7 Hz, 1H); 6.83 (d, J=4.7 Hz, 1H); 6.67 (d, J=12.8 Hz, 1H); 6.46 (s, 1H); 3.30-2.85 (m, 7H); 2.55 (m, 2H); 1.92 (m, 1H); 1.74 (m, 3H); 1.65-1.39 (m, 8H). LRMS m/z (M+H) 476.1 found, 476.1 calc'd.

The following compounds were prepared using the methodology herein, but substituting the appropriately substituted reagent, as described in the Reaction Schemes and Examples. The requisite starting materials were commercially available, described in the literature or readily synthesized by one skilled in the art of organic synthesis without undue experimentation.

TABLE I

| Example | Structure | IUPAC Name | LC/MS [M + H]+ |
|---|---|---|---|
| 1-5 | 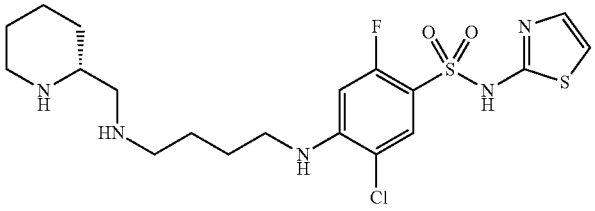 [SMILES: O=S(=O)(Nc1nccs1)c1cc(Cl)c(NCCCCNC[C@H]2CCCCN2)cc1F] | 5-chloro-2-fluoro-4-[(4-{[(2R)-piperidin-2-ylmethyl]amino}butyl)amino]-N-1,3-thiazol-2-ylbenzenesulfonamide | Calc'd 476.1, found 476.1 |
| 1-6 | 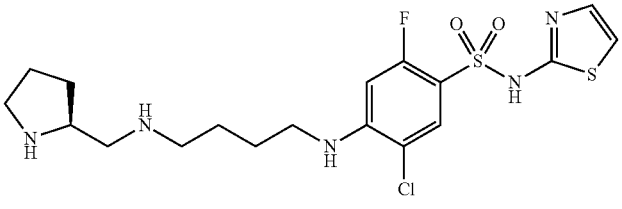 [SMILES: O=S(=O)(Nc1nccs1)c1cc(Cl)c(NCCCCNC[C@@H]2CCCN2)cc1F] | 5-chloro-2-fluoro-4-[(4-{[(2S)-pyrrolidin-2-yl-methyl]amino}butyl)-amino]-N-1,3-thiazol-2-yl-benzenesulfonamide | Calc'd 462.1, found 462.2 |
| 1-7 | 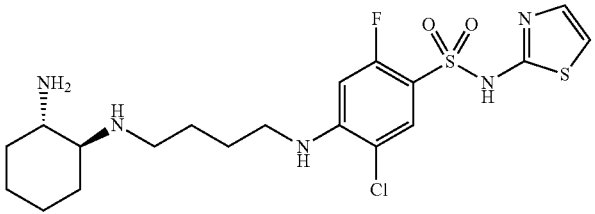 [SMILES: N[C@H]1CCCC[C@@H]1NCCCCNc1cc(F)c(S(=O)(=O)Nc2nccs2)cc1Cl] | 4-[(4-{[(1S,2S)-2-amino-cyclohexyl]amino}butyl)-amino]-5-chloro-2-fluoro-N-1,3-thiazol-2-yl-benzenesulfonamide | Calc'd 476.1, found 476.3 |

TABLE I-continued

| Example | Structure | IUPAC Name | LC/MS [M + H]+ |
|---|---|---|---|
| 1-10 | 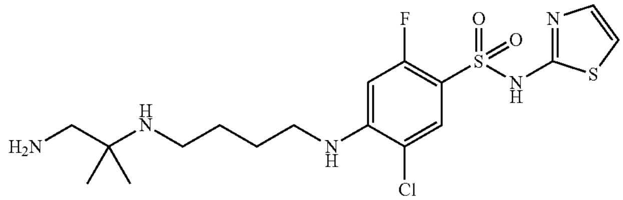 [SMILES: CC(C)(CN)NCCCCNc1cc(F)c(S(=O)(=O)Nc2nccs2)cc1Cl] | 4-({4-[(2-amino-1,1-dimethylethyl)amino]-butyl}amino)-5-chloro-2-fluoro-N-1,3-thiazol-2-yl-benzenesulfonamide | Calc'd 450.1, found 450.3 |
| 1-15 | 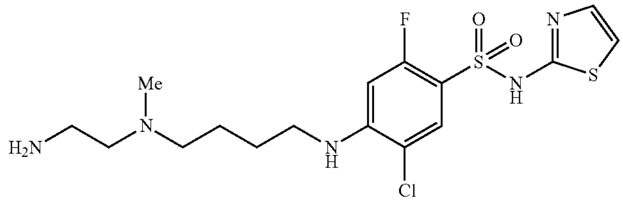 [SMILES: CN(CCN)CCCCNc1cc(F)c(S(=O)(=O)Nc2nccs2)cc1Cl] | 4-({4-[(2-aminoethyl)(methyl)amino]butyl}amino)-5-chloro-2-fluoro-N-1,3-thiazol-2-ylbenzenesulfonamide | Calc'd 436.1, found 436.3 |
| 1-27 | 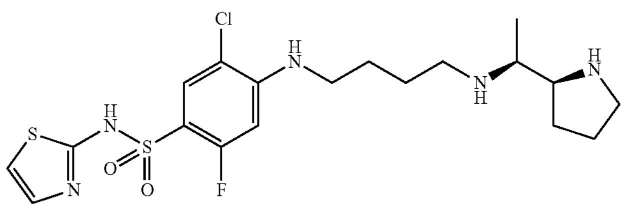 [SMILES: C[C@H](NCCCCNc1cc(F)c(S(=O)(=O)Nc2nccs2)cc1Cl)[C@@H]1CCCN1] | 5-chloro-2-fluoro-4-{[4-({(1S)-1-[(2S)-pyrrolidin-2-yl]ethyl}amino)butyl]-amino}-N-1,3-thiazol-2-yl-benzenesulfonamide | Calc'd 476.1, found 476.3 |
| 1-28 | 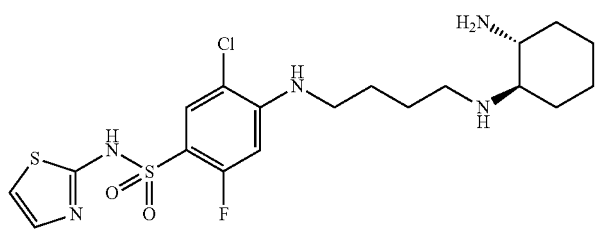 [SMILES: N[C@@H]1CCCC[C@H]1NCCCCNc1cc(F)c(S(=O)(=O)Nc2nccs2)cc1Cl] | 4-[(4-{[(1R,2R)-2-aminocyclohexyl]amino}butyl)amino]-5-chloro-2-fluoro-N-1,3-thiazol-2-ylbenzenesulfonamide | Calc'd 476.1, found 476.3 |
| 1-29 | 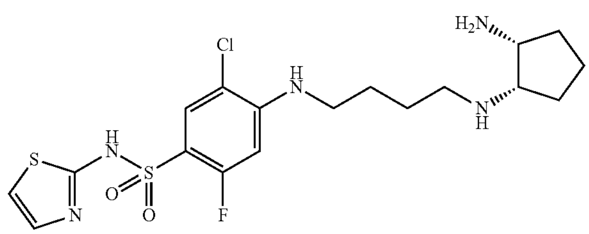 [SMILES: N[C@@H]1CCC[C@@H]1NCCCCNc1cc(F)c(S(=O)(=O)Nc2nccs2)cc1Cl] | 4-[(4-{[(1S,2R)-2-aminocyclopentyl]amino}butyl)amino]-5-chloro-2-fluoro-N-1,3-thiazol-2-ylbenzenesulfonamide | Calc'd 462.1, found 462.3 |
| 1-30 | 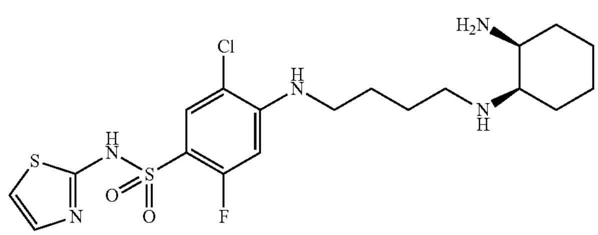 [SMILES: N[C@H]1CCCC[C@H]1NCCCCNc1cc(F)c(S(=O)(=O)Nc2nccs2)cc1Cl] | 4-[(4-{[(1R,2S)-2-aminocyclohexyl]amino}butyl)amino]-5-chloro-2-fluoro-N-1,3-thiazol-2-ylbenzenesulfonamide | Calc'd 476.1, found 476.3 |
| 1-33 | 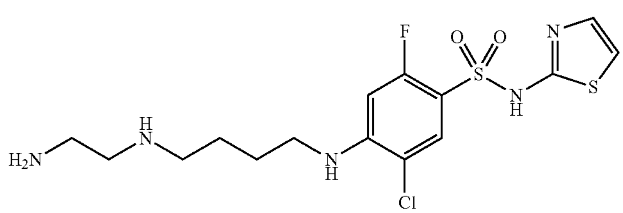 [SMILES: NCCNCCCCNc1cc(F)c(S(=O)(=O)Nc2nccs2)cc1Cl] | 4-({4-[(2-aminoethyl)amino]butyl}amino)-5-chloro-2-fluoro-N-1,3-thiazol-2-ylbenzenesulfonamide | Calc'd 422.1, found 424.2 |

TABLE I-continued

| Example | Structure | IUPAC Name | LC/MS [M + H]+ |
|---|---|---|---|
| 1-54 | 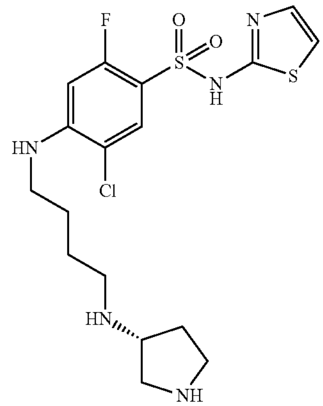 [SMILES: O=S(=O)(Nc1nccs1)c1cc(Cl)c(NCCCCN[C@@H]2CCNC2)cc1F] | 5-chloro-2-fluoro-4-({4-[(3R)-pyrrolidin-3-ylamino]butyl}amino)-N-1,3-thiazol-2-ylbenzenesulfonamide | Calc'd 448.1, found 448.3 |
| 1-55 | 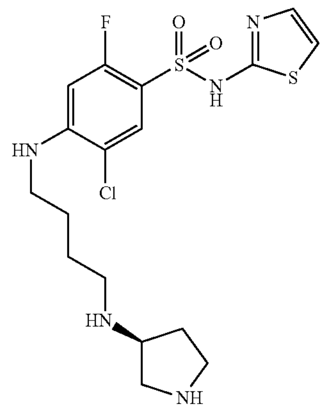 [SMILES: O=S(=O)(Nc1nccs1)c1cc(Cl)c(NCCCCN[C@H]2CCNC2)cc1F] | 5-chloro-2-fluoro-4-({4-[(3S)-pyrrolidin-3-ylamino]butyl}amino)-N-1,3-thiazol-2-ylbenzenesulfonamide | Calc'd 448.1, found 448.3 |

Compounds of the invention prepared as salts can be converted to a free-base form, for example shown below, the preparation of the TFA salt-form of Example Ex 1-05 and the preparation of the freebase form therefrom:

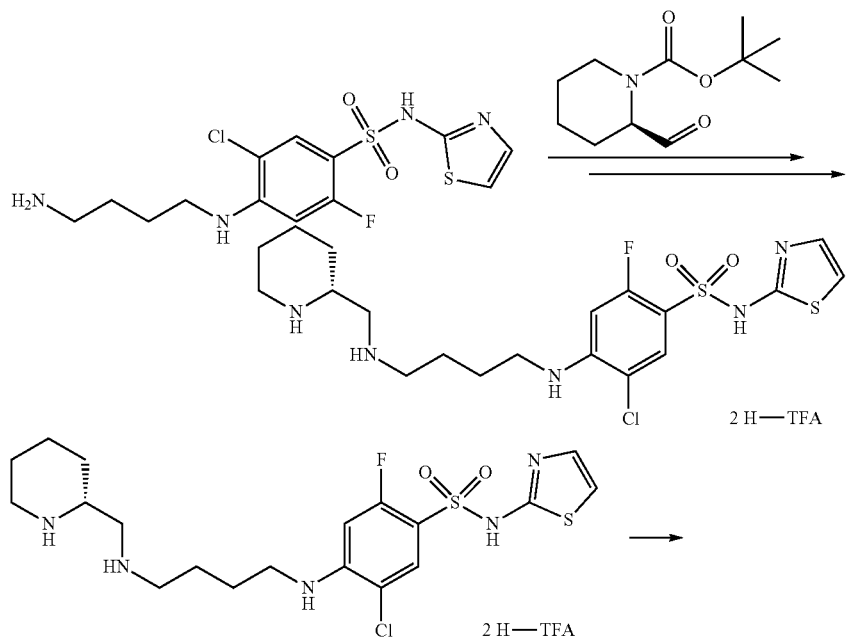

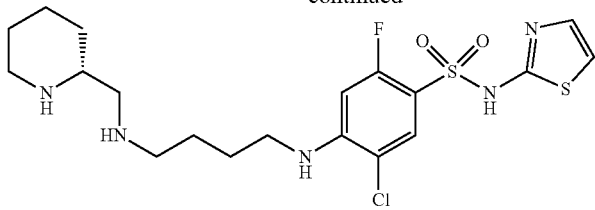

To a solution of 4-((4-aminobutyl)amino)-5-chloro-2-fluoro-N-(thiazol-2-yl)benzenesulfonamide (200 mg, 0.53 mmol) in THF (4.75 ml) and AcOH (0.5 ml) at rt was added (R)-tert-butyl 2-formylpiperidine-1-carboxylate (135 mg, 0.53 mmol). After 30 min, MP-cyanoborhydride resin (230 mg, 0.53 mmol) was added. The reaction was then stirred at rt for 12 h, filtered and concentrated. The reaction was then redissolved in DCM (0.5 ml) and TFA (0.5 ml, 6.5 mmol) was added, and the reaction was stirred at rt for 20 min, concentrated in vacuo and chromatographed using HPLC purification (30 cm×150 cm C18, 30 min 0-95% acetonitrile-water gradient, 0.05% TFA added). Free based using 5 g SCX column (eluting with 2 N NH3 in MeOH) to yield 50 mg of 4-[(2-bromo-3-chloro-phenyl)methoxy]-N-[(2,4-dimethoxyphenyl)methyl]-2,5-difluoro-N-(1,2,4-thiadiazol-5-yl)benzenesulfonamide. LCMS [M+H]+=476.6. $^1$H NMR δ (ppm)(DMSO-d6): 7.55 (d, J=7.2 Hz, 1H); 7.02 (s, 1H); 6.52 (m, 2H); 3.16 (s, 3H); 2.92 (s, 2H); 2.73-2.77 (m, 2H); 2.60-2.66 (m, 2H); 1.71 (br s, 2H); 1.38-1.54 (m, 6H); 1.24 (br s, 2H).

Example 4: (R or S) $N^1$-(2-chloro-5-fluoro-4-((thiazol-2-ylmethyl)sulfonyl)phenyl)-$N^4$—((S)-pyrrolidin-2-ylmethyl)pentane-1,4-diamine (4-5 Enantiomer A) and (S or R)—N1-(2-chloro-5-fluoro-4-((thiazol-2-ylmethyl)sulfonyl)phenyl)-N4-((S)-pyrrolidin-2-ylmethyl)pentane-1,4-diamine (Ex 4-05 Enantiomer B)

Scheme 4

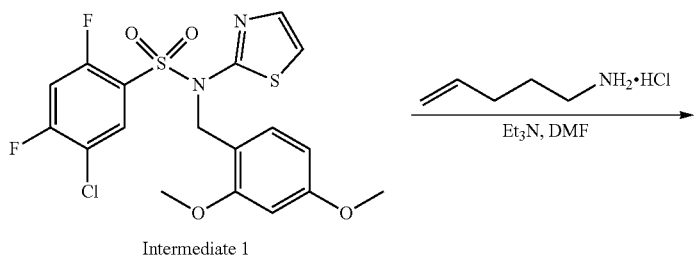

Intermediate 1

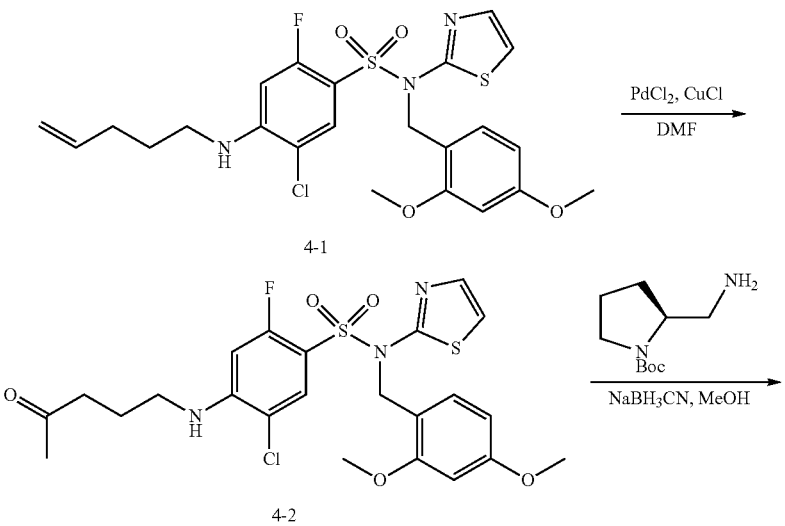

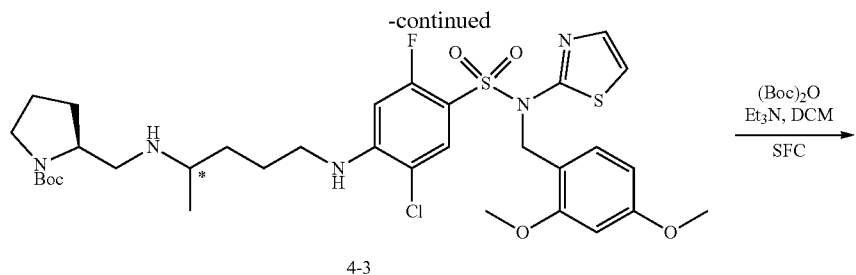

4-3

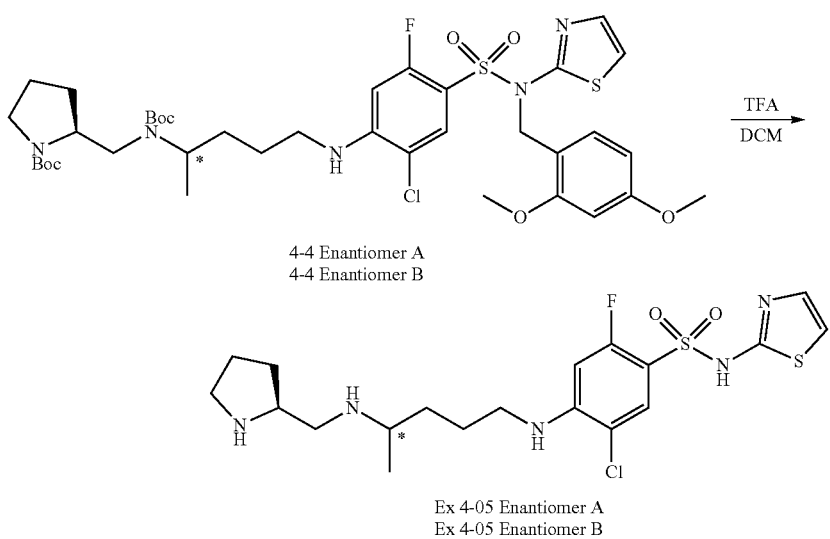

4-4 Enantiomer A
4-4 Enantiomer B

Ex 4-05 Enantiomer A
Ex 4-05 Enantiomer B

Preparation of (R and S)—$N^1$-(2-chloro-5-fluoro-4-((thiazol-2-ylmethyl)sulfonyl)phenyl)-$N^4$—((S)-pyrrolidin-2-ylmethyl)pentane-1,4-diamine (4-1)

A mixture of pent-4-en-1-amine hydrochloride (1.0 g, 8.2 mmol), Intermediate 1 (4.2 g, 9.0 mmol) and Et$_3$N (5.7 ml, 41 mmol) in DMF (30 mL) was stirred at 50° C. under N$_2$ for 16 h. Water was added and the mixture was extracted with EtOAc. The combined organic layers were washed with brine, filtered and concentrated in vacuo to give the crude product. The crude product was purified by column chromatography on silica gel (PE:EtOAc=4:1) to give the title compound as a solid. $^1$H NMR (CDCl$_3$, 400 MHz) δ 7.73 (d, J=7.2 Hz, 1H), 7.39 (d, J=3.6 Hz, 1H), 7.22 (d, J=8.4 Hz, 1H), 6.96 (d, J=3.6 Hz, 1H), 6.42-6.34 (m, 2H), 6.29 (d, J=12.4 Hz, 1H), 5.90-5.77 (m, 1H), 5.31 (s, 1H), 5.14-5.03 (m, 2H), 4.93 (br. s., 1H), 3.76 (d, J=1.6 Hz, 6H), 3.23-3.15 (m, 2H), 2.19 (q, J=7.2 Hz, 2H), 1.78 (q, J=7.2 Hz, 2H). LRMS m/z (M+H) 526.1 found, 526.1 calc'd.

5-chloro-N-(2,4-dimethoxybenzyl)-2-fluoro-4-((4-oxopentyl)amino)-N-(thiazol-2-yl)benzenesulfonamide (4-2)

A mixture of 4-1 (1.2 g, 2.3 mmol), copper(I) chloride (1.1 g, 11 mmol) and palladium(II) chloride (0.16 g, 0.91 mmol) in DMF (20 mL) and Water (2 mL) was stirred at 15° C. under O$_2$ for 16 h. Water was added and the mixture was extracted with EtOAc. The combined organic layers were washed with brine, filtered and concentrated in vacuo to give the crude product. The crude product was purified by column chromatography on silica gel (PE:EtOAc=2:1) to give the title compound as a solid. $^1$H NMR (CDCl$_3$, 400 MHz) δ 7.70 (d, J=7.2 Hz, 1H), 7.36 (d, J=3.2 Hz, 1H), 7.19 (d, J=7.6 Hz, 1H), 6.93 (d, J=3.6 Hz, 1H), 6.38-6.27 (m, 3H), 5.17 (s, 2H), 3.74 (s, 6H), 3.20-3.11 (m, 2H), 2.58 (t, J=6.4 Hz, 2H), 2.17 (s, 3H), 1.93 (q, J=6.8 Hz, 2H). LRMS m/z (M+H) 542.1 found, 542.1 calc'd.

(S)-tert-butyl 2-(((((R and S)-5-((2-chloro-4-(N-(2,4-dimethoxybenzyl)-N-(thiazol-2-yl)sulfamoyl)-5-fluorophenyl)amino)pentan-2-yl)amino)methyl)pyrrolidine-1-carboxylate (4-3)

A mixture of (S)-tert-butyl 2-(aminomethyl) pyrrolidine-1-carboxylate (0.74 g, 3.7 mmol), 4-2 (1.0 g, 1.8 mmol) and NaBH$_3$CN (0.58 g, 9.2 mmol) in MeOH (20 mL) was stirred at 15° C. for 2 h and at 50° C. under N$_2$ for 14 h. The mixture was concentrated and the crude product was purified by column chromatography on silica gel (DCM:MeOH=40:1) to give the title compound as a solid. $^1$H NMR (CDCl$_3$, 400 MHz) δ 7.56 (d, J=7.2 Hz, 1H), 7.37 (d, J=3.6 Hz, 1H), 7.19 (d, J=3.6 Hz, 1H), 7.07 (d, J=8.4 Hz, 1H), 6.57 (d, J=13.2 Hz, 1H), 6.36 (d, J=2.0, 8.0 Hz, 1H), 6.35 (dd, J=2.0, 8.0 Hz, 1H), 5.09 (s, 2H), 4.06-3.95 (m, 1H), 3.78-3.69 (m, 6H), 3.47 (d, J=6.4 Hz, 1H), 3.23-3.01 (m, 3H), 2.21-2.12 (m, 1H), 1.97-1.56 (m, 9H), 1.43 (d, J=11.2 Hz, 9H), 1.35-1.26 (m, 4H). LRMS m/z (M+H) 726.2 found, 726.3 calc'd.

(S)-tert-butyl 2-(((tert-butoxycarbonyl)((R or S)-5-((2-chloro-4-(N-(2,4-dimethoxybenzyl)-N-(thiazol-2-yl)sulfamoyl)-5-fluorophenyl)amino)pentan-2-yl)amino)methyl)pyrrolidine-1-carboxylate (4-4 Enantiomer A) and (S)-tert-butyl 2-(((tert-butoxycarbonyl)((S or R)-5-((2-chloro-4-(N-(2,4-dimethoxybenzyl)-N-(thiazol-2-yl)sulfamoyl)-5-fluorophenyl)amino)pentan-2-yl)amino)methyl)pyrrolidine-1-carboxylate (4-4 Enantiomer B)

A mixture of 4-3 (500 mg, 0.67 mmol), (Boc)$_2$O (0.64 mL, 2.8 mmol) and Et$_3$N (0.48 mL, 3.4 mmol) in DCM (20 mL) was stirred at 15° C. under N$_2$ for 16 h. Water was added and the mixture was extracted with DCM. The combined organic layers were washed with aq.NH$_4$Cl, dried over Na$_2$SO$_4$, filtered and concentrated in vacuo to give the crude product. The crude product was purified by prep-TLC (DCM:MeOH=10:1) to give 4-4 as an oil then the mixture was resolved by SFC (Chiralpak AD-H 250×4.6 mm I.D., 5 um Mobile phase: iso-propanol (0.05% DEA) in CO$_2$ from 5% to 40%, Flow rate: 2.35 mL/min, Wavelength: 220 nm) to give a faster eluting peak (4-4 Enantiomer A) as a solid and a slower eluting peak (4-4 Enantiomer B) as a solid. $^1$H NMR (CDCl$_3$, 400 MHz) δ 7.73 (br. s., 1H), 7.38 (d, J=3.6 Hz, 1H), 7.21 (d, J=9.2 Hz, 1H), 6.96 (br. s., 1H), 6.40-6.35 (m, 2H), 6.30 (d, J=11.6 Hz, 1H), 5.20 (s, 2H), 3.88 (br. s., 1H), 3.79-3.74 (m, 6H), 3.50 (br. s., 3H), 3.34 (d, J=16.4 Hz, 3H), 3.20 (br. s., 4H), 2.00-1.78 (m, 5H), 2.00-1.66 (m, 1H), 1.46 (s, 18H). LRMS m/z (M+H) 826.2 found, 826.3 calc'd.

(R or S) N$^1$-(2-chloro-5-fluoro-4-((thiazol-2-ylmethyl)sulfonyl)phenyl)-N$^4$-((S)-pyrrolidin-2-ylmethyl)pentane-1,4-diamine (4-5 Enantiomer A) and (S or R)—N1-(2-chloro-5-fluoro-4-((thiazol-2-ylmethyl)sulfonyl)phenyl)-N4-((S)-pyrrolidin-2-ylmethyl)pentane-1,4-diamine (4-5 Enantiomer B)

A mixture of 4-4 Enantiomer A (100 mg, 0.12 mmol) in DCM (2 mL) and TFA (1 mL) was stirred at 15° C. under N$_2$ for 1 h. The mixture was concentrated and the crude product was purified by prep-HPLC to give 4-5 Enantiomer A as a solid. $^1$H NMR (CD$_3$OD, 400 MHz) δ 7.66 (d, J=7.2 Hz, 1H), 7.08 (d, J=4.8 Hz, 1H), 6.70 (d, J=4.8 Hz, 1H), 6.52 (d, J=12.4 Hz, 1H), 3.85 (br. s., 1H), 3.47-3.28 (m, 6H), 3.26-3.19 (m, 1H), 2.35-2.25 (m, 1H), 2.15-1.97 (m, 2H), 1.91-1.59 (m, 5H), 1.32 (d, J=6.4 Hz, 3H). LRMS m/z (M+H) 476.1 found, 476.1 calc'd.

4-5 Enantiomer B was prepared from 4-4 Enantiomer B using a similar procedure to that of 4-5 Enantiomer A reported above. $^1$H NMR (CD$_3$OD, 400 MHz) δ 7.66 (d, J=7.2 Hz, 1H), 7.08 (d, J=4.8 Hz, 1H), 6.70 (d, J=4.4 Hz, 1H), 6.52 (d, J=12.8 Hz, 1H), 3.90-3.80 (m, 1H), 3.50-3.29 (m, 5H), 3.25 (br. s., 1H), 2.35-2.25 (m, 1H), 2.14-1.98 (m, 2H), 1.91-1.58 (m, 5H), 1.33 (d, J=6.8 Hz, 3H). LRMS m/z (M+H) 476.1 found, 476.1 calc'd.

Example 5: 4-((4-((azetidin-3-ylmethyl)amino)butyl)amino)-5-chloro-2-fluoro-N-(thiazol-2-yl)benzenesulfonamide (5-3)

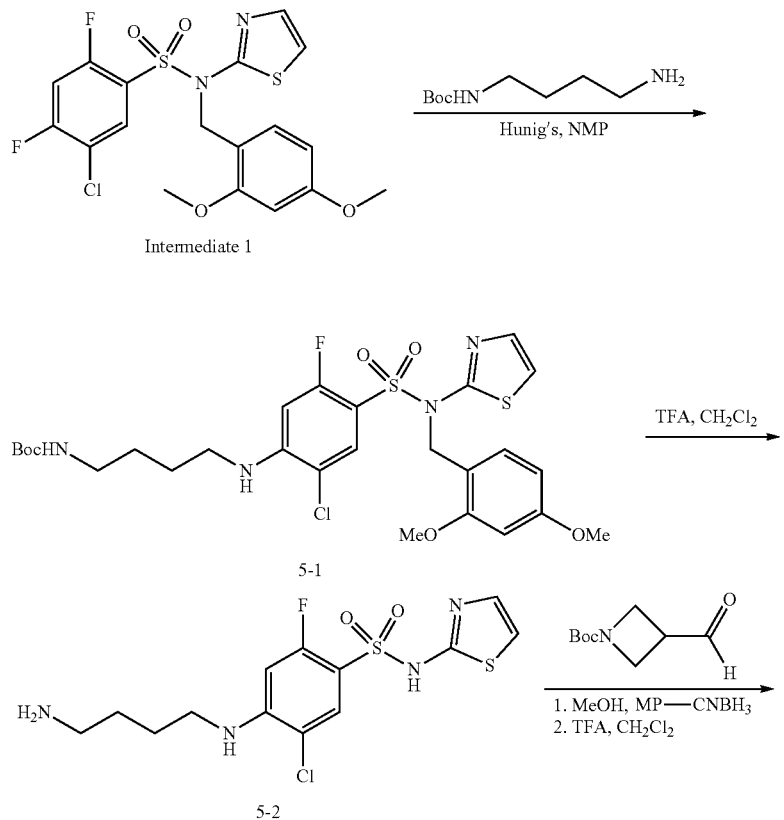

Scheme 5

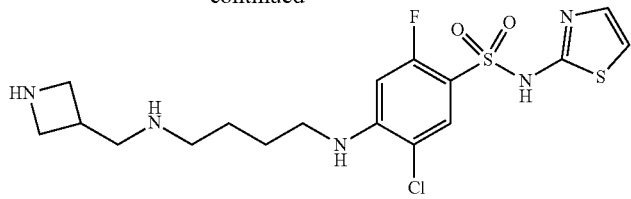

5-3

Preparation of tert-butyl (4-((2-chloro-4-(N-(2,4-dimethoxybenzyl)-N-(thiazol-2-yl)sulfamoyl)-5-fluorophenyl)amino)butyl)carbamate (5-1)

To a solution of Intermediate-1 (2.0 g, 4.3 mmol) and tert-butyl (4-aminobutyl)carbamate (0.90 g, 4.8 mmol) in NMP (21 mL) was added Hunig's base (2.3 mL, 13 mmol) at 25° C. The mixture was stirred at 70° C. in a sealed tube for 12 h. The mixture was then purified by prep-HPLC to give the desired product as an oil. LRMS m/z (M+H) 629.6 found, 629.2 calc'd.

4-((4-aminobutyl)amino)-5-chloro-2-fluoro-N-(thiazol-2-yl)benzenesulfonamide (5-2)

To a solution of 5-1 (2.0 g, 3.2 mmol) in DCM (32 mL) was added TFA (0.7 mL, 9.5 mmol) at 25° C. The mixture was stirred at 25° C. for 1 h. The mixture was then concentrated, suspended in MeOH and purified by SCX (50 g, eluting with 2 N $NH_3$ in MeOH) to give the desired product as a solid. $^1$H NMR (500 MHz, DMSO): δ 7.55 (d, J=7.2 Hz, 1H); 6.95 (d, J=3.9 Hz, 1H); 6.52 (s, 1H); 6.50 (s, 1H); 6.46 (d, J=3.9 Hz, 1H); 6.01 (s, 1H); 3.18 (m, 2H); 2.79 (m, 2H); 1.54 (m, 4H). LRMS m/z (M+H) 379.5 found, 379.0 calc'd.

4-((4-((azetidin-3-ylmethyl)amino)butyl)amino)-5-chloro-2-fluoro-N-(thiazol-2-yl)benzenesulfonamide (5-3)

To a solution of 5-2 (0.20 g, 0.53 mmol) in THF (4.8 mL) and AcOH (0.5 mL) was added tert-butyl 3-formylazetidine-1-carboxylate (0.11 g, 0.58 mmol), and the reaction was stirred for 30 min, followed by the addition of MP-cyanoborohydride (1.5 mmol). The reaction was stirred for an additional 12 h, filtered, concentrated taken up in 1:1 DCM:TFA (5 mL), stirred an additional 30 min, and concentrated. The mixture was then purified by prep-HPLC to give the desired product as an oil. $^1$H NMR (499 MHz, DMSO): δ 7.54 (d, J=7.2 Hz, 1H); 6.97 (d, J=4.0 Hz, 1H); 6.48-6.50 (m, 2H); 6.01 (s, 1H); 3.89 (t, J=9.0 Hz, 2H); 3.64 (d, J=9.0 Hz, 1H); 3.15 (d, J=7.3 Hz, 2H); 2.68 (d, J=7.3 Hz, 2H); 1.53 (br s, 3H); 1.43 (s, 3H). LRMS m/z (M+H) 448.6 found, 448.1 calc'd.

The compounds of Table 2 were prepared using the methodology herein, but substituting the appropriately substituted reagent, as described in the Reaction Schemes, Intermediates and Examples. The requisite starting materials were commercially available, described in the literature or readily synthesized by one skilled in the art of organic synthesis without undue experimentation.

TABLE 2

| Exp No. | Structure | Name | LC/MS [M + H]+ |
|---------|-----------|------|----------------|
| Ex 5-04 | 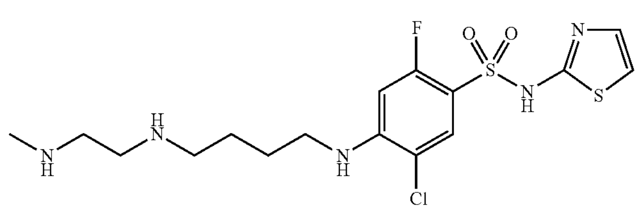 [SMILES: CNCCNCCCCNc1cc(F)c(S(=O)(=O)Nc2nccs2)cc1Cl] | 5-chloro-2-fluoro-4-((4-((2-(methylamino)butyl)amino)-N-1,3-thiazol-2-yl-benzenesulfonamide | Calc'd 436.1 Found 436.5 |

Example 7: (R)-5-chloro-2-fluoro-4-((4-((pyrrolidin-2-ylmethyl)amino)butyl)amino)-N-(thiazol-2-yl)benzenesulfonamide (7-6)

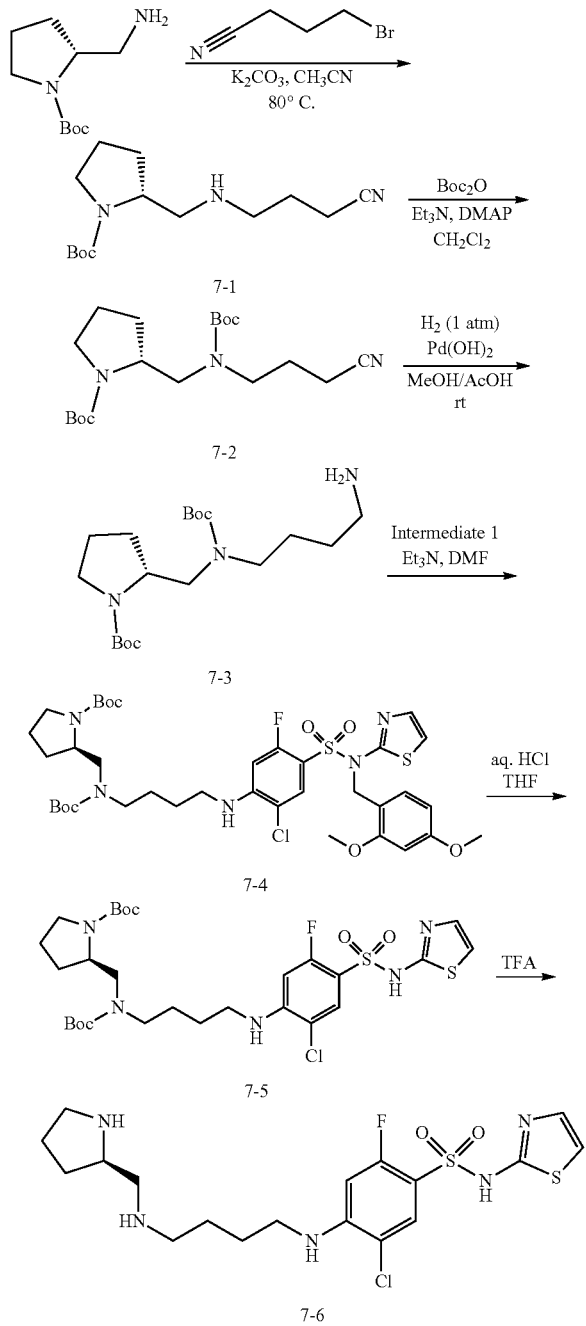

(R)-tert-butyl 2-((3-cyanopropyl)aminomethyl)pyrrolidine-1-carboxylate (7-1)

To a solution of (R)-tert-butyl 2-(aminomethyl)pyrrolidine-1-carboxylate (8.00 g, 39.9 mmol) in acetonitrile (200 ml) at rt was added 4-bromobutyronitrile (5.91 g, 39.9 mmol) and K$_2$CO$_3$ (11.6 g, 84 mmol). The mixture was heated to 75° C. for 24 h. The mixture was then cooled to rt and quenched with water and extracted with CH$_2$Cl$_2$. The combined organic extracts were dried (Na$_2$SO$_4$), filtered and concentrated to afford crude 7-1 which was used without further purification. LRMS m/z (M+H) 268.0 found, 268.2 calc'd.

(R)-tert-butyl 2-(((tert-butoxycarbonyl)(3-cyanopropyl)amino)methyl)pyrrolidine-1-carboxylate (7-2)

To a solution of 7-1 (10.7 g, 39.9 mmol) in CH$_2$Cl$_2$ (200 ml) at rt was added Boc$_2$O (11.6 ml, 49.9 mmol), triethylamine (8.34 ml, 59.9 mmol), and DMAP (0.731 g, 5.99 mmol). The mixture was stirred at rt for 2 h. The solution was quenched with water and extracted with CH$_2$Cl$_2$. The combined organic extracts were dried (Na$_2$SO$_4$), filtered and concentrated. Purification by isco silica gel chromatography (0-50% ethyl acetate/hexanes) on a 300 g Redi Sep Rf silica gel column afforded the title compound as a solid. LRMS m/z (M+H) 368.3 found, 368.3 calc'd.

(R)-tert-butyl 2-(((4-aminobutyl)(tert-butoxycarbonyl)amino)methyl)pyrrolidine-1-carboxylate (7-3)

To a solution of 7-2 (10.0 g, 27.2 mmol) in MeOH (68 ml) and Acetic Acid (68 ml) at rt was added 20% palladium hydroxide on carbon (2.00 g, 2.85 mmol). The mixture was stirred under 1 atmosphere of hydrogen (balloon) for 20 h. The mixture was filtered through celite, washed with methanol and concentrated. Purification by isco silica gel chromatography (0-25% [0.5% NH3/MeOH]:CH2Cl2) on a 330 g RediSep Rf silica gel column afforded the title compound as a clear gum. LRMS m/z (M+H) 372.4 found, 372.3 calc'd.

(R)-tert-butyl 2-(((tert-butoxycarbonyl)(4-((2-chloro-4-(N-(2,4-dimethoxybenzyl)-N-(thiazol-2-yl)sulfamoyl)-5-fluorophenyl)amino)butyl)amino)methyl)pyrrolidine-1-carboxylate (7-4)

To a solution of (R)-tert-butyl 2-(((4-aminobutyl)(tert-butoxycarbonyl)amino)methyl)-pyrrolidine-1-carboxylate 7-3 (3.88 g, 10.4 mmol) in DMF (29.8 ml) at rt was added Intermediate 1 (4.81 g, 10.44 mmol) and triethylamine (4.37 ml, 31.3 mmol). The mixture was stirred at rt 3 h. The resulting mixture was quenched with 10% aq. NaCl and extracted with ethyl acetate (2×). The combined extracts were washed with 10% aq. NaCl (2×), dried (Na$_2$SO$_4$), filtered and concentrated. Purification by isco silica gel chromatography (0-50% ethyl acetate/hexanes) afforded the title compound as a foam. LRMS m/z (M+H) 812.5 found, 812.3 calc'd.

(R)-tert-butyl 2-(((tert-butoxycarbonyl)(4-((2-chloro-5-fluoro-4-(N-(thiazol-2-yl)sulfamoyl)phenyl)amino)butyl)amino)methyl)pyrrolidine-1-carboxylate (7-5)

To a solution of 7-4 (5.45 g, 6.71 mmol) in THF (134 ml) at rt was added 2 M HCl (67.1 ml, 134 mmol). The mixture was stirred at rt for 2 h. The mixture was quenched with water and extracted with ethyl acetate. The combined organic extracts were dried (Na$_2$SO$_4$) and concentrated. Purification by silica gel chromatography (40-100% ethyl acetate/hexane) afforded the title compound as a foam. LRMS m/z (M+H) 662.4 found, 662.2 calc'd.

(R)-5-chloro-2-fluoro-4-((4-((pyrrolidin-2-ylmethyl)amino)butyl)amino)-N-(thiazol-2-yl)benzenesulfonamide (7-6)

To a solution of 7-5 (3.9 g, 5.9 mmol) in CH$_2$Cl$_2$ (44 ml) at rt was added TFA (15 ml). The mixture was stirred at rt for 1 h and concentrated to afford 7-6 as TFA salt. The TFA salt was exchanged with HCl by dissolving in MeOH (20 mL) and adding 1.25 M HCl in MeOH (30 mL). The mixture was stirred at rt for 30 min, filtered through celite and concentrated to afford the title compound as the HCl salt. $^1$H NMR (500 MHz, d$^6$-DMSO) δ 7.58 (d, J=7.2 Hz, 1H); 7.27 (d, J=4.6 Hz, 1H); 6.83 (d, J=4.6 Hz; 1H); 6.68 (d, J=12.9 Hz, 1H); 6.46 (m, 1H); 3.82 (m, 1H), 3.15-3.28 (m, 3H), 2.85-3.05 (m, 3H), 2.11 (m, 1H), 1.87 (m, 1H), 1.60 (m, 1H), 1.50-1.76 (m, 7H); LRMS m/z (M+H) 462.3 found, 462.1 calc'd.

The compounds of Table 3 were prepared using the methodology herein, but substituting the appropriately substituted reagent, as described in the Reaction Schemes and Examples. The requisite starting materials were commercially available, described in the literature or readily synthesized by one skilled in the art of organic synthesis without undue experimentation.

TABLE 3

| Example | Structure | IUPAC Name | LC/MS [M + H]+ |
|---|---|---|---|
| 7-7 | 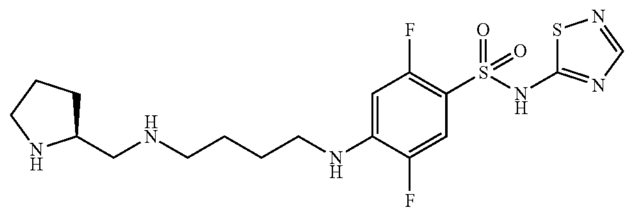 [SMILES: O=S(=O)(Nc1ncns1)c1cc(F)c(NCCCCNC[C@@H]2CCCN2)cc1F] | 2,5-difluoro-4-[(4-{[(2S)-pyrrolidin-2-ylmethyl]amino}butyl)amino]-N-1,2,4-thiadiazol-5-ylbenzenesulfonamide | Calc'd 447.1, found 447.3 |
| 7-8 | 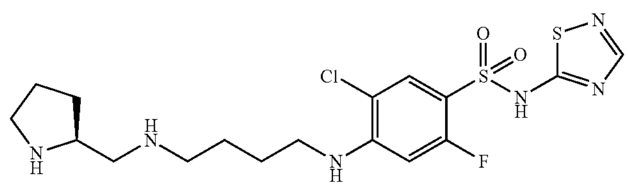 [SMILES: O=S(=O)(Nc1ncns1)c1cc(Cl)c(NCCCCNC[C@@H]2CCCN2)cc1F] | 5-chloro-2-fluoro-4-[(4-{[(2S)-pyrrolidin-2-ylmethyl]amino}butyl)amino]-N-1,2,4-thiadiazol-5-ylbenzenesulfonamide | Calc'd 463.1, found 463.3 |
| 7-9 | 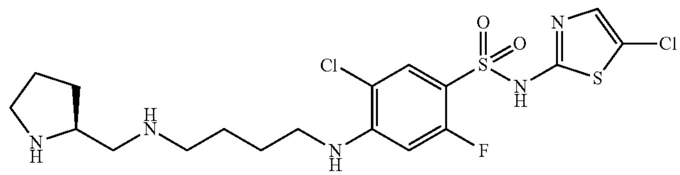 [SMILES: O=S(=O)(Nc1ncc(Cl)s1)c1cc(Cl)c(NCCCCNC[C@@H]2CCCN2)cc1F] | 5-chloro-N-(5-chloro-1,3-thiazol-2-yl)-2-fluoro-4-[(4-{[(2S)-pyrrolidin-2-ylmethyl]amino}butyl)amino]benzenesulfonamide | Calc'd 496.1, found 496.3 |
| 7-10 | 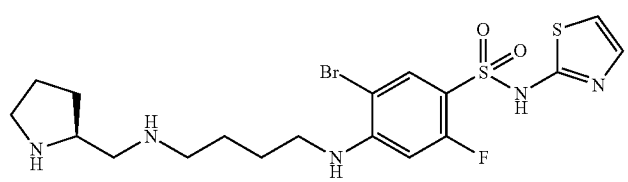 [SMILES: O=S(=O)(Nc1nccs1)c1cc(Br)c(NCCCCNC[C@@H]2CCCN2)cc1F] | 5-bromo-2-fluoro-4-[(4-{[(2S)-pyrrolidin-2-ylmethyl]amino}butyl)amino]-N-1,3-thiazol-2-ylbenzenesulfonamide | Calc'd 506.1, found 506.3 |
| 7-11 | 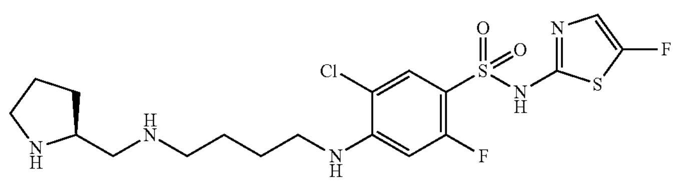 [SMILES: O=S(=O)(Nc1ncc(F)s1)c1cc(Cl)c(NCCCCNC[C@@H]2CCCN2)cc1F] | 5-chloro-2-fluoro-N-(5-fluoro-1,3-thiazol-2-yl)-4-[(4-{[(2S)-pyrrolidin-2-ylmethyl]amino}butyl)amino]benzenesulfonamide | Calc'd 480.1, found 480.3 |

Example 8: 5-chloro-2-fluoro-N-1,3-thiazol-2-yl-4-{[4-({[(2S,4S)-4-(trifluoromethyl)-pyrrolidin-2-yl]methyl}amino)butyl]amino}benzenesulfonamide (Ex8-12)

Scheme 8

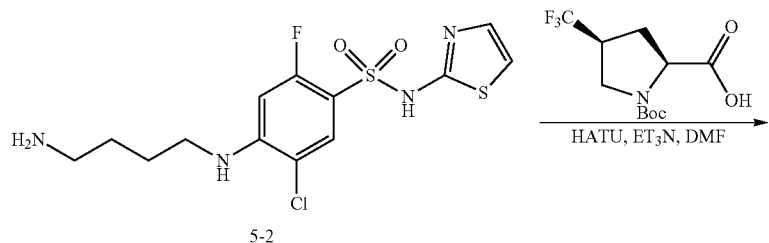

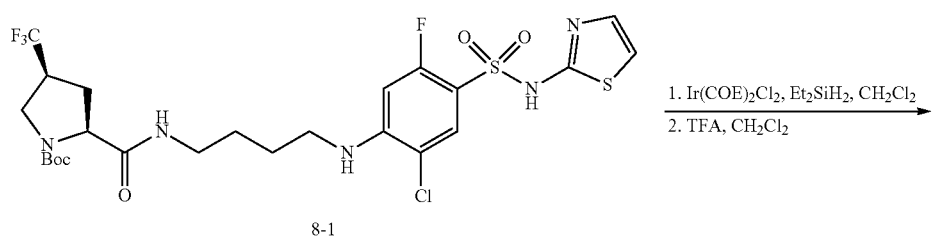

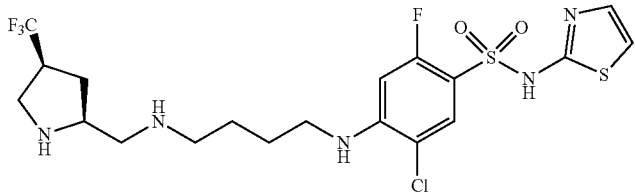

tert-butyl (2S,4S)-2-((4-((2-chloro-5-fluoro-4-(N-(thiazol-2-yl)sulfamoyl)phenyl)amino)butyl)carbamoyl)-4-(trifluoromethyl)pyrrolidine-1-carboxylate (8-1)

To a solution of 5-2 (0.30 g, 0.79 mmol), (2S,4S)-1-(tert-butoxycarbonyl)-4-(trifluoromethyl)pyrrolidine-2-carboxylic acid (0.22 g, 0.79 mmol), and Et₃N (330 ul, 2.4 mmol) in DMF (3 mL) was added HATU (0.30 g, 0.79 mmol). The reaction was stirred at rt for 1 h, quenched with 500 ul of water and extracted with 5 ml of EtOAc. Concentrated and taken on crude.

5-chloro-2-fluoro-N-1,3-thiazol-2-yl-4-{[4-({[(2S,4S)-4-(trifluoromethyl)pyrrolidin-2-yl]methyl}amino)butyl]amino}benzenesulfonamide (8-12)

Chlorobis(cyclooctene)iridium(I) dimer (6.7 mg, 7.5 μmol) was added to a uw vial containing diethylsilane (780 μmol) μl, 6.0 mmol) at rt. The mixture was stirred for 5 min, upon which time a solution of 3-1 (243 mg, 0.38 mmol) in DCM (375 uL) was added. The vial was sealed and heated to 80° C. for 2 h. The reaction was concentrated and then taken up in a 1:1 DCM:TFA (2 mL) solution and stirred for an additional 30 min at rt. The reaction was then concentrated and purified by prep-HPLC to give the desired product as an oil. ¹H NMR (500 MHz, DMSO): δ 7.59 (d; J=7.2 Hz; 1H); 7.27 (d; J=4.6 Hz; 1H); 6.83 (d; J=4.6 Hz; 1H); 6.67 (d, J=12.8 Hz, 1H); 6.45 (m; 1H); 3.81 (m; 1H); 3.17-3.30 (m; 2H); 2.93-3.03 (m; 2H); 2.54 (bs; 9H); 1.57 (m; 4H); 1.25 (s; 1H). LRMS m/z (M+H) 530.3 found, 530.1 calc'd.

The following compounds were prepared using the methodology herein, but substituting the appropriately substituted reagent, as described in the Reaction Schemes and Examples. The requisite starting materials were commercially available, described in the literature or readily synthesized by one skilled in the art of organic synthesis without undue experimentation.

TABLE 4

| Example | Structure | IUPAC Name | LC/MS [M + H]+ |
|---|---|---|---|
| 8-9 | 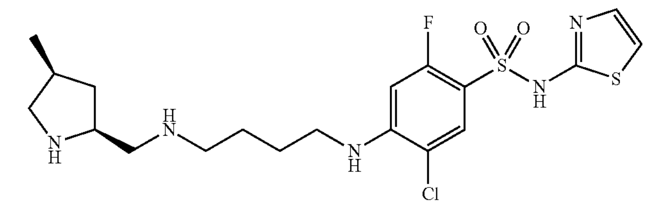 [SMILES: C[C@@H]1CN[C@H](CNCCCCNc2cc(F)c(S(=O)(=O)Nc3nccs3)cc2Cl)C1] | 5-chloro-2-fluoro-4-{[4-({[(2S,4S)-4-methylpyrrolidin-2-yl]-methyl}amino)butyl]amino}-N-1,3-thiazol-2-yl-benzenesulfonamide | Calc'd 476.1, found 476.2 |
| 8-10 | 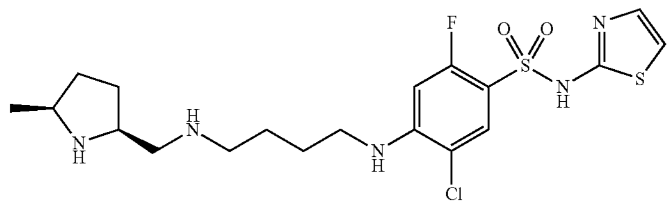 [SMILES: C[C@H]1CC[C@@H](CNCCCCNc2cc(F)c(S(=O)(=O)Nc3nccs3)cc2Cl)N1] | 5-chloro-2-fluoro-4-{[4-({[(2S,5S)-5-methylpyrrolidin-2-yl]-methyl}amino)butyl]amino}-N-1,3-thiazol-2-yl-benzenesulfonamide | Calc'd 476.1, found 476.2 |

Example 12: 4-[(4-{[(1R,2R)-2-aminocyclo-pentyl]amino}butyl)amino]-5-chloro-2-fluoro-N-1,2,4-thiadiazol-5-yl-benzene-sulfonamide (12-07)

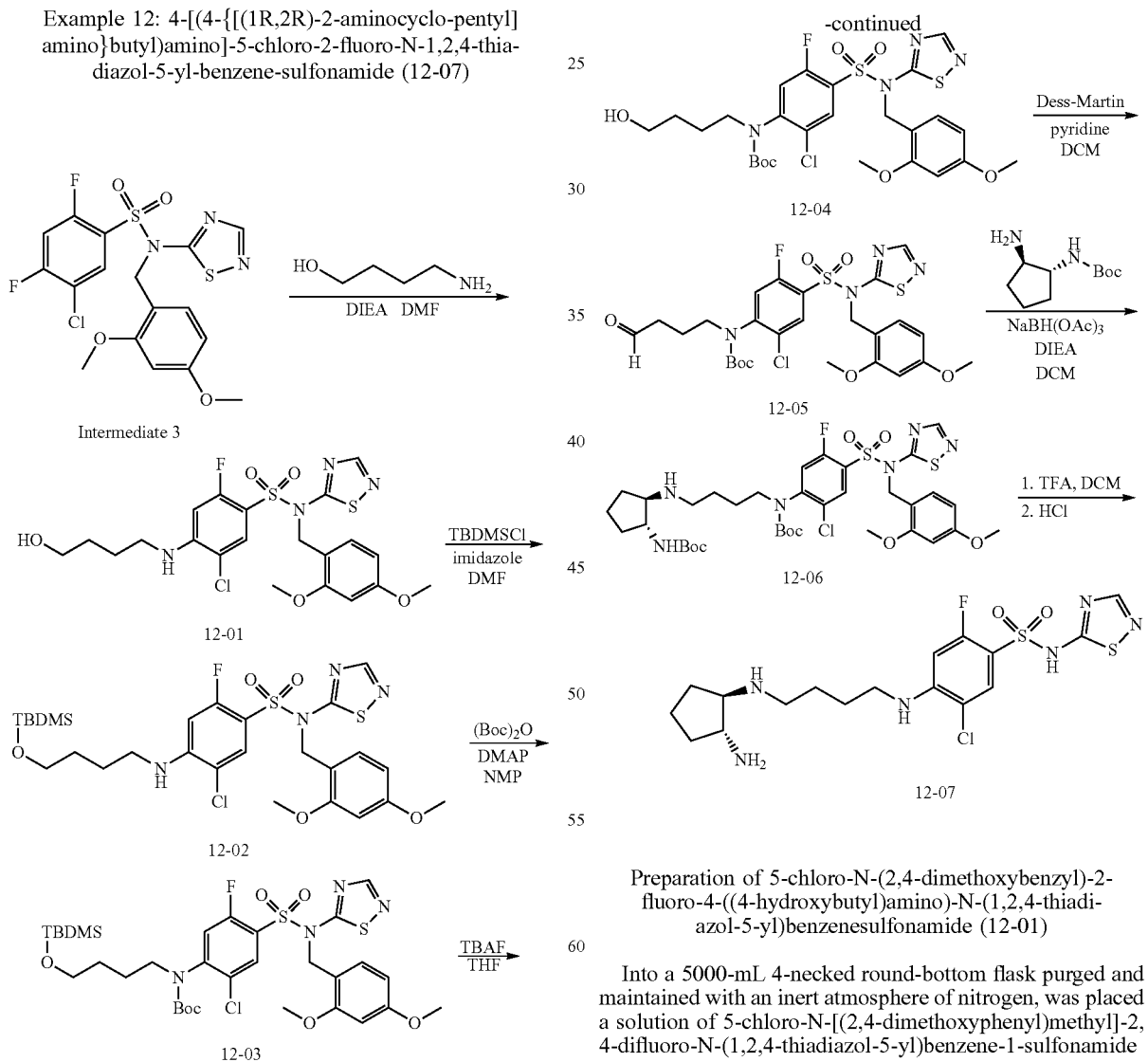

Preparation of 5-chloro-N-(2,4-dimethoxybenzyl)-2-fluoro-4-((4-hydroxybutyl)amino)-N-(1,2,4-thiadiazol-5-yl)benzenesulfonamide (12-01)

Into a 5000-mL 4-necked round-bottom flask purged and maintained with an inert atmosphere of nitrogen, was placed a solution of 5-chloro-N-[(2,4-dimethoxyphenyl)methyl]-2,4-difluoro-N-(1,2,4-thiadiazol-5-yl)benzene-1-sulfonamide (Intermediate 3, 180 g, 390 mmol, 1.00 equiv) in N,N-dimethylformamide (1.8 L), 4-aminobutan-1-ol (37 g, 415 mmol, 1.06 equiv), DIEA (76 g, 588 mmol, 1.5 equiv). The resulting solution was stirred overnight at 50° C. in an oil bath. The reaction mixture was cooled to 0° C. with a water/ice bath. The reaction was then quenched by the addition of 1000 mL of water. The resulting solution was extracted with 3×500 mL of ethyl acetate and the organic layers combined and dried over anhydrous magnesium sulfate. The residue was applied onto a silica gel column with methanol/dichloromethane (1:50-1:20) to give the title compound as a solid. LCMS m/z (M+H) calc'd: 531.09; found (M+H): 531.3.

4-((4-((tert-butyldimethylsilyl)oxy)butyl)amino)-5-chloro-N-(2,4-dimethoxybenzyl)-2-fluoro-N-(1,2,4-thiadiazol-5-yl)benzenesulfonamide (12-02)

Into a 5000-mL 4-necked round-bottom flask purged and maintained with an inert atmosphere of nitrogen, was placed a solution of 5-chloro-N-[(2,4-dimethoxyphenyl)methyl]-2-fluoro-4-[(4-hydroxybutyl)amino]-N-(1,2,4-thiadiazol-5-yl)benzene-1-sulfonamide (12-01, 165 g, 311 mmol, 1.00 equiv) in N,N-dimethylformamide (1.6 L), imidazole (42.3 g, 622 mmol, 2.00 equiv), tert-butyl(chloro)dimethylsilane (70.5 g, 468 mmol, 1.50 equiv). The resulting solution was stirred overnight at 50° C. in an oil bath. The reaction mixture was cooled to 0° C. with a water/ice bath. The reaction was then quenched by the addition of 1000 mL of water. The resulting solution was extracted with 3×500 mL of ethyl acetate and the organic layers combined and dried over anhydrous magnesium sulfate. The residue was applied onto a silica gel column with ethyl acetate/petroleum ether (1:10-1:5) to give the title compound as a solid. LCMS m/z (M+H) calc'd: 645.17; found (M+H): 645.4.

tert-butyl (4-((tert-butyldimethylsilyl)oxy)butyl)(2-chloro-4-(N-(2,4-dimethoxybenzyl)-N-(1,2,4-thiadiazol-5-yl)sulfamoyl)-5-fluorophenyl)carbamate (12-03)

Into a 5000-mL 4-necked round-bottom flask purged and maintained with an inert atmosphere of nitrogen, was placed a solution of 4-([4-[(tert-butyldimethylsilyl)oxy]butyl]amino)-5-chloro-N-[(2,4-dimethoxyphenyl)methyl]-2-fluoro-N-(1,2,4-thiadiazol-5-yl)benzene-1-sulfonamide (12-02, 150 g, 232 mmol, 1.00 equiv) in NMP (1500 mL), (Boc)2O (152 g, 696 mmol, 3.00 equiv), 4-dimethylaminopyridine (28.5 g, 233 mmol, 1.00 equiv). The resulting solution was stirred for 3 h at room temperature. The reaction mixture was cooled to 0 degree C. with a water/ice bath. The reaction was then quenched by the addition of 1000 mL of water. The resulting solution was extracted with 2×1000 mL of ethyl acetate and the organic layers combined and dried over anhydrous magnesium sulfate and concentrated under vacuum. The residue was applied onto a silica gel column with ethyl acetate/petroleum ether (1:10-1:5) to give the title compound as a solid. LCMS m/z (M+H) calc'd: 745.22; found (M+H): 745.4.

Preparation of tert-butyl (2-chloro-4-(N-(2,4-dimethoxybenzyl)-N-(1,2,4-thiadiazol-5-yl)sulfamoyl)-5-fluorophenyl)(4-hydroxybutyl)carbamate (12-04)

Into a 3000-mL 4-necked round-bottom flask purged and maintained with an inert atmosphere of nitrogen, was placed a solution of tert-butyl N-[4-[(tert-butyldimethylsilyl)oxy]butyl]-N-(2-chloro-4-[[(2,4-dimethoxyphenyl)methyl](1,2,4-thiadiazol-5-yl)sulfamoyl]-5-fluorophenyl)carbamate (12-03, 130 g, 174 mmol, 1.00 equiv) in tetrahydrofuran (1.3 L). This was followed by the addition of TBAF (262 mL, 1.50 equiv) dropwise with stirring at 0° C. The resulting solution was stirred for 5 h at 0° C. in an ice/salt bath. The reaction was then quenched by the addition of 1000 mL of water. The resulting solution was extracted with 3 mL of ethyl acetate and the organic layers combined and dried over anhydrous sodium sulfate. The residue was applied onto a silica gel column with ethyl acetate/petroleum ether (1:50-1:10) to give the title compound as a solid. LCMS m/z (M+H) calc'd: 631.14; found (M+H): 631.4.

Preparation of tert-butyl (2-chloro-4-(N-(2,4-dimethoxybenzyl)-N-(1,2,4-thiadiazol-5-yl)sulfamoyl)-5-fluorophenyl)(4-oxobutyl)carbamate (12-05)

Into a 2000-mL 4-necked round-bottom flask purged and maintained with an inert atmosphere of nitrogen, was placed a solution of tert-butyl N-(2-chloro-4-[[(2,4-dimethoxyphenyl)methyl](1,2,4-thiadiazol-5-yl)sulfamoyl]-5-fluorophenyl)-N-(4-hydroxybutyl)carbamate (12-04, 70 g, 111 mmol, 1.00 equiv) in dichloromethane (700 mL), pyridine (26.3 g, 332 mmol, 3.00 equiv). This was followed by the addition of Dess-Martin (58.8 g, 139 mmol, 1.25 equiv), in portions at 0° C. The resulting solution was stirred overnight at room temperature. The reaction mixture was cooled to 0° C. with a water/ice bath. The reaction was then quenched by the addition of 500 mL of sodium bicarbonate/water. The resulting solution was extracted with 2×1000 mL of ethyl acetate and the organic layers combined and dried over anhydrous sodium sulfate. The residue was applied onto a silica gel column with ethyl acetate/petroleum ether (1:5-1:2) to give the title compound as a solid. LCMS m/z (M+H) calc'd: 629.12; found (M+H): 629.4. $^1$H NMR (400 MHz, CDCl$_3$): δ 9.79-9.81 (1H, s), 8.19-8.23 (1H, s), 7.65-7.75 (1H, d), 7.19-7.28 (1H, d), 6.95-7.05 (1H, m), 6.32-6.35 (1H, d), 6.15-6.19 (1H, d), 5.40-5.80 (1H, s), 5.05-5.40 (1H, s), 3.65-3.80 (6H, d), 3.40-3.60 (2H, s), 2.45-2.65 (2H, s), 1.75-1.95 (2H, s), 1.20-1.50 (9H, s).

Preparation of tert-butyl (4-(((1R,2R)-2-((tert-butoxycarbonyl)amino)cyclopentyl)amino)butyl)(2-chloro-4-(N-(2,4-dimethoxybenzyl)-N-(1,2,4-thiadiazol-5-yl)sulfamoyl)-5-fluorophenyl)carbamate (12-06)

To the stirred solution of (1R,2R)-trans-N—BOC-1,2-cyclopentanediamine (1.65 g, 8.27 mmol) in DCM (42 ml) were added N-ethyl-N-isopropylpropan-2-amine (1.33 ml, 7.63 mmol) and tert-butyl (2-chloro-4-(N-(2,4-dimethoxybenzyl)-N-(1,2,4-thiadiazol-5-yl)sulfamoyl)-5-fluorophenyl) (4-oxobutyl)carbamate (12-05, 4.00 g, 6.36 mmol). The mixture was stirred at room temperature for 5 min, then was added sodium triacetoxyhydroborate (5.39 g, 25.4 mmol). The mixture was stirred at room temperature for additional 3 h. To the mixture were added sodium bicarbonate (26.7 g, 318 mmol) and more DCM (~150 ml), and mixed well. The mixture was partitioned between DCM and satd. NaHCO3. The aqueous was extracted with DCM for three times. The organic phases were combined, dried over Na2SO4, filtered, and concentrated to give the crude desired product, which was taken on to next step without further purification. LCMS m/z (M+H) calc'd: 813.28; found: 813.5.

Preparation of 4-((4-(((1R,2R)-2-aminocyclopentyl)amino)butyl)amino)-5-chloro-2-fluoro-N-(1,2,4-thiadiazol-5-yl)benzenesulfonamide dihydrochloride (12-07)

To the stirred solution of tert-butyl (4-(((1R,2R)-2-((tert-butoxycarbonyl)amino)cyclopentyl) amino)butyl)(2-chloro- 4-(N-(2,4-dimethoxybenzyl)-N-(1,2,4-thiadiazol-5-yl)sulfamoyl)-5-fluorophenyl)carbamate (12-06, crude, 6.36 mmol) in DCM (50 ml) was added TFA (49 ml, 636 mmol). The mixture was stirred at room temperature for about 1 h, and then concentrated. To the residue was added MeOH (~100 ml) and mixed well. The resulting suspension was filtered, and the filtrate was concentrated and purified by reverse HPLC (Isco CombiFlash system) using 275 g HP C18 Gold RediSepRf column, and 5-60% acetonitrile (with 0.05% TFA) in water (with 0.05% TFA) as mobile phase. To the collected pure fractions was added HCl (1M in water) (12.7 ml, 12.7 mmol), mixed well and lyophilized to give the product as solid. For C17H24ClFN6O2S2, LCMS m/z (M+H) calc'd: 463.11; found (M+H): 463.03. $^1$H NMR (500 MHz, CD$_3$OD): δ 8.207 (s, 1H); 7.678 (d, J=7.0 Hz, 1H); 6.613 (d, J=13 Hz, 1H); 3.87-3.82 (m, 1H); 3.71-3.65 (m, 1H); 3.343 (t, J=7 Hz, 2H); 3.181-3.118 (m, 2H); 2.370-2.270 (m, 2H); 1.902-1.766 (m, 8H).

Example 13: 4-[(4-{[(2R)-azetidin-2-yl-methyl]-amino}butyl)amino]-5-chloro-2-fluoro-N-1,2,4-thiadiazol-5-yl-benzene-sulfonamide (13-02)

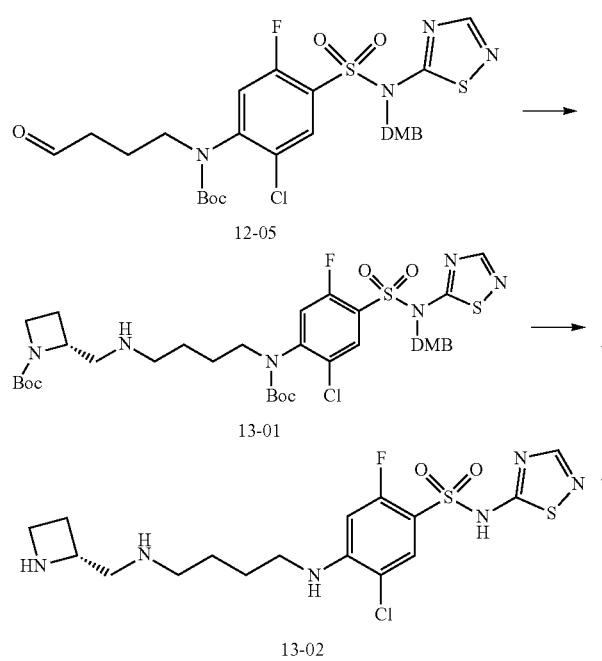

Preparation of (R)-tert-butyl 2-(((4-((tert-butoxycarbonyl)(2-chloro-4-(N-(2,4-dimethoxybenzyl)-N-(1,2,4-thiadiazol-5-yl)sulfamoyl)-5-fluorophenyl)amino)butyl)amino)methyl)azetidine-1-carboxylate (13-01)

To a solution of tert-butyl (2-chloro-4-(N-(2,4-dimethoxybenzyl)-N-(1,2,4-thiadiazol-5-yl)sulfamoyl)-5-fluorophenyl)(4-oxobutyl)carbamate (800 mg, 1.27 mmol) in DCE (20 mL) was added (R)-tert-butyl 2-(aminomethyl)azetidine-1-carboxylate (12-05, 355 mg, 1.91 mmol). The mixture was stirred in a capped round bottom flask at room temperature for 30 min. Then was added sodium triacetoxyborohydride (809 mg, 3.81 mmol) and the reaction mixture was stirred for an additional 3 hr at room temperature. The resulting reaction mixture was quenched with sat. sodium bicarbonate and then diluted with CH$_2$Cl$_2$. The organic layer was separated, dried over MgSO$_4$, filtered, and concentrated in vacuo. The residue was purified by flash chromatography (120 g ISCO cartridge) using 0-10% CH$_2$Cl$_2$/MeOH to yield the title compound. LRMS m/z (M+H) 799.5 found, 799.3 calc'd.

Preparation of (R)-4-((4-((azetidin-2-ylmethyl)amino)butyl)amino)-5-chloro-2-fluoro-N-(1,2,4-thiadiazol-5-yl)benzenesulfonamide (13-02)

To a solution of (R)-tert-butyl 2-(((4-((tert-butoxycarbonyl)(2-chloro-4-(N-(2,4-dimethoxybenzyl)-N-(1,2,4-thiadiazol-5-yl)sulfamoyl)-5-fluorophenyl)amino)butyl)amino)methyl)azetidine-1-carboxylate (13-01, 412 mg, 0.52 mmol) in CH$_2$Cl$_2$ (4 ml) was added TFA (0.40 ml, 5.2 mmol). The reaction mixture was capped and left at room temperature for 2 hr. The resulting reaction mixture was concentrated in vacuo. The residue was dissolved in 2:1 DMSO:Water and purified by reverse phase HPLC ACN w/0.05% TFA:H$_2$O w/0.05% TFA to yield the title compound as the TFA salt. The TFA salt was dissolved in 10:1 1N HCl:ACN, frozen, and dried on the lyophilizer overnight to yield the desired product as the HCl salt. LRMS m/z (M+H) 449.2 found, 449.1 calc'd. 1H NMR (400 MHz, CD3OD): δH 8.20 (1H, s), 7.67 (1H, d, J=7.2 Hz), 6.60 (1H, d, J=12.9 Hz), 4.85-4.77 (1H, m), 4.10-3.98 (2H, m), 3.71 (1H, dd, J=13.9, 8.2 Hz), 3.49 (1H, dd, J=13.9, 5.0 Hz), 3.36-3.30 (2H, m), 3.11 (2H, t, J=7.6 Hz), 2.73-2.64 (1H, m), 2.56-2.48 (1H, m), 1.83-1.70 (4H, m).

Example 14: 4-[(4-{[(2S)-azetidin-2-yl-methyl]-amino}butyl)amino]-5-chloro-2-fluoro-N-1,2,4-thiadiazol-5-ylbenzene-sulfonamide (14-04)

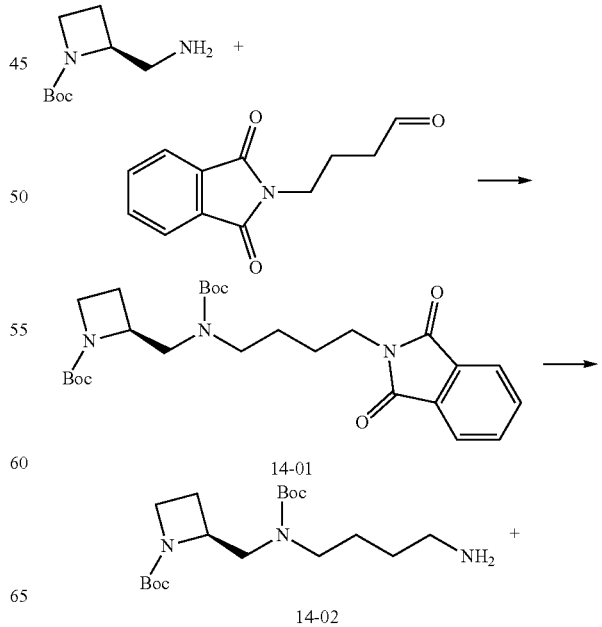

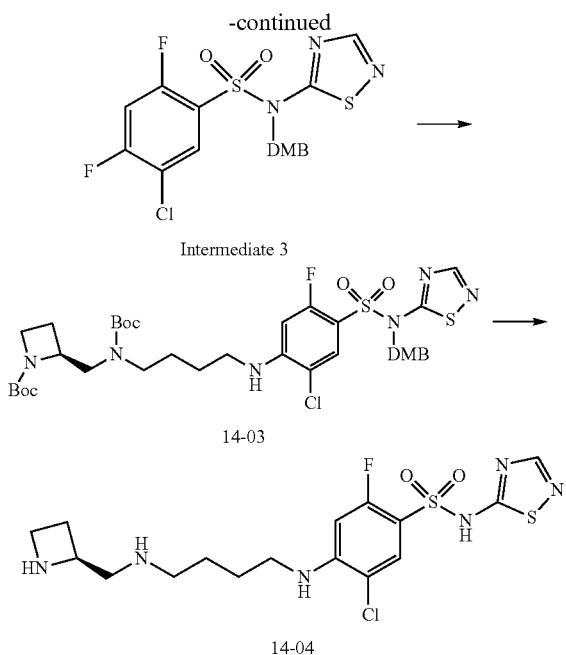

Preparation of (S)-tert-butyl 2-(((tert-butoxycarbonyl)(4-((2-chloro-4-(N-(2,4-dimethoxybenzyl)-N-(1,2,4-thiadiazol-5-yl)sulfamoyl)-5-fluorophenyl)amino)butyl)amino)methyl)azetidine-1-carboxylate (14-03)

To a solution of (S)-tert-butyl 2-(((4-aminobutyl)(tert-butoxycarbonyl)amino)methyl)azetidine-1-carboxylate (3.56 g, 9.96 mmol) in DMF (50 ml) was added 5-chloro-N-(2,4-dimethoxybenzyl)-2,4-difluoro-N-(1,2,4-thiadiazol-5-yl)benzenesulfonamide (Intermediate 3, 4.60 g, 9.96 mmol) and DIPEA (8.70 ml, 49.8 mmol). The reaction mixture was stirred at room temperature overnight under N₂ atmosphere. The resulting reaction mixture was diluted with EtOAc and then washed with H₂O three times. The resulting organic layer was separated, dried over MgSO₄, filtered, and concentrated in vacuo. The residue was purified by flash chromatography using 0-60% EtOAc/Hex to the title compound. LRMS m/z (M+H) 799.4 found, 799.3 calc'd.

4-[(4-{[(2S)-azetidin-2-yl-methyl]-amino}butyl)amino]-5-chloro-2-fluoro-N-1,2,4-thiadiazol-5-yl-benzene-sulfonamide (14-04)

To a solution of (S)-tert-butyl 2-(((tert-butoxycarbonyl)(4-((2-chloro-4-(N-(2,4-dimethoxybenzyl)-N-(1,2,4-thiadiazol-5-yl)sulfamoyl)-5-fluorophenyl)amino)butyl)amino)methyl)azetidine-1-carboxylate (950 mg, 1.19 mmol) in DCM (10 ml) was added TFA (10 ml, 130 mmol). The reaction mixture was stirred at room temperature opened to air for 1 hr. The resulting reaction mixture was concentrated in vacuo. The residue was dissolved in 10:1 DMSO: H₂O mixture and purified by reverse phase HPLC (ISCO 415 g HP-C18 column) using ACN+0.05% TFA and H₂O+0.05% TFA. The combined fractions with the desired product was concentrated in vacuo and then the residue was dissolved in 10:1 1N HCl: ACN, frozen, and dried on the lyophilizer to yield the title compound as the HCl salt. LRMS m/z (M+H) 449.3 found, 449.1 calc'd. 1H NMR (400 MHz, CD3OD): δH 8.20 (1H, s), 7.66 (1H, d, J=7.2 Hz), 6.60 (1H, d, J=12.8 Hz), 4.88-4.79 (1H, m), 4.13-3.95 (2H, m), 3.74 (1H, dd, J=13.9, 8.4 Hz), 3.49 (1H, dd, J=13.9, 4.6 Hz), 3.36-3.30 (2H, m), 3.12 (2H, t, J=7.5 Hz), 2.73-2.64 (1H, m), 2.57-2.47 (1H, m), 1.83-1.71 (4H, m).

Preparation of (S)-tert-butyl 2-(((tert-butoxycarbonyl)(4-(1,3-dioxoisoindolin-2-yl)butyl)amino)methyl) azetidine-1-carboxylate (14-01)

To a solution of (S)-2-aminomethyl-1-BOC-azetidine (5.79 g, 31.1 mmol) in DCE (80 ml) was added 4-(1,3-dioxoisoindolin-2-yl)butanal (4.50 g, 20.7 mmol). The mixture was stirred in a capped flask at room temperature for 30 min. Then was added sodium triacetoxyborohydride (13.2 g, 62.1 mmol) and the reaction mixture was stirred overnight at room temperature under N₂ atmosphere. The resulting reaction mixture was diluted with DCM and then washed with sat. NaHCO₃. The organic layer was separated, dried over MgSO₄, filtered, and concentrated in vacuo. The residue was then dissolved in DCM (100 ml) and was added BOC-anhydride (7.22 ml, 31.1 mmol) and DIPEA (9.05 ml, 51.8 mmol). The reaction mixture was stirred at room temperature under N₂ atmosphere overnight. The resulting reaction mixture was diluted with DCM and H₂O. The organic layer was separated, dried over MgSO₄, filtered, and concentrated in vacuo. The residue was purified by flash chromatography using 0-50% EtOAc/Hex to yield the title compound. LRMS m/z (M+H) 488.4 found, 488.3 calc'd.

Preparation of (S)-tert-butyl 2-(((4-aminobutyl)(tert-butoxycarbonyl)amino)methyl) azetidine-1-carboxylate (14-02)

To a solution of (S)-tert-butyl 2-(((tert-butoxycarbonyl)(4-(1,3-dioxoisoindolin-2-yl)butyl)amino)methyl)azetidine-1-carboxylate (4.84 g, 9.93 mmol) in EtOH (50 ml) was added hydrazine hydrate (4.82 ml, 99 mmol). The reaction mixture was stirred under N₂ atmosphere at 50° C. for 3 hr. The resulting reaction mixture was filtered washing with CH₂Cl₂. The filtrate was concentrated in vacuo. The residue was dissolved in CH₂Cl₂ and then washed with H₂O. The organic layer was separated, dried over MgSO₄, filtered, and concentrated in vacuo to yield the title compound. LRMS m/z (M+H) 358.4 found, 358.3 calc'd.

Example 15: 4-[(4-{[(2S)-2-aminopropyl]amino}butyl)amino]-5-chloro-2-fluoro-N-1,2,4-thiadiazol-5-ylbenzenesulfonamide (15-05)

Scheme 15

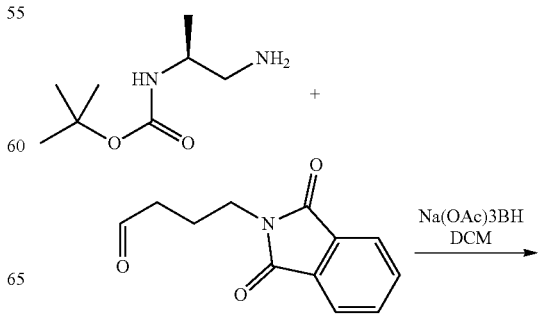

-continued

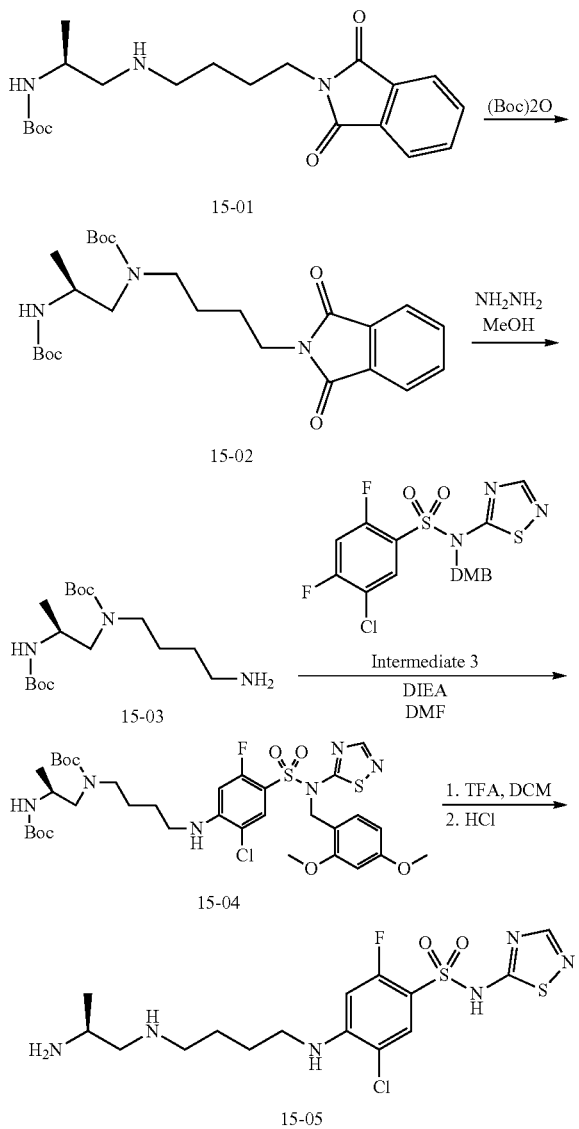

tert-butyl (S)-(1-((4-(1,3-dioxoisoindolin-2-yl)butyl)
amino)propan-2-yl)carbamate (15-01)

To the stirred solution of (S)-tert-butyl-1-aminopropan-2-yl-carbamate (5.00 g, 28.7 mmol) in Dichloromethane (153 ml) were added DIEA (5.23 ml, 29.9 mmol) and 4-(1,3-dioxoisoindolin-2-yl)butanal (5.00 g, 23.0 mmol). The mixture was stirred at room temperature for additional 10 min, then added sodium triacetoxyhydroborate (19.5 g, 92 mmol). The mixture was stirred at room temperature for about 3 h. To the mixture was added sodium bicarbonate (38.7 g, 460 mmol), mixed well, then the mixture was partitioned between DCM and satd NaHCO₃. The aqueous was extracted with DCM for three times. Organic phases were combined, dried over Na₂SO₄, filtered, and concentrated to give the crude product as an oil, which was taken on to next step without further purification. For C20H29N3O4, LCMS m/z (M+H) calc'd: 376.22; found (M+H): 376.3.

Preparation of tert-butyl (S)-(2-((tert-butoxycarbonyl)amino)propyl)(4-(1,3-dioxoisoindolin-2-yl)butyl)carbamate (15-02)

To the stirred solution of tert-butyl (S)-(1-((4-(1,3-dioxoisoindolin-2-yl)butyl)amino)propan-2-yl)carbamate (15-01, crude, 23.0 mmol) in dichloromethane (153 ml) were added DMAP (141 mg, 1.15 mmol), DIEA (5.23 ml, 29.9 mmol), and BOC-Anhydride (6.95 ml, 29.9 mmol). The mixture was stirred at room temperature for 2 h, then concentrated and purified by silica gel chromatography using Isco CombiFlash system (on a 120 g RediSep Rf silica gel column) and 0-100% EtOAc in hexane as eluent to afford the titled compound as a foam solid. For C25H37N3O6, LCMS m/z (M+H) calc'd: 476.27; found (M+H): 476.24. ¹H NMR (500 MHz, CD₃OD): δ 7.87-7.84 (m, 2H); 7.83-7.78 (m, 2H); 6.606 (d, J=13.5 Hz, 1H); 3.89-3.76 (m, 1H); 3.70 (t, J=7.5 Hz, 2H); 3.30-3.25 (m, 2H); 3.20-3.14 (m, 2H); 1.73-1.61 (m, 2H); 1.62-1.51 (m, 2H); 1.53-1.33 (m, 9H); 1.41 (s, 9H); 1.066 (d, J=7.0 Hz, 3H).

Preparation of tert-butyl (S)-(4-aminobutyl)(2-((tert-butoxycarbonyl)amino)propyl)carbamate (15-03)

To the stirred solution of (S)-tert-butyl (2-((tert-butoxycarbonyl)amino)propyl)(4-(1,3-dioxoisoindolin-2-yl)butyl) carbamate (15-02, 5.69 g, 12.0 mmol) in MeOH (60 ml) was added anhydrous hydrazine (3.76 ml, 120 mmol). The mixture was stirred at room temperature overnight, then filtered and washed with a small amount of MeOH. The filtrate was combined, concentrated, and partitioned between DCM (150 ml) and satd. NaHCO₃ (75 ml). The organic phase was separated, dried over Na₂SO₄, filtered and concentrated to give the titled product as a thick oil, which was taken on to next step without further purification. For C17H35N3O4, LCMS m/z (M+H) calc'd: 346.26; found: 346.13.

Preparation of tert-butyl (S)-(2-((tert-butoxycarbonyl)amino)propyl)(4-((2-chloro-4-(N-(2,4-dimethoxybenzyl)-N-(1,2,4-thiadiazol-5-yl)sulfamoyl)-5-fluorophenyl)amino)butyl)carbamate (15-04)

To the stirred solution of (S)-tert-butyl (4-aminobutyl)(2-((tert-butoxycarbonyl)amino)propyl) carbamate (15-03, 3.21 g, 9.31 mmol) in DMF (23 ml) were added DIEA (3.25 ml, 18.6 mmol) 5-chloro-N-(3,4-dimethylbenzyl)-2,4-difluoro-N-(1,2,4-thiadiazol-5-yl) benzenesulfonamide (Intermediate 3, 4.30 g, 9.31 mmol). The mixture was stirred at 50° C. overnight. The mixture was cooled to room temperature, concentrated and purified by chromatography (Isco CombiFlash system, 220 g RediSep silica gel gold column, and 0-100% EtOAc in hexane as eluent) to give the title compound as a solid. For C34H48ClFN6O8S2, LCMS m/z (M+H) calc'd: 787.26; found: 787.34.

(S)-4-((4-((2-aminopropyl)amino)butyl)amino)-5-chloro-2-fluoro-N-(1,2,4-thiadiazol-5-yl)benzenesulfonamide dihydrochloride (15-05)

To the stirred solution of (S)-tert-butyl (2-((tert-butoxycarbonyl)amino)propyl)(4-((2-chloro-4-(N-(2,4-dimethoxybenzyl)-N-(1,2,4-thiadiazol-5-yl)sulfamoyl)-5-fluorophenyl)amino)butyl)carbamate (15-04, 5.21 g, 6.62 mmol) in DCM (28 ml) was added TFA (51.0 ml, 662 mmol). The mixture was stirred at room temperature for about 1 h, then concentrated. To the residue was added MeOH (150 ml), mixed well. The resulting suspension was filtered. The filtrate was concentrated, and then purified by reverse HPLC in two runs (Isco CombiFlash system, using 415 g HP C18 Gold RediSepRf column, and 5-70% acetonitrile (with 0.05% TFA) in water (with 0.05% TFA). To the collected pure fractions was added HCl (1M in water) (13.2 ml, 13.2 mmol), mixed well and lyophilized to give the titled product as a solid. For C15H22ClFN6O2S2, LCMS m/z (M+H) calc'd: 437.09; found (M+H): 437.04. $^1$H NMR (500 MHz, CD$_3$OD): δ 8.209 (s, 1H); 7.670 (d, J=7.5 Hz, 1H); 6.606 (d, J=13.5 Hz, 1H); 3.754 (m, 1H); 3.350 (t, J=6.5 Hz, 2H); 3.32-3.31 (m, 1H, overlap with solvent peak); 3.27-3.23 (m, 1H); 3.171-3.117 (m, 2H); 1.890-1.830 (m, 2H); 1.780-1.720 (m, 2H); 1.450 (d, J=6.5 Hz, 3H).

Example 16: Additional Compounds

Using the chemistry and intermediates described herein, the compounds of Table 5 were prepared:

TABLE 5

| Exp No. | Structure | Name | LC/MS [M + H]+ |
|---|---|---|---|
| 16-01 | 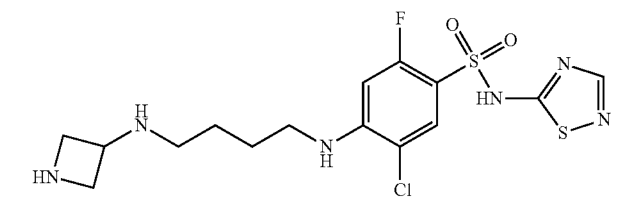 [SMILES: O=S(=O)(Nc1ncns1)c1cc(Cl)c(NCCCCNC2CNC2)cc1F] | 4-{[4-(azetidin-3-ylamino)-butyl]-amino}-5-chloro-2-fluoro-N-1,2,4-thiadiazol-5-ylbenzenesulfonamide | Calc. 435.1 Obs. 434.9 |
| 16-04 | 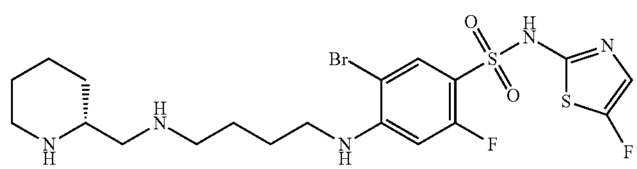 [SMILES: O=S(=O)(Nc1ncc(F)s1)c1cc(Br)c(NCCCCNC[C@H]2CCCCN2)cc1F] | 5-bromo-2-fluoro-N-(5-fluoro-1,3-thiazol-2-yl)-4-[(4-{[(2R)-piperidin-2-ylmethyl]amino}-butyl]amino]benzene-sulfonamide | Calc. 538.1 Obs. 538.2 |
| 16-05 | 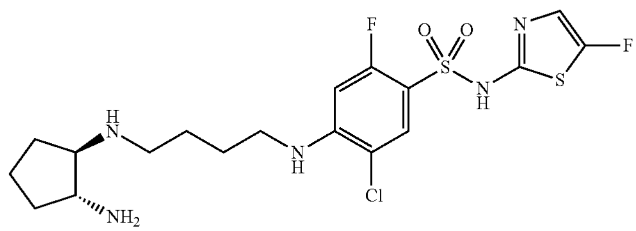 [SMILES: N[C@@H]1CCC[C@H]1NCCCCNc1cc(F)c(S(=O)(=O)Nc2ncc(F)s2)cc1Cl] | 4-[(4-{[(1R,2R)-2-aminocyclopentyl]-amino}-butyl)-amino]-5-chloro-2-fluoro-N-(5-fluoro-1,3-thiazol-2-yl)-benzene-sulfonamide | Calc. 480.1 Obs. 479.8 |
| 16-06 | 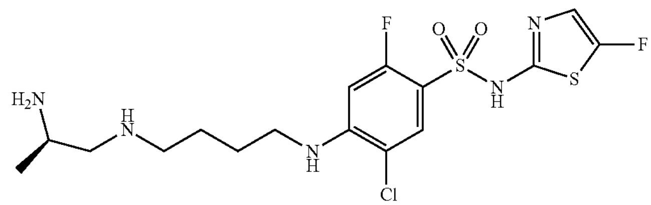 [SMILES: C[C@@H](N)CNCCCCNc1cc(F)c(S(=O)(=O)Nc2ncc(F)s2)cc1Cl] | 4-[(4-{[(1R,2R)-2-aminopropyl]amino}-butyl)amino]-5-chloro-2-fluoro-N-(5-fluoro-1,3-thiazol-2-yl)benzene-sulfonamide | Calc. 454.1 Obs. 453.9 |
| 16-08 | 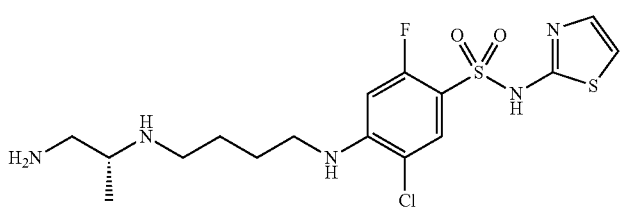 [SMILES: C[C@H](CN)NCCCCNc1cc(F)c(S(=O)(=O)Nc2nccs2)cc1Cl] | 4-[(4-{[(1R)-2-amino-1-methylethyl]-amino}butyl)-amino]-5-chloro-2-fluoro-N-1,3-thiazol-2-ylbenzenesulfonamide | Calc. 436.1 Obs. 435.9 |
| 16-09 | 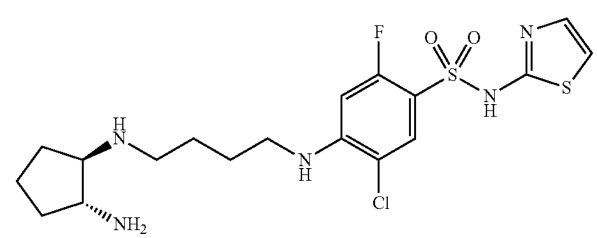 [SMILES: N[C@@H]1CCC[C@H]1NCCCCNc1cc(F)c(S(=O)(=O)Nc2nccs2)cc1Cl] | 4-[(4-{[(1R,2R)-2-aminocyclopentyl]-amino{butyl)-amino]-5-chloro-2-fluoro-N-1,3-thiazol-2-yl-benzenesulfonamide | Calc. 462.1 Obs. 461.9 |

TABLE 5-continued

| Exp No. | Structure | Name | LC/MS [M + H]+ |
|---|---|---|---|
| 16-12 | 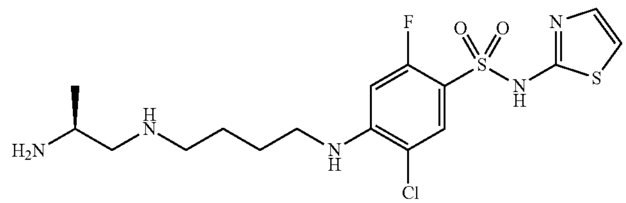 [SMILES: C[C@H](N)CNCCCCNc1cc(F)c(S(=O)(=O)Nc2nccs2)cc1Cl] | 4-[(4-{[(2S)-2-aminopropyl]-amino}butyl)amino]-5-chloro-2-fluoro-N-1,3-thiazol-2-yl-benzene-sulfonamide | Calc. 436.10 Obs. 435.86 |
| 16-13 | 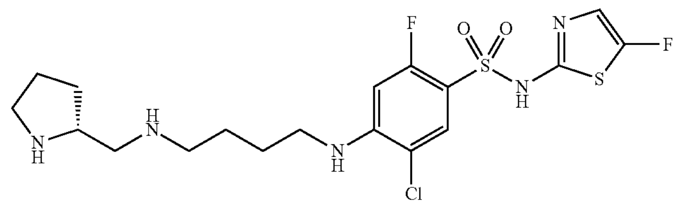 [SMILES: O=S(=O)(Nc1ncc(F)s1)c1cc(Cl)c(NCCCCNC[C@H]2CCCN2)cc1F] | 5-chloro-2-fluoro-N-(5-fluoro-1,3-thiazol-2-yl)-4-[(4-{[(2R)-pyrrolidin-2-yl-methyl]amino}-butyl)-amino]benzenesulfonamide | Calc'd 480.1 found 480.2 |
| 16-14 | 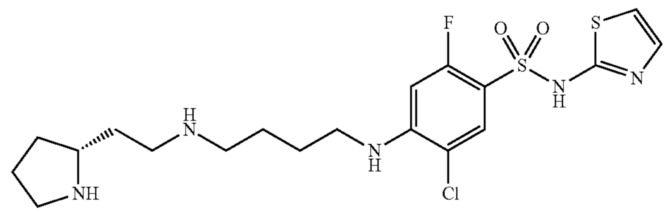 [SMILES: O=S(=O)(Nc1nccs1)c1cc(Cl)c(NCCCCNCC[C@H]2CCCN2)cc1F] | 5-chloro-2-fluoro-4-{[4-({2-[(2R)-pyrrolidin-2-yl]ethyl}-amino)-butyl]-amino}-N-1,3-thiazol-2-yl-benzenesulfonamide | Calc'd 476.1 found 476.2 |
| 16-15 | 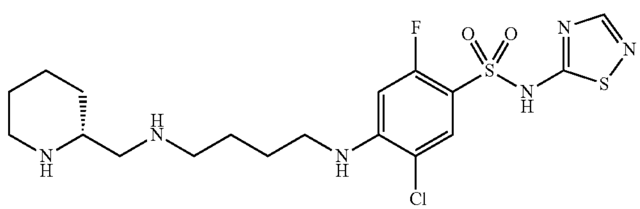 [SMILES: O=S(=O)(Nc1ncns1)c1cc(Cl)c(NCCCCNC[C@H]2CCCCN2)cc1F] | 5-chloro-2-fluoro-4-[(4-{[(2R)-piperidin-2-yl-methyl]amino}butyl)-amino]-N-1,2,4-thiadiazol-5-yl-benzenesulfonamide | Calc'd 477.1 found 477.2 |
| 16-16 | 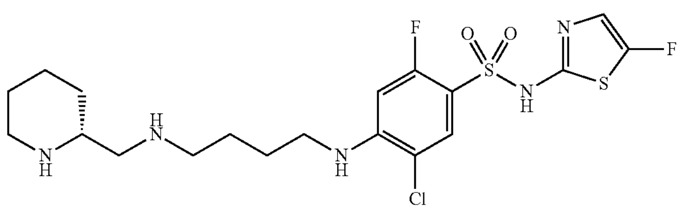 [SMILES: O=S(=O)(Nc1ncc(F)s1)c1cc(Cl)c(NCCCCNC[C@H]2CCCCN2)cc1F] | 5-chloro-2-fluoro-N-(5-fluoro-1,3-thiazol-2-yl)-4-[(4-{[(2R)-piperidin-2-yl-methyl]amino}butyl)-amino]benzenesulfonamide | Calc'd 494.1 found 494.1 |
| 16-17 | 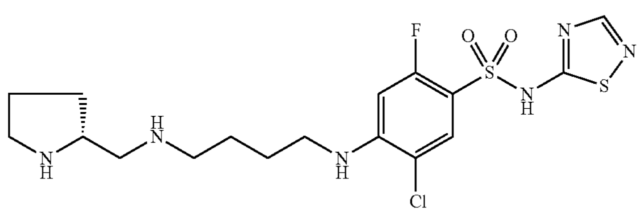 [SMILES: O=S(=O)(Nc1ncns1)c1cc(Cl)c(NCCCCNC[C@H]2CCCN2)cc1F] | 5-chloro-2-fluoro-4-[(4-{[(2R)-pyrrolidin-2-yl-methyl]amino}butyl)amino]-N-1,2,4-thiadiazol-5-yl-benzenesulfonamide | Calc'd 463.1 found 463.0 |
| 16-18 | 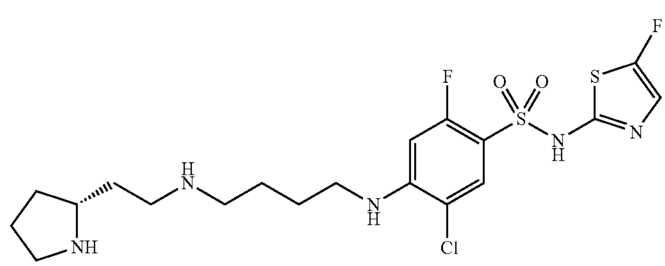 [SMILES: O=S(=O)(Nc1ncc(F)s1)c1cc(Cl)c(NCCCCNCC[C@H]2CCCN2)cc1F] | 5-chloro-2-fluoro-N-(5-fluoro-1,3-thiazol-2-yl)-4-{[4-({2-[(2R)-pyrrolidin-2yl]-ethyl}amino)butyl]-amino}benzenesulfonamide | Calc'd 494.1 found 494.0 |

TABLE 5-continued

| Exp No. | Structure | Name | LC/MS [M + H]+ |
|---|---|---|---|
| 16-19 | 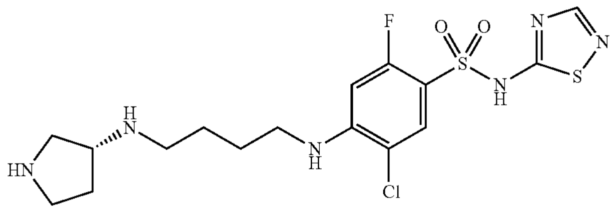 [SMILES: O=S(=O)(Nc1ncns1)c1cc(Cl)c(NCCCCN[C@@H]2CCNC2)cc1F] | 5-chloro-2-fluoro-4-({4-[(3R)-pyrrolidin-3-ylamino]-butyl}amino)-N-1,2,4-thiadiazol-5-ylbenzene-sulfonamide | Calc'd 449.1 found 448.9 |
| 16-20 | 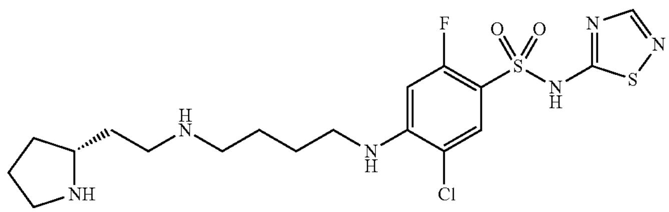 [SMILES: O=S(=O)(Nc1ncns1)c1cc(Cl)c(NCCCCNCC[C@H]2CCCN2)cc1F] | 5-chloro-2-fluoro-4-{[4-({2-[(2R)-pyrrolidin-2-yl]ethyl}-amino)butyl]amino}-N-1,2,4-thiadiazol-5-ylbenzene-sulfonamide | Calc'd 477.1 found 477.2 |
| 16-21 | 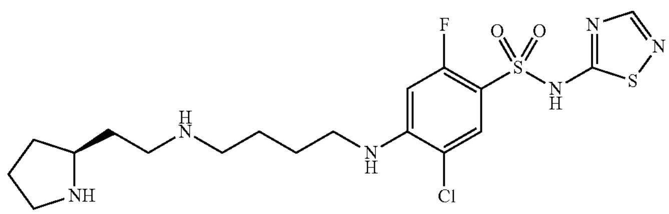 [SMILES: O=S(=O)(Nc1ncns1)c1cc(Cl)c(NCCCCNCC[C@@H]2CCCN2)cc1F] | 5-chloro-2-fluoro-4-{[4-({2-[(2S)-pyrrolidin-2-yl]ethyl}-amino)butyl]amino}-N-1,2,4-thiadiazol-5-ylbenzene-sulfonamide | Calc'd 477.1 found 477.2 |
| 16-22 | 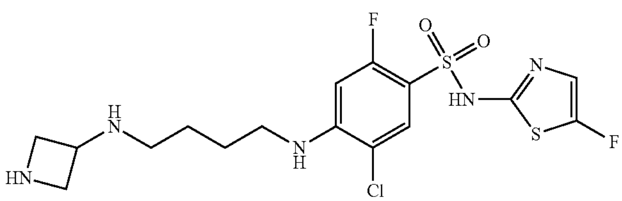 [SMILES: O=S(=O)(Nc1ncc(F)s1)c1cc(Cl)c(NCCCCNC2CNC2)cc1F] | 4-{[4-(azetidin-3-ylamino)-butyl]amino}-5-chloro-2-fluoro-N-(5-fluoro-1,3-thiazol-2-yl)benzene-sulfonamide | Calc'd 452.1 found 452.0 |
| 16-24 | 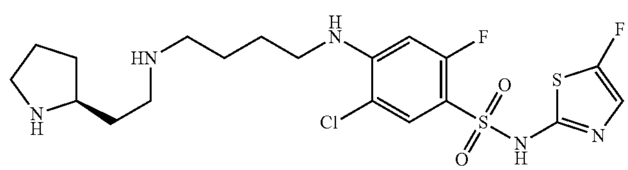 [SMILES: O=S(=O)(Nc1ncc(F)s1)c1cc(Cl)c(NCCCCNCC[C@@H]2CCCN2)cc1F] | 5-chloro-2-fluoro-N-(5-fluoro-1,3-thiazol-2-yl)-4-{[4-({2-[(2S)-pyrrolidin-2-yl]ethyl}amino)butyl]amino}benzenesulfonamide | Calc'd 494.1 found 494.0 |
| 16-25 | 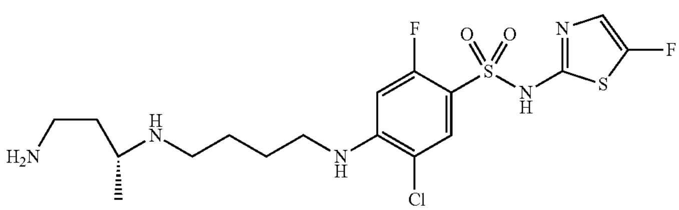 [SMILES: C[C@H](CCN)NCCCCNc1cc(F)c(S(=O)(=O)Nc2ncc(F)s2)cc1Cl] | 4-[(4-{[(1R)-3-amino-1-methylpropyl]amino}butyl)amino]-5-chloro-2-fluoro-N-(5-fluoro-1,3-thiazol-2-yl)-benzenesulfonamide | Calc'd 468.1 found 467.9 |
| 16-26 | 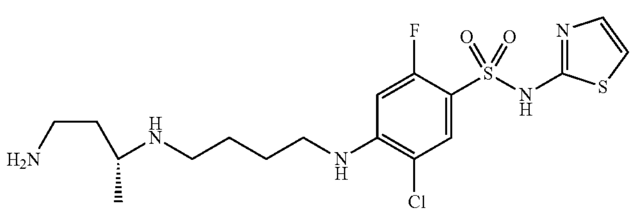 [SMILES: C[C@H](CCN)NCCCCNc1cc(F)c(S(=O)(=O)Nc2nccs2)cc1Cl] | 4-[(4-{[(1R)-3-amino-1-methylpropyl]amino}butyl)amino]-5-chloro-2-fluoro-N-1,3-thiazol-2-ylbenzene-sulfonamide | Calc'd 450.1 found 449.9 |

TABLE 5-continued

| Exp No. | Structure | Name | LC/MS [M + H]+ |
|---|---|---|---|
| 16-27 | 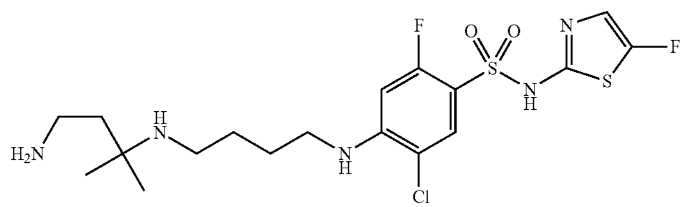 [SMILES: CC(C)(CCN)NCCCCNc1cc(F)c(S(=O)(=O)Nc2ncc(F)s2)cc1Cl] | 4-({4-[(3-amino-1,1-dimethylpropyl)amino]butyl}amino)-5-chloro-2-fluoro-N-(5-fluoro-1,3-thiazol-2-yl)-benzenesulfonamide | Calc'd 482.1 found 481.9 |
| 16-28 | 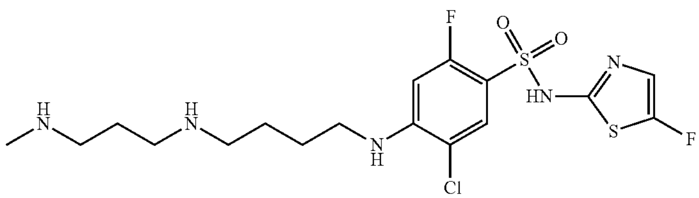 [SMILES: CNCCCNCCCCNc1cc(F)c(S(=O)(=O)Nc2ncc(F)s2)cc1Cl] | 5-chloro-2-fluoro-N-(5-fluoro-1,3-thiazol-2-yl)-4-[(4-{[3-(methylamino)-propyl]amino}butyl)amino]-benzenesulfonamide | Calc'd 468.1 found 468.1 |
| 16-29 | 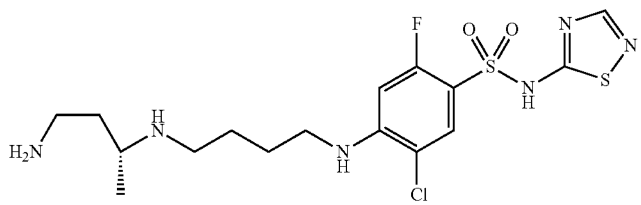 [SMILES: C[C@H](CCN)NCCCCNc1cc(F)c(S(=O)(=O)Nc2ncns2)cc1Cl] | 4-[(4-{[(1R)-3-amino-1-methylpropyl]amino}butyl)-amino]-5-chloro-2-fluoro-N-1,2,4-thiadiazol-5-yl-benzenesulfonamide | Calc'd 451.1 found 450.7 |
| 16-30 | 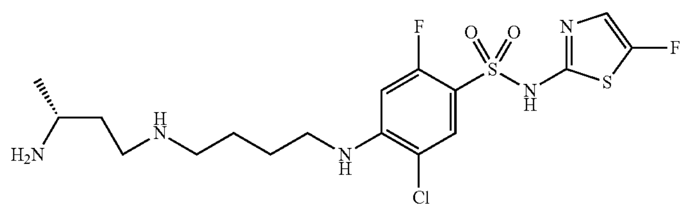 [SMILES: C[C@@H](N)CCNCCCCNc1cc(F)c(S(=O)(=O)Nc2ncc(F)s2)cc1Cl] | 4-[(4-{[(3R)-3-amino-butyl]amino}butyl)amino]-5-chloro-2-fluoro-N-(5-fluoro-1,3-thiazol-2-yl)benzene-sulfonamide | Calc'd 468.1 found 467.7 |
| 16-32 | 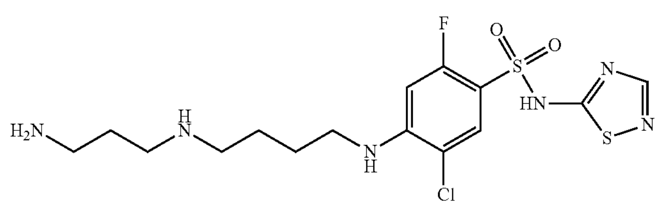 [SMILES: NCCCNCCCCNc1cc(F)c(S(=O)(=O)Nc2ncns2)cc1Cl] | 4-({4-[(3-aminopropyl)-amino]butyl}amino)-5-chloro-2-fluoro-N-1,2,4-thiadiazol-5-ylbenzene-sulfonamide | Calc'd 437.1 found 437.2 |
| 16-33 | 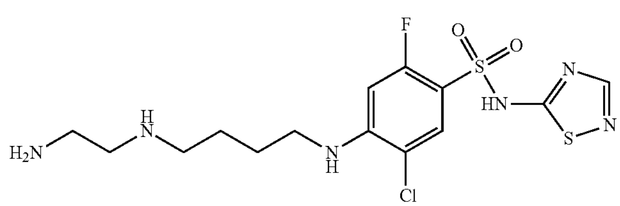 [SMILES: NCCNCCCCNc1cc(F)c(S(=O)(=O)Nc2ncns2)cc1Cl] | 4-({4-[(2-aminoethyl)-amino]butyl}amino)-5-chloro-2-fluoro-N-1,2,4-thiadiazol-5-ylbenzene-sulfonamide | Calc'd 423.1 found 423.1 |
| 16-34 | 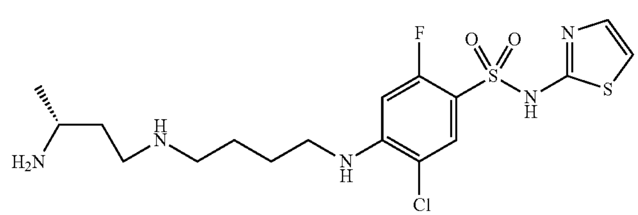 [SMILES: C[C@@H](N)CCNCCCCNc1cc(F)c(S(=O)(=O)Nc2nccs2)cc1Cl] | 4-[(4-{[(3R)-3-aminobutyl]-amino}butyl)amino]-5-chloro-2-fluoro-N-1,3-thiazol-2-ylbenzene-sulfonamide | Calc'd 450.1 found 450.0 |

TABLE 5-continued

| Exp No. | Structure | Name | LC/MS [M + H]+ |
|---|---|---|---|
| 16-35 | 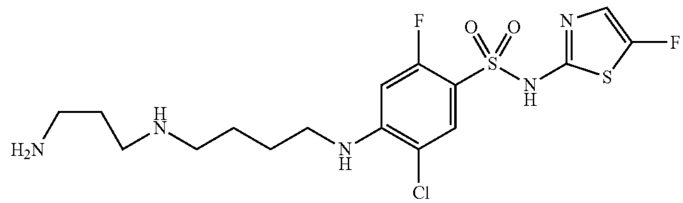 [SMILES: NCCCNCCCCNc1cc(F)c(S(=O)(=O)Nc2ncc(F)s2)cc1Cl] | 4-({4[(3-aminopropyl)amino]-butyl}amino)-5-chloro-2-fluoro-N-(5-fluoro-1,3-thiazol-2-yl)benzene-sulfonamide | Calc'd 454.1 found 453.9 |
| 16-36 | 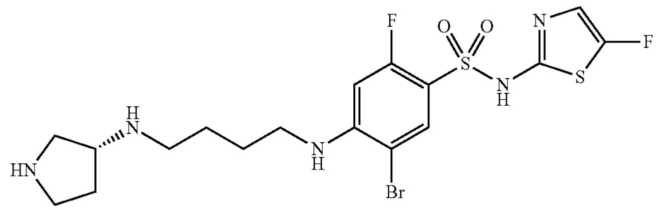 [SMILES: O=S(=O)(Nc1ncc(F)s1)c1cc(Br)c(NCCCCN[C@@H]2CCNC2)cc1F] | 5-bromo-2-fluoro-N-(5-fluoro-1,3-thiazol-2-yl)-4-({4-[(3R)-pyrrolidin-3-yl-amino]butyl}amino)benzene-sulfonamide | Calc'd 510.0, 512.0, found 509.9; 511.9 |
| 16-37 | 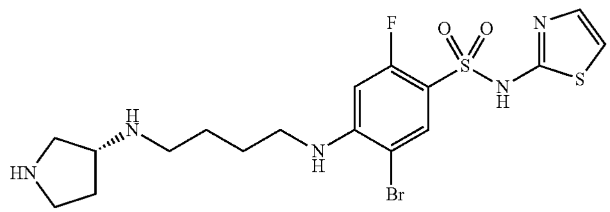 [SMILES: O=S(=O)(Nc1nccs1)c1cc(Br)c(NCCCCN[C@@H]2CCNC2)cc1F] | 5-bromo-2-fluoro-4-({4-[(3R)-pyrrolidin-3-ylamino]-butyl}amino)-N-1,3-thiazol-2-ylbenzenesulfonamide | Calc'd 492.1, 494.1, found 492.1; 494.1 |
| 16-41 | 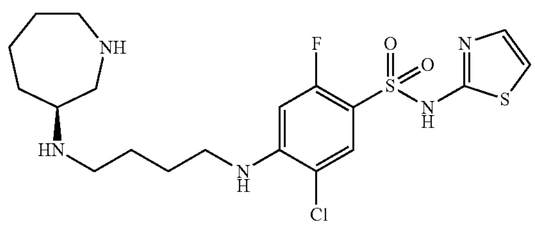 [SMILES: O=S(=O)(Nc1nccs1)c1cc(Cl)c(NCCCCN[C@H]2CCCCNC2)cc1F] | (S)-4-{[4-(azepan-3-ylamino)-butyl]amino}-5-chloro-2-fluoro-N-1,3-thiazol-2-yl-benzenesulfonamide | Calc'd 476.1 found 476.2 |
| 16-48 | 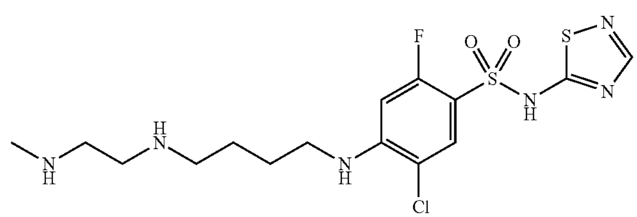 [SMILES: CNCCNCCCCNc1cc(F)c(S(=O)(=O)Nc2ncns2)cc1Cl] | 5-chloro-2-fluoro-4-[(4-{[2-(methylamino)ethyl]amino}-butyl)amino]-N-1,2,4-thiadiazol-5-ylbenzene-sulfonamide | Calc'd 437.1 found 437.2 |
| 16-49 | 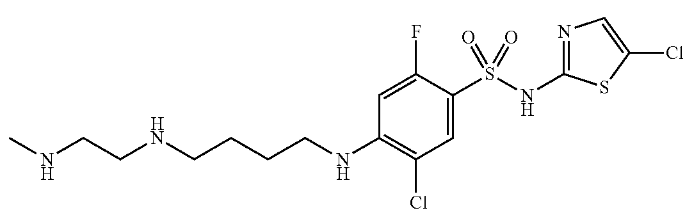 [SMILES: CNCCNCCCCNc1cc(F)c(S(=O)(=O)Nc2ncc(Cl)s2)cc1Cl] | 5-chloro-N-(5-chloro-1,3-thiazol-2-yl)-2-fluoro-4-[(4-{[2-(methylamino)ethyl]-amino}butyl)amino]benzene-sulfonamide | Calc'd 470.1 found 470.2 |
| 16-50 | 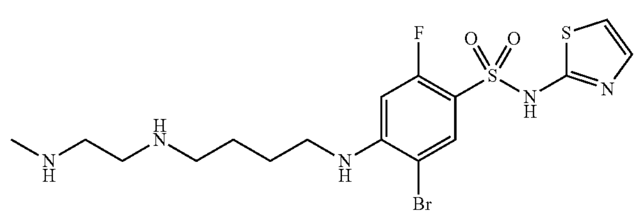 [SMILES: CNCCNCCCCNc1cc(F)c(S(=O)(=O)Nc2nccs2)cc1Br] | 5-bromo-2-fluoro-4-[(4-{[2-(methylamino)ethyl]amino}-butyl)amino]-N-1,3-thiazol-2-ylbenzenesulfonamide | Calc'd 480.0 found 480.2 |

TABLE 5-continued

| Exp No. | Structure | Name | LC/MS [M + H]+ |
|---|---|---|---|
| 16-55 | 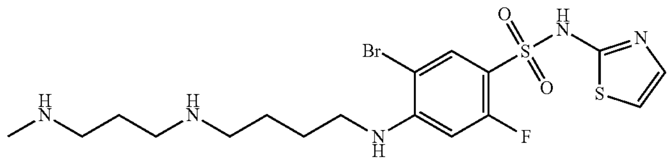 [SMILES: CNCCCNCCCCNc1cc(F)c(S(=O)(=O)Nc2nccs2)cc1Br] | 5-bromo-2-fluoro-4-[(4-{[3-(methylamino) propyl]amino}butyl) amino]-N-1,3-thiazol-2-ylbenzenesulfonamide | Calc'd 494.1 found 494.2 |
| 16-56 | 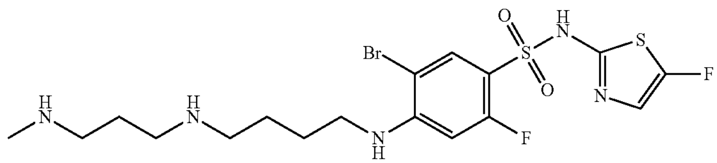 [SMILES: CNCCCNCCCCNc1cc(F)c(S(=O)(=O)Nc2ncc(F)s2)cc1Br] | 5-bromo-2-fluoro-N-(5-fluoro-1,3-thiazol-2-yl)-4-[(4-{[3-(methylamino)-propyl]amino}butyl)amino]-benzenesulfonamide | Calc'd 512.1 found 512.2 |
| 16-57 | 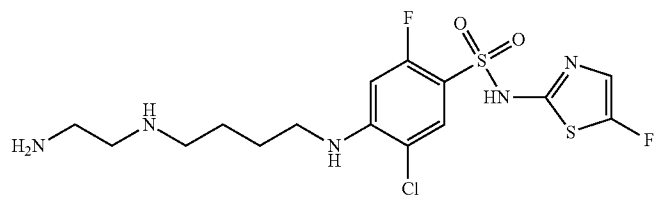 [SMILES: NCCNCCCCNc1cc(F)c(S(=O)(=O)Nc2ncc(F)s2)cc1Cl] | 4-({4-[(2-aminoethyl)-amino]butyl}amino)-5-chloro-2-fluoro-N-(5-fluoro-1,3-thiazol-2-yl)benzene-sulfonamide | Calc'd 440.1 found 440.0 |
| 16-58 | 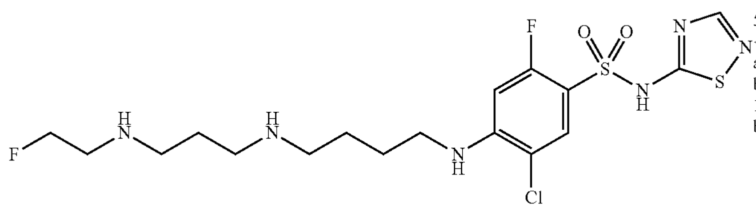 [SMILES: O=S(=O)(Nc1ncns1)c1cc(Cl)c(NCCCCNCCCNCCF)cc1F] | 5-chloro-2-fluoro-4-{[4-({3-[(2-fluoroethyl)amino]-propyl}amino) butyl]amino}-N-1,2,4-thiadiazol-5-yl-benzenesulfonamide | Calc'd 484.0 found 484.3 |
| 16-59 | 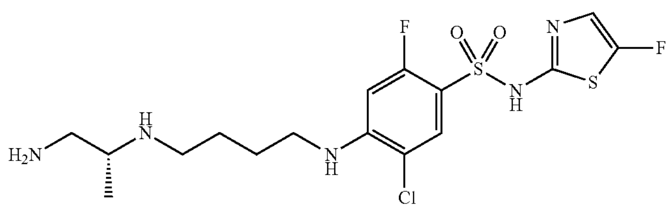 [SMILES: C[C@H](CN)NCCCCNc1cc(F)c(S(=O)(=O)Nc2ncc(F)s2)cc1Cl] | 4-[(4-{[(1R)-2-amino-1-methylethyl]amino} butyl)-amino]-5-chloro-2-fluoro-N-(5-fluoro-1,3-thiazol-2-yl)-benzenesulfonamide | Calc'd 454.1 found 453.9 |
| 16-60 | 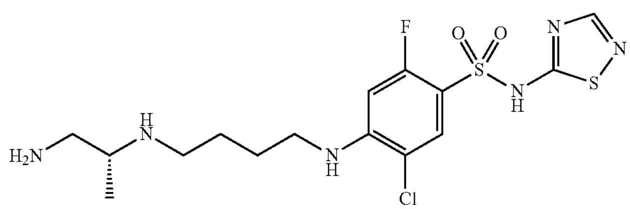 [SMILES: C[C@H](CN)NCCCCNc1cc(F)c(S(=O)(=O)Nc2ncns2)cc1Cl] | 4-[(4-{[(1R)-2-amino-1-methylethyl]amino} butyl)-amino]-5-chloro-2-fluoro-N-1,2,4-thiadiazol-5-yl-benzenesulfonamide | Calc'd 437.1 found 436.9 |
| 16-61 | 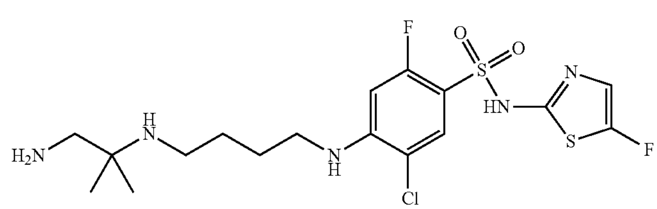 [SMILES: CC(C)(CN)NCCCCNc1cc(F)c(S(=O)(=O)Nc2ncc(F)s2)cc1Cl] | 4-({4-[(2-amino-1,1-dimethylethyl)amino] butyl}amino)-5-chloro-2-fluoro-N-(5-fluoro-1,3-thiazol-2-yl)benzenesulfonamide | Calc'd 468.1 found 468.0 |

TABLE 5-continued

| Exp No. | Structure | Name | LC/MS [M + H]+ |
|---|---|---|---|
| 16-62 | 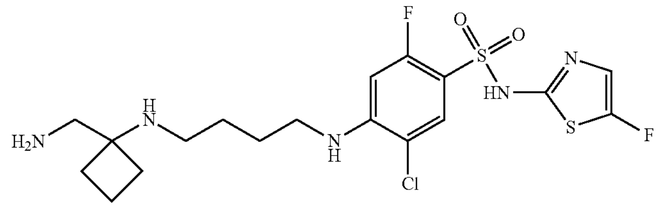 [SMILES: NCC1(NCCCCNc2cc(F)c(S(=O)(=O)Nc3ncc(F)s3)cc2Cl)CCC1] | 4-[(4-{[1-(aminomethyl)cyclobutyl]amino}butyl)amino]-5-chloro-2-fluoro-N-(5-fluoro-1,3-thiazol-2-yl)benzenesulfonamide | Calc'd 480.1 found 480.0 |
| 16-63 | 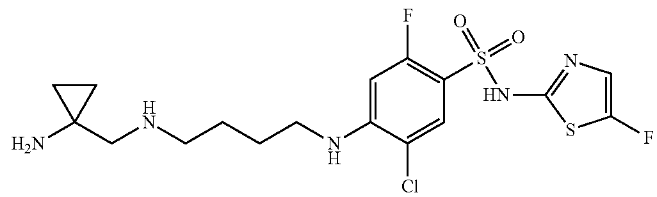 [SMILES: NC1(CNCCCCNc2cc(F)c(S(=O)(=O)Nc3ncc(F)s3)cc2Cl)CC1] | 4-[(4-{[(1-aminocyclopropyl)methyl]amino}butyl)amino]-5-chloro-2-fluoro-N-(5-fluoro-1,3-thiazol-2-yl)benzenesulfonamide | Calc'd 466.1 found 465.9 |
| 16-64 | 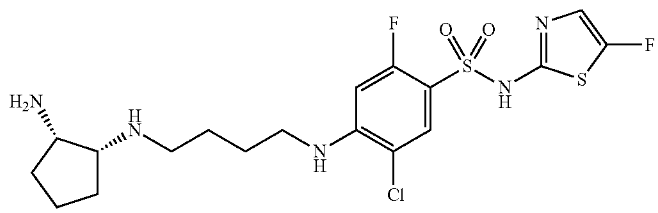 [SMILES: N[C@H]1CCC[C@H]1NCCCCNc1cc(F)c(S(=O)(=O)Nc2ncc(F)s2)cc1Cl] | 4-[(4-{[(1R,2S)-2-aminocyclopentyl]amino}butyl)amino]-5-chloro-2-fluoro-N-(5-fluoro-1,3-thiazol-2-yl)benzenesulfonamide | Calc'd 480.1 found 480.0 |
| 16-65 | 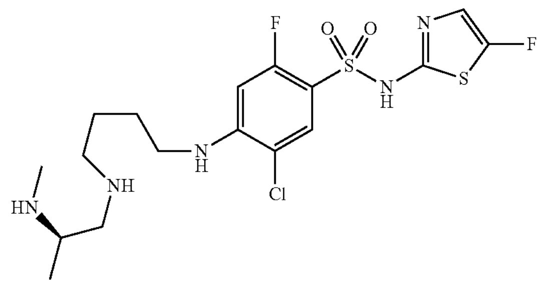 [SMILES: CN[C@H](C)CNCCCCNc1cc(F)c(S(=O)(=O)Nc2ncc(F)s2)cc1Cl] | 5-chloro-2-fluoro-N-(5-fluoro-1,3-thiazol-2-yl)-4-[(4-{[(2R)-2-(methylamino)propyl]amino}butyl)amino]benzenesulfonamide | Calc'd 468.1 found 468.0 |
| 16-66 | 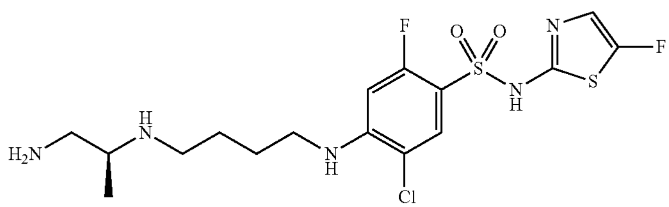 [SMILES: C[C@@H](CN)NCCCCNc1cc(F)c(S(=O)(=O)Nc2ncc(F)s2)cc1Cl] | 4-[(4-{[(1S)-2-amino-1-methylethyl]amino}butyl)amino]-5-chloro-2-fluoro-N-(5-fluoro-1,3-thiazol-2-yl)benzenesulfonamide | Calc'd 454.1 found 454.0 |
| 16-67 | 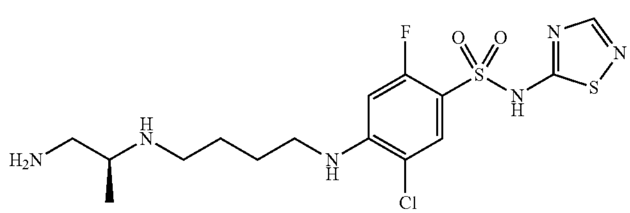 [SMILES: C[C@@H](CN)NCCCCNc1cc(F)c(S(=O)(=O)Nc2ncns2)cc1Cl] | 4-[(4-{[(1S)-2-amino-1-methylethyl]amino}butyl)amino]-5-chloro-2-fluoro-N-1,2,4-thiadiazol-5-ylbenzenesulfonamide | Calc'd 437.1 found 437.0 |
| 16-68 | 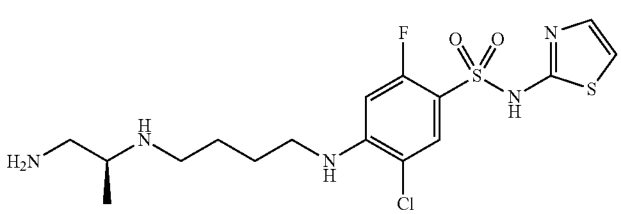 [SMILES: C[C@@H](CN)NCCCCNc1cc(F)c(S(=O)(=O)Nc2nccs2)cc1Cl] | 4-[(4-{[(1S)-2-amino-1-methylethyl]amino}butyl)amino]-5-chloro-2-fluoro-N-1,3-thiazol-2-ylbenzenesulfonamide | Calc'd 436.1 found 436.0 |

TABLE 5-continued

| Exp No. | Structure | Name | LC/MS [M + H]+ |
|---|---|---|---|
| 16-69 | 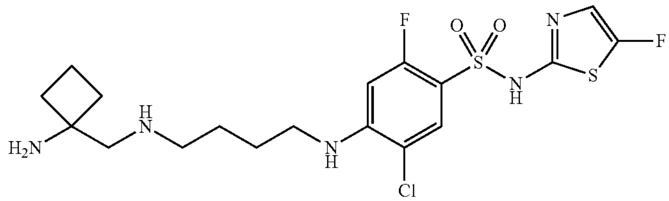 [SMILES: NC1(CNCCCCNc2cc(F)c(S(=O)(=O)Nc3ncc(F)s3)cc2Cl)CCC1] | 4-[(4-{[(1-aminocyclobutyl)methyl]amino}butyl)amino]-5-chloro-2-fluoro-N-(5-fluoro-1,3-thiazol-2-yl)benzenesulfonamide | Calc'd 480.1 found 480.2 |
| 16-70 | 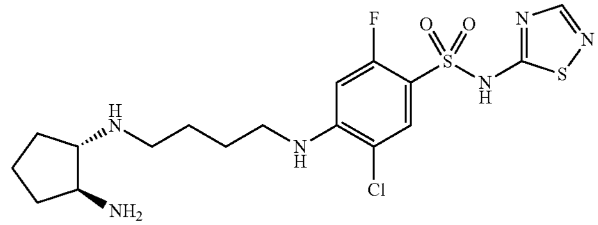 [SMILES: N[C@H]1CCC[C@@H]1NCCCCNc1cc(F)c(S(=O)(=O)Nc2ncns2)cc1Cl] | 4-[(4-{[(1S,2S)-2-aminocyclopentyl]amino}butyl)amino]-5-chloro-2-fluoro-N-1,2,4-thiadiazol-5-ylbenzenesulfonamide | Calc'd 463.1 found 462.9 |
| 16-71 | 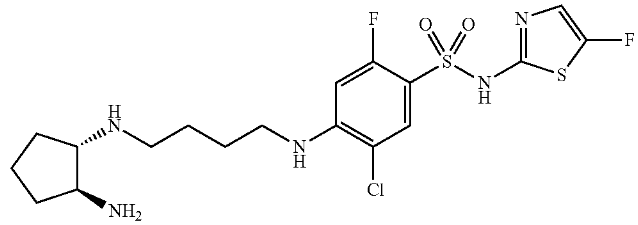 [SMILES: N[C@H]1CCC[C@@H]1NCCCCNc1cc(F)c(S(=O)(=O)Nc2ncc(F)s2)cc1Cl] | 4-[(4-{[(1S,2S)-2-aminocyclopentyl]amino}butyl)amino]-5-chloro-2-fluoro-N-(5-fluoro-1,3-thiazol-2-yl)benzenesulfonamide | Calc'd 480.1 found 480.0 |
| 16-72 | 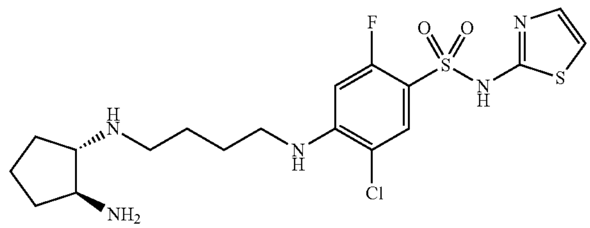 [SMILES: N[C@H]1CCC[C@@H]1NCCCCNc1cc(F)c(S(=O)(=O)Nc2nccs2)cc1Cl] | 4-[(4-{[(1S,2S)-2-aminocyclopentyl]amino}butyl)amino]-5-chloro-2-fluoro-N-1,3-thiazol-2-ylbenzenesulfonamide | Calc'd 462.1 found 461.9 |
| 16-73 | 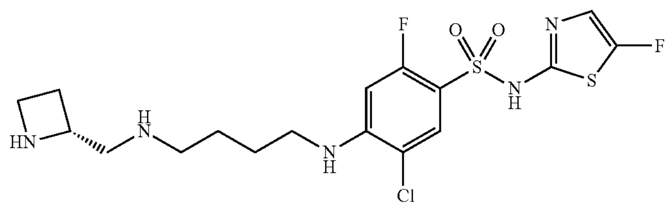 [SMILES: O=S(=O)(Nc1ncc(F)s1)c1cc(Cl)c(NCCCCNC[C@H]2CCN2)cc1F] | 4-[(4-{[(2R)-azetidin-2-ylmethyl]amino}butyl)amino]-5-chloro-2-fluoro-N-(5-fluoro-1,3-thiazol-2-yl)benzenesulfonamide | Calc'd 466.1 found 466.2 |
| 16-74 | 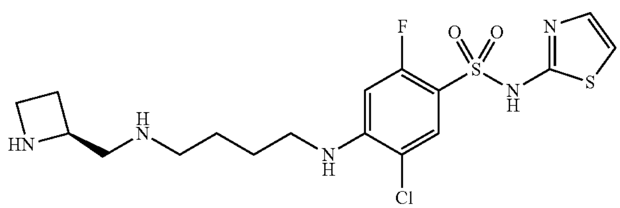 [SMILES: O=S(=O)(Nc1nccs1)c1cc(Cl)c(NCCCCNC[C@@H]2CCN2)cc1F] | 4-[(4-{[(2S)-azetidin-2-ylmethyl]amino}butyl)amino]-5-chloro-2-fluoro-N-1,3-thiazol-2-ylbenzenesulfonamide | Calc'd 448.1 found 448.2 |
| 16-75 | 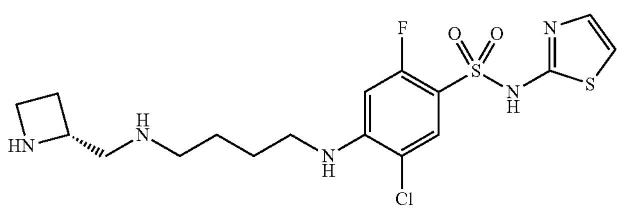 [SMILES: O=S(=O)(Nc1nccs1)c1cc(Cl)c(NCCCCNC[C@H]2CCN2)cc1F] | 4-[(4-{[(2R)-azetidin-2-ylmethyl]amino}butyl)amino]-5-chloro-2-fluoro-N-1,3-thiazol-2-ylbenzenesulfonamide | Calc'd 448.1 found 448.2 |

TABLE 5-continued

| Exp No. | Structure | Name | LC/MS [M + H]+ |
|---|---|---|---|
| 16-76 | 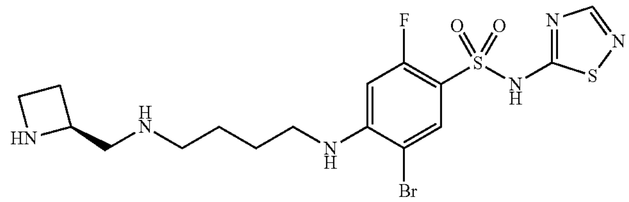 [SMILES: O=S(=O)(Nc1ncns1)c1cc(Br)c(NCCCCNC[C@@H]2CCN2)cc1F] | 4-[(4-{[(2S)-azetidin-2-ylmethyl]amino}butyl)amino]-5-bromo-2-fluoro-N-1,2,4-thiadiazol-5-ylbenzenesulfonamide | Calc'd 493.0 found 493.1/495.1 |
| 16-77 | 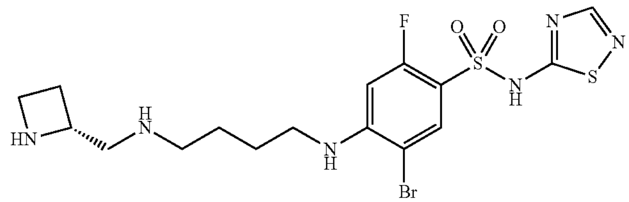 [SMILES: O=S(=O)(Nc1ncns1)c1cc(Br)c(NCCCCNC[C@H]2CCN2)cc1F] | 4-[(4-{[(2R)-azetidin-2-ylmethyl]amino}butyl)amino]-5-bromo-2-fluoro-N-1,2,4-thiadiazol-5-ylbenzenesulfonamide | Calc'd 493.0 found 493.1/495.1 |
| 16-78 | 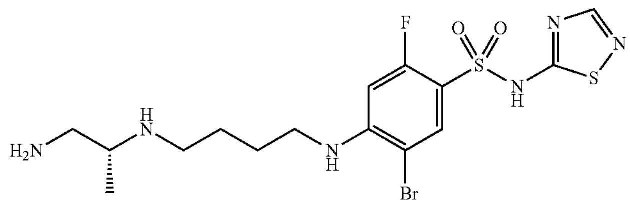 | 4-[(4-{[(1R)-2-amino-1-methylethyl]amino}butyl)amino]-5-bromo-2-fluoro-N-1,2,4-thiadiazol-5-ylbenzenesulfonamide | Calc'd 481.0 found 480.9/482.9 |
| 16-79 | 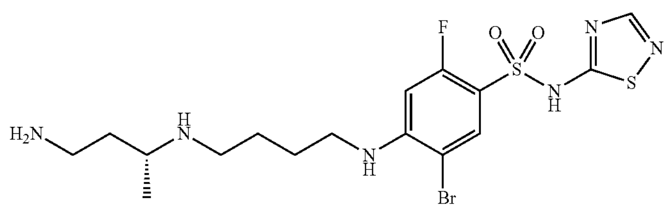 [SMILES: C[C@H](CCN)NCCCCNc1cc(F)c(S(=O)(=O)Nc2ncns2)cc1Br] | 4-[4-[[(1R)-3-amino-1-methyl-propyl]amino]butylamino]-5-bromo-2-fluoro-N-(1,2,4-thiadiazol-5-yl)benzenesulfonamide | Calc'd 495.06 found 494.99 |
| 16-80 | 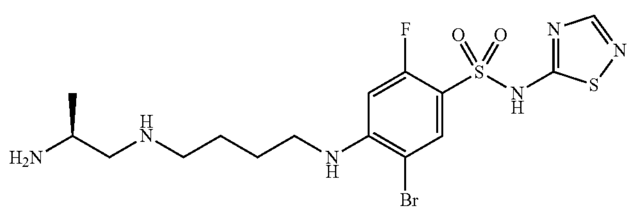 [SMILES: C[C@H](N)CNCCCCNc1cc(F)c(S(=O)(=O)Nc2ncns2)cc1Br] | 4-[4-[[(2S)-2-aminopropyl]amino]butylamino]-5-bromo-2-fluoro-N-(1,2,4-thiadiazol-5-yl)benzenesulfonamide | Calc'd 481.04 found 481.00 |
| 16-81 | 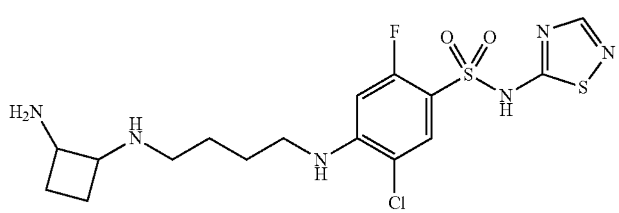 [SMILES: NC1CCC1NCCCCNc1cc(F)c(S(=O)(=O)Nc2ncns2)cc1Cl] | 4-[4-[(2-aminocyclobutyl)amino]butylamino]-5-chloro-2-fluoro-N-(1,2,4-thiadiazol-5-yl)benzenesulfonamide | Calc'd 449.09 found 448.98 |
| 16-82 | 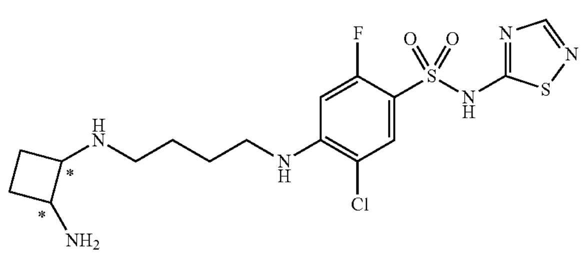 [SMILES: NC1CCC1NCCCCNc1cc(F)c(S(=O)(=O)Nc2ncns2)cc1Cl] | Enantiomer A: 4-[4-[[(1S,2S) or (1R,2R)-2-aminocyclobutyl]amino]butylamino]-5-chloro-2-fluoro-N-(1,2,4-thiadiazol-5-yl)benzenesulfonamide | Calc'd 449.09 found 449.11 |

TABLE 5-continued

| Exp No. | Structure | Name | LC/MS [M + H]+ |
|---|---|---|---|
| 16-83 | 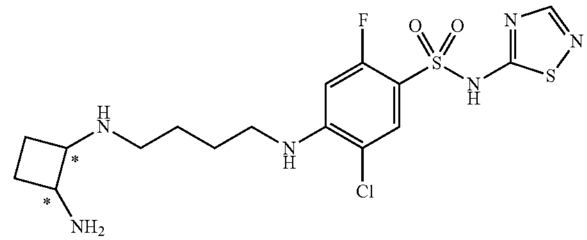 [SMILES: NC1CCC1NCCCCNc1cc(F)c(S(=O)(=O)Nc2ncns2)cc1Cl] | Enantiomer B: 4-[4-[[(1R,2R) or (1S,2S)-2-aminocyclobutyl]amino]butylamino]-5-chloro-2-fluoro-N-(1,2,4-thiadiazol-5-yl)benzenesulfonamide | Calc'd 449.09 found 449.08 |
| 16-84 | 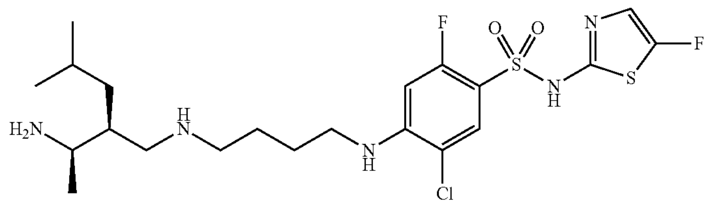 [SMILES: CC(C)C[C@@H](CNCCCCNc1cc(F)c(S(=O)(=O)Nc2ncc(F)s2)cc1Cl)[C@@H](C)N] | 4-((4-(((S)-2-((R)-1-aminoethyl)-4-methylpentyl)-amino)butyl)amino)-5-chloro-2-fluoro-N-(5-fluorothiazol-2-yl)benzenesulfonamide | Calc'd 524.2 found 524.2 |
| 16-85 | 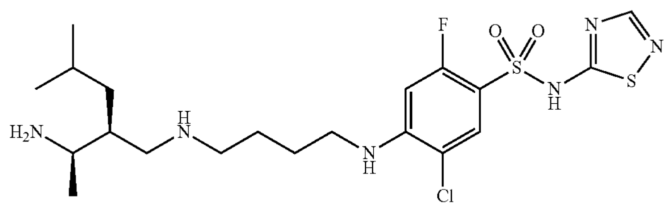 [SMILES: CC(C)C[C@@H](CNCCCCNc1cc(F)c(S(=O)(=O)Nc2ncns2)cc1Cl)[C@@H](C)N] | 4-((4-(((S)-2-((R)-1-aminoethyl)-4-methylpentyl)-amino)butyl)amino)-5-chloro-2-fluoro-N-(1,2,4-thiadiazol-5-yl)benzenesulfonamide | Calc'd 507.2 found 507.2 |
| 16-86 | 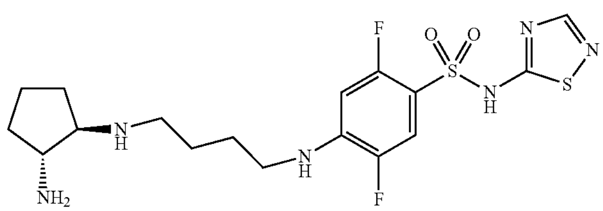 [SMILES: N[C@@H]1CCC[C@H]1NCCCCNc1cc(F)c(S(=O)(=O)Nc2ncns2)cc1F] | 4-[4-[[(1R,2R)-2-aminocyclopentyl]amino]butylamino]-2,5-difluoro-N-(1,2,4-thiadiazol-5-yl)benzenesulfonamide | Calc'd 447.14 found 446.96 |
| 16-88 | 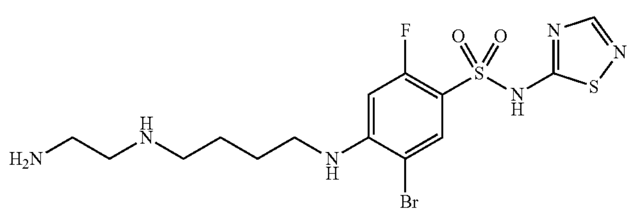 [SMILES: NCCNCCCCNc1cc(F)c(S(=O)(=O)Nc2ncns2)cc1Br] | 4-[4-(2-aminoethylamino)butylamino]-5-bromo-2-fluoro-N-(1,2,4-thiadiazol-5-yl)benzenesulfonamide | Calc'd 466.026 found 467.034 |
| 16-89 | 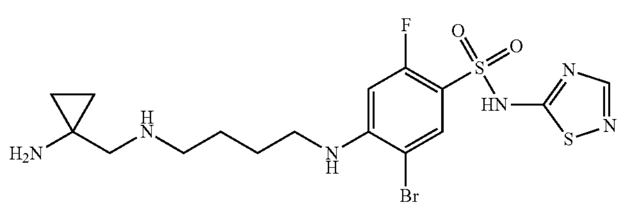 [SMILES: NC1(CNCCCCNc2cc(F)c(S(=O)(=O)Nc3ncns3)cc2Br)CC1] | 4-[4-[(1-aminocyclopropyl)methylamino]butylamino]-5-bromo-2-fluoro-N-(1,2,4-thiadiazol-5-yl)benzenesulfonamide | Calc'd 493.04 found 493.05 |
| 16-90 | 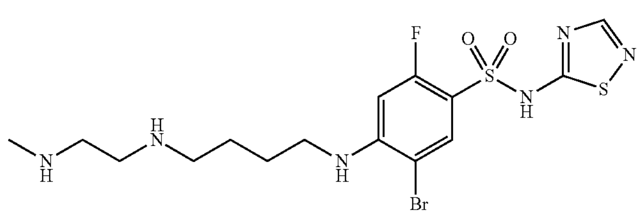 [SMILES: CNCCNCCCCNc1cc(F)c(S(=O)(=O)Nc2ncns2)cc1Br] | 5-bromo-2-fluoro-4-[4-[2-(methylamino)ethylamino]butylamino]-N-(1,2,4-thiadiazol-5-yl)benzenesulfonamide | Calc'd 481.04 found 481.05 |

TABLE 5-continued

| Exp No. | Structure | Name | LC/MS [M + H]+ |
|---|---|---|---|
| 16-91 | 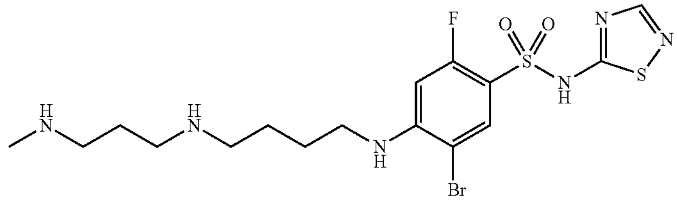 [SMILES: CNCCCNCCCCNc1cc(F)c(S(=O)(=O)Nc2ncns2)cc1Br] | 5-bromo-2-fluoro-4-[4-[3-(methylamino)propylamino]butylamino]-N-(1,2,4-thiadiazol-5-yl)benzenesulfonamide | Calc'd 495.06 found 495.06 |
| 16-92 | 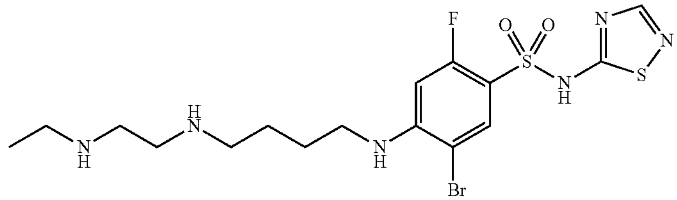 [SMILES: CCNCCNCCCCNc1cc(F)c(S(=O)(=O)Nc2ncns2)cc1Br] | 5-bromo-4-[4-[2-(ethylamino)ethylamino]butylamino]-2-fluoro-N-(1,2,4-thiadiazol-5-yl)benzenesulfonamide | Calc'd 495.06 found 495.06 |
| 16-93 | 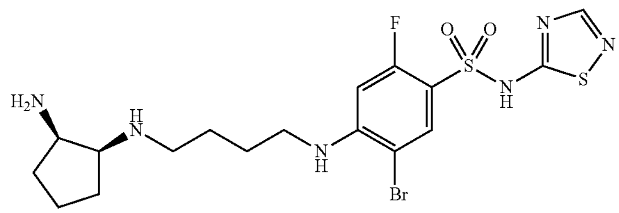 [SMILES: N[C@@H]1CCC[C@@H]1NCCCCNc1cc(F)c(S(=O)(=O)Nc2ncns2)cc1Br] | 4-[4-[[(1S,2R)-2-aminocyclopentyl]amino]butylamino]-5-bromo-2-fluoro-N-(1,2,4-thiadiazol-5-yl)benzenesulfonamide | Calc'd 507.06 found 507.06 |
| 16-94 | 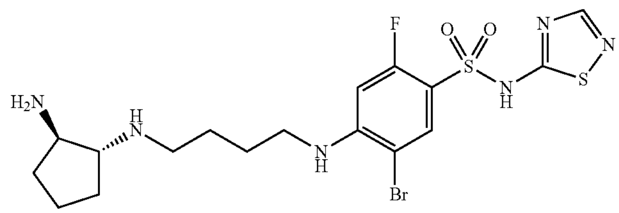 [SMILES: N[C@@H]1CCC[C@H]1NCCCCNc1cc(F)c(S(=O)(=O)Nc2ncns2)cc1Br] | 4-[4-[[(1R,2R)-2-aminocyclopentyl]amino]butylamino]-5-bromo-2-fluoro-N-(1,2,4-thiadiazol-5-yl)benzenesulfonamide | Calc'd 507.06 found 507.06 |
| 16-95 | 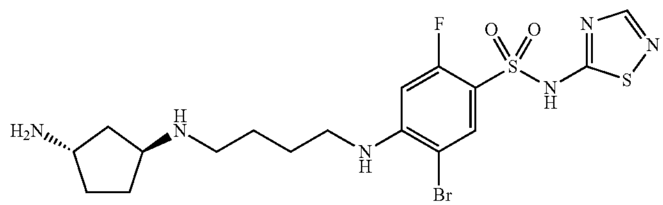 [SMILES: N[C@H]1CC[C@H](NCCCCNc2cc(F)c(S(=O)(=O)Nc3ncns3)cc2Br)C1] | 4-[4-[[(1S,3S)-3-aminocyclopentyl]amino]butylamino]-5-bromo-2-fluoro-N-(1,2,4-thiadiazol-5-yl)benzenesulfonamide | Calc'd 507.06 found 507.06 |
| 16-96 | 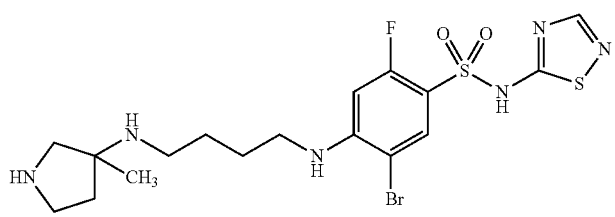 [SMILES: CC1(NCCCCNc2cc(F)c(S(=O)(=O)Nc3ncns3)cc2Br)CCNC1] | 5-bromo-2-fluoro-4-[4-[(3-methylpyrrolidin-3-yl)amino]butylamino]-N-(1,2,4-thiadiazol-5-yl)benzenesulfonamide | Calc'd 507.06 found 507.06 |
| 16-97 | 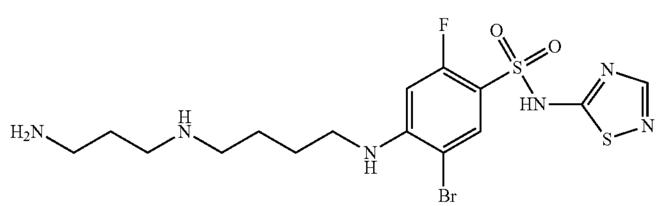 [SMILES: NCCCNCCCCNc1cc(F)c(S(=O)(=O)Nc2ncns2)cc1Br] | 4-[4-(3-aminopropylamino)butylamino]-5-bromo-2-fluoro-N-(1,2,4-thiadiazol-5-yl)benzenesulfonamide | Calc'd 481.04 found 481.05 |

TABLE 5-continued

| Exp No. | Structure | Name | LC/MS [M + H]+ |
|---|---|---|---|
| 16-98 | 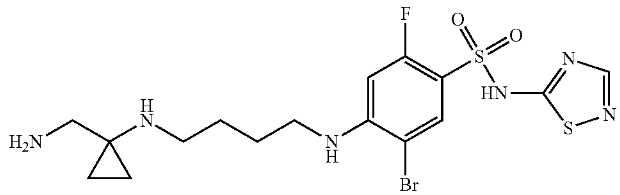 [SMILES: NCC1(NCCCCNc2cc(F)c(S(=O)(=O)Nc3ncns3)cc2Br)CC1] | 4-[4-[[1-(aminomethyl) cyclopropyl]amino] butylamino]-5-bromo-2-fluoro-N-(1,2,4-thiadiazol-5-yl) benzenesulfonamide | Calc'd 493.04 found 493.05 |
| 16-99 | 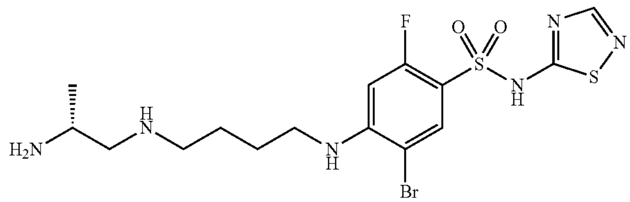 [SMILES: C[C@@H](N)CNCCCCNc1cc(F)c(S(=O)(=O)Nc2ncns2)cc1Br] | 4-[4-[[(2R)-2-aminopropyl] amino]butylamino]-5-bromo-2-fluoro-N-(1,2,4-thiadiazol-5-yl)benzenesulfonamide | Calc'd 481.04 found 481.05 |
| 16-100 | 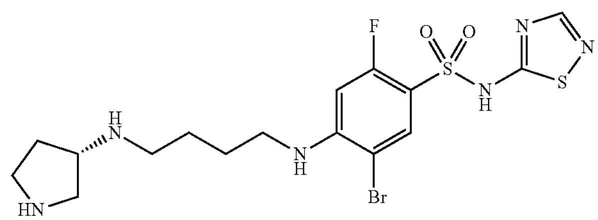 [SMILES: O=S(=O)(Nc1ncns1)c1cc(Br)c(NCCCCN[C@H]2CCNC2)cc1F] | (S)-5-bromo-2-fluoro-4-((4-(pyrrolidin-3-ylamino)butyl)amino)-N-(1,2,4-thiadiazol-5-yl)benzenesulfonamide | Calc'd 493.04 found 493.05 |

It will be appreciated that where enantiomeric separation is performed and pure enantiomers are isolated, but the absolute configuration of the separated enantiomers is not determined, for example, the pair of enantiomers from the table above, Ex 16-82 (labeled "Enantiomer A") and Ex 16-83 (labeled "Enantiomer B"), is the preparation and isolation of the pure separated enantiomers 4-[4-[[(1S,2S)-2-aminocyclobutyl]amino]-butylamino]-5-chloro-2-fluoro-N-(1,2,4-thiadiazol-5-yl)benzenesulfonamide and 4-[4-[[(1R,2R)-2-aminocyclobutyl]amino]-butylamino]-5-chloro-2-fluoro-N-(1,2,4-thiadiazol-5-yl) benzenesulfonamide, and thus enables the preparation of each of the enantiomers individually and mixtures of the two.

Synthesis of Intermediates Useful in Preparing Compounds of the Invention

Intermediate 1: 5-chloro-N-(2,4-dimethoxybenzyl)-2,4-difluoro-N-(thiazol-2-yl)benzene sulfonamide

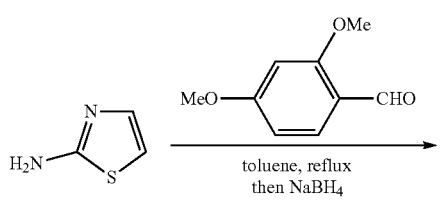

Intermediate 1

Step 1: Preparation of N-(2,4-dimethoxybenzyl)thiazol-2-amine (A-1)

A mixture of thiazol-2-amine (100 g, 1 mol) and 2,4-dimethoxybenzaldehyde (151 g, 0.91 mol) in 2 L of toluene was refluxed for 8 h with Dean-Stark apparatus to remove water. The mixture was cooled and the solvent was evaporated in vacuo. To the residue was added 3 L of MeOH and the resulting mixture was cooled to 0° C. NaBH$_4$ (151 g, 4 mol) was added carefully in portions. The mixture was then warmed to room temperature and stirred for 4 h. The mixture was quenched with water, then MeOH was evaporated in vacuo. The water layer was extracted with EtOAc and the combined organic layers were dried over Na$_2$SO$_4$, filtered and concentrated. The residue was purified by column chromatography on silica gel (PE:EtOAc=5:1 to 2:1) to give the title compound. $^1$H NMR (400 MHz, CD$_3$OD) δ 7.16 (d, J=8.4 Hz, 1H), 6.97 (d, J=4.0 Hz, 1H), 6.50-6.52 (m, 2H), 6.44 (dd, J=8.0, 2.0 Hz, 1H), 4.35 (s, 2H), 3.81 (s, 3H), 3.76 (s, 3H).

Step 2: Preparation of 5-chloro-N-(2,4-dimethoxybenzyl)-2,4-difluoro-N-(thiazol-2-yl)benzene sulfonamide (Intermediate 1)

Under an atmosphere of nitrogen, N-(2,4-dimethoxybenzyl)thiazol-2-amine A-1 (5 g, 20 mmol) was dissolved in THF (100 mL) and cooled to −78° C. LiHMDS (24 mL, 24 mmol) was added dropwise keeping the temperature below −60° C. After 30 minutes, the cooling bath was removed and the reaction was warmed to room temperature for a further 30 minutes then cooled back to −78° C. A solution of 5-chloro-2,4-difluorobenzene-1-sulfonyl chloride (5.54 g, 22.4 mmol) in THF (10 mL) was added dropwise keeping the temperature below −60° C. and the reaction mixture was warmed to room temperature. Saturated aqueous ammonium chloride solution (50 mL) was added followed by water to dissolve the solid which had precipitated out. The aqueous layer was extracted with ethyl acetate (50 mL) and the organic extracts was dried over Na$_2$SO$_4$, filtered and concentrated. The residue was purified by column chromatography on silica gel (PE:EtOAc=10:1) to give the title compound. $^1$H NMR (400 MHz, CDCl$_3$) δ 7.88~7.92 (m, 1H), 7.40 (d, J=4.0, 1H), 7.16~7.18 (m, 1H), 6.96~7.01 (m, 2H), 6.32~6.36 (m, 2H), 5.16 (s, 2H), 3.74 (s, 3H), 3.71 (s, 3H). MS m/z (M+H): 461.0

Intermediate 3: 5-chloro-N-(2,4-dimethoxybenzyl)-2,4-difluoro-N-(1,2,4-thiadiazol-5-yl) benzenesulfonamide

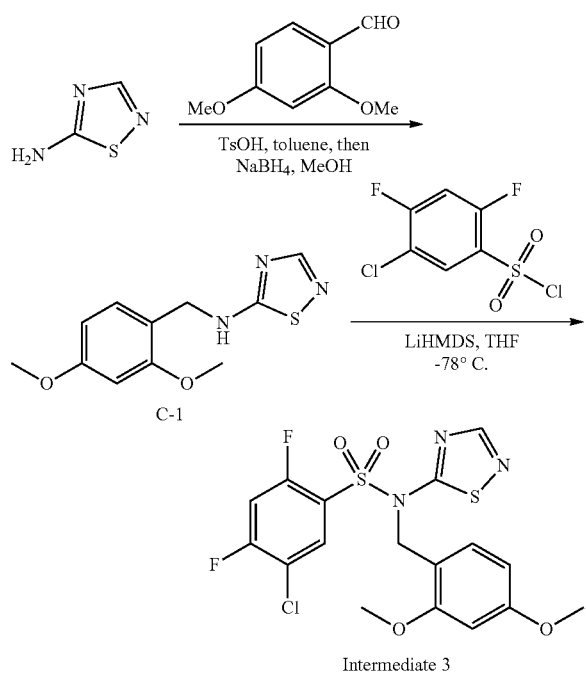

Intermediate 3

Step 1: Preparation of N-(2,4-dimethoxybenzyl)-1,2,4-thiadiazol-5-amine (C-1)

Into a 20000-mL 4-necked round-bottom flask purged and maintained with an inert atmosphere of nitrogen was placed 1,2,4-thiadiazol-5-amine (300 g, 2.97 mol), 2,4-dimethoxybenzaldehyde (472 g, 2.84 mol, 1.05 equiv), p-TsOH (4.1 g, 23.8 mmol, 0.01 equiv), toluene (9 L). The resulting solution was heated to reflux overnight with a water-separator. The reaction mixture was cooled to room temperature and concentrated under vacuum. The residue was washed with methanol. The resulting yellow solid was used crude in the next reaction. Into a 10-L 4-necked round-bottom flask purged and maintained with an inert atmosphere of nitrogen was placed a solution of the crude solid (550 g, 2.21 mol) in THF (5.5 L). This was followed by the addition of NaBH$_4$ (83 g, 2.25 mol) in several batches at 0° C. The resulting solution was stirred for 3 h at room temperature, then extracted with 3×1 L of ethyl acetate. The organic layers were combined, washed with 1×1000 mL of brine, dried over anhydrous magnesium sulfate and concentrated under vacuum. The residue was applied onto a silica gel column and eluted with dichloromethane/methanol (100:1) to give the title compound as a solid.

Step 2: Preparation of 5-chloro-N-(2,4-dimethoxybenzyl)-2,4-difluoro-N-(1,2,4-thiadiazol-5-yl) benzenesulfonamide (Intermediate 3)

To a mixture of C-1 (1.0 g, 4.0 mmol) in THF (20 mL) was added LiHMDS (5 mL, 5 mmol, 1M) at −78° C. under N$_2$. The mixture was warmed to room temperature and stirred for 1 h before cooled to −78° C. Then a solution of 5-chloro-2,4-difluorobenzene-1-sulfonyl chloride (1.2 g, 4.8 mmol) in THF (4 mL) was added dropwise. The mixture was stirred at room temperature for additional 1 h, then quenched with saturated NH$_4$Cl. The mixture was extracted with EtOAc and the combined organic phases were dried with Na$_2$SO$_4$, filtered and concentrated. The residue was purified by column chromatography on silica gel (PE:EtOAc=6:1) to afford the title compound. $^1$H NMR (400 MHz, CDCl$_3$) δ 8.22 (s, 1H), 7.73 (t, J=7.6 Hz, 1H), 7.19 (d, J=8.4 Hz, 1H), 6.87 (t, J=8.4 Hz, 1H), 6.35 (dd, J=2.4, 6.0 Hz, 1H), 6.15 (d, J=2.0 Hz, 1H), 5.36 (s, 2H), 3.74 (s, 3H), 3.66 (s, 3H). MS m/z (M+H): 462.0.

The following cores were made by analogy to Intermediate 1, Intermediate 2 and Intermediate 3 using commercially available sulfonyl chlorides and heterocycloalkyl amines or sulfonyl chlorides and amines in the published literature:

Intermediate 4: N-(2,4-dimethoxybenzyl)-2,4,5-trifluoro-N-(1,2,4-thiadiazol-5-yl) benzenesulfonamide

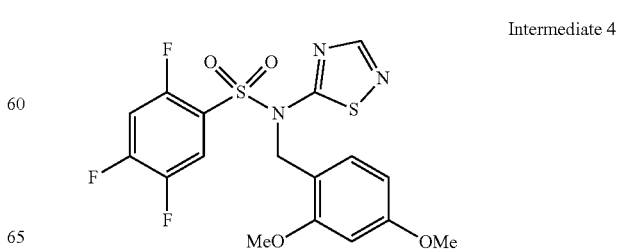

Intermediate 4

¹H NMR (300 MHz, d₆-DMSO) δ 8.47 (1H, s), 7.90-7.80 (2H, m), 7.10-7.08 (1H, d), 6.46-6.41 (1H, d), 6.35-6.34 (1H, d), 5.24 (2H, d), 3.75-3.17 (6H, d).

Intermediate 5: 5-chloro-N-(5-chlorothiazol-2-yl)-N-(2,4-dimethoxybenzyl)-2,4-difluoro benzenesulfonamide

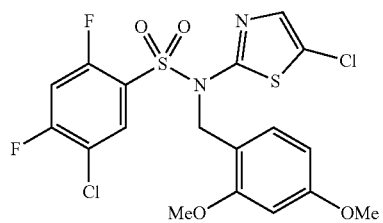

Intermediate 5

¹H NMR (400 MHz, CDCl₃) δ 7.88 (t, J=7.2 Hz, 1H), 7.24 (s, 1H), 7.18 (d, J=8.0 Hz, 1H), 7.00 (t, J=8.8 Hz, 1H), 6.37 (dd, J=8.4, 2.4 Hz, 1H), 6.32 (d, J=2.4 Hz, 1H), 5.12 (s, 2H), 3.77 (s, 3H), 3.73 (s, 3H). MS m/z (M+H): 495.

Intermediate 6: 5-chloro-N-(2,4-dimethoxybenzyl)-2,4-difluoro-N-(5-fluorothiazol-2-yl)benzenesulfonamide

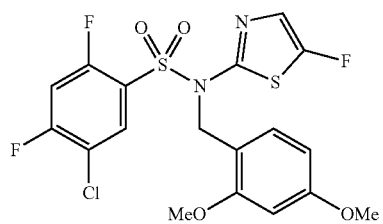

Intermediate 6

¹H NMR (400 MHz, CDCl₃) δ 7.87 (t, J=7.6 Hz, 1H), 7.16 (d, J=8.4 Hz, 1H), 7.01~7.06 (m, 2H), 6.38 (dd, J=8.4, 2.4 Hz, 1H), 6.33 (d, J=2.4 Hz, 1H), 5.04 (s, 2H), 3.77 (s, 3H), 3.72 (s, 3H). MS m/z (M+H): 479.

Intermediate 9: 5-bromo-N-(2,4-dimethoxybenzyl)-2,4-difluoro-N-(thiazol-2-yl)benzenesulfonamide

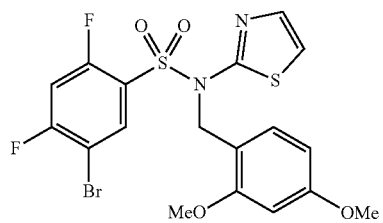

Intermediate 9

¹H NMR (400 MHz, CD₃OD) δ 8.06 (t, J=7.2 Hz, 1H), 7.43 (d, J=3.2 Hz, 1H), 7.20 (d, J=8.4 Hz, 1H), 7.03 (d, J=3.2 Hz, 1H), 6.97 (t, J=8.8 Hz, 1H), 6.38-6.34 (m, 2H), 5.18 (s, 2H), 3.77 (s, 3H), 3.73 (s, 3H). MS m/z (M+H): 505, 507.

Intermediate 10: tert-butyl ((2R,3S)-3-(aminomethyl)-5-methylhexan-2-yl)carbamate

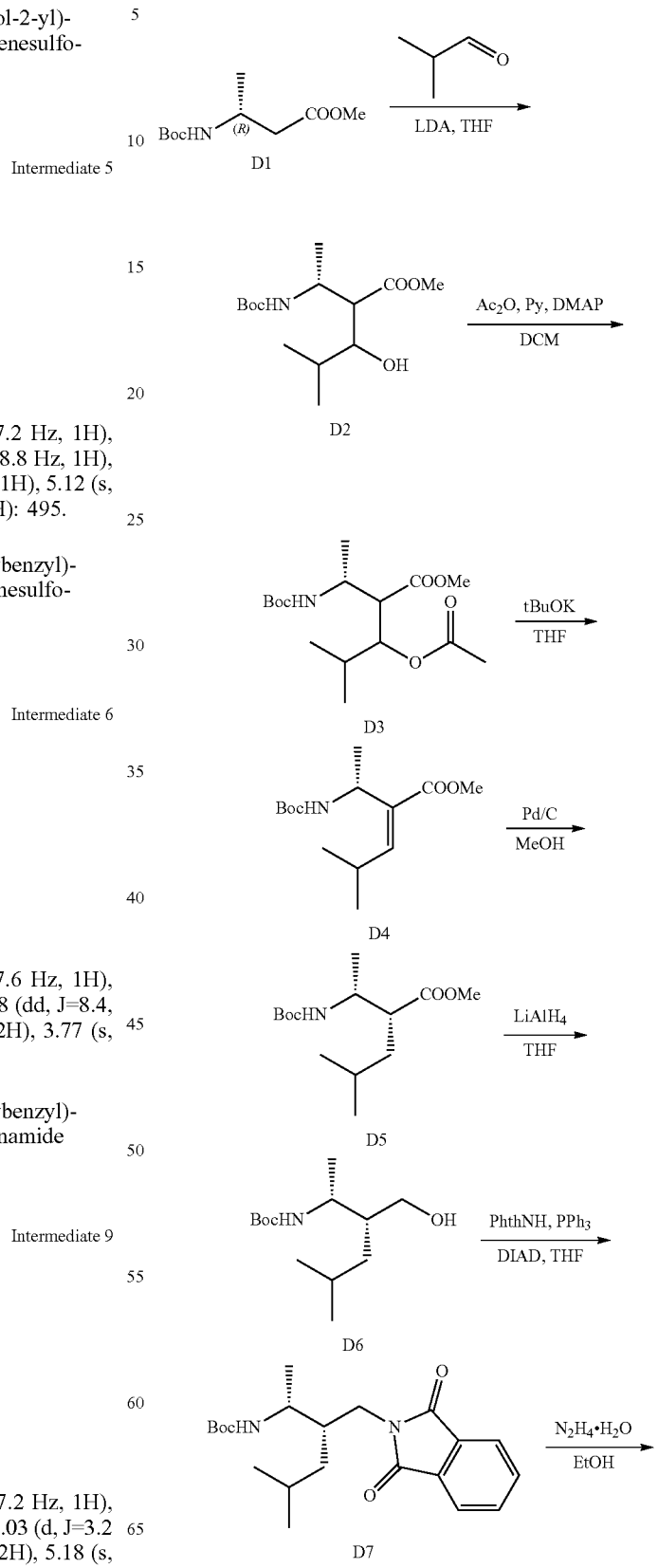

-continued

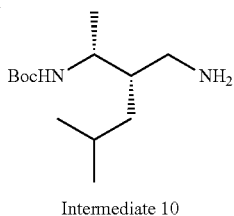

Intermediate 10

Step 1: Preparation of methyl 2-((R)-1-((tert-butoxycarbonyl)amino)ethyl)-3-hydroxy-4-methylpentanoate (D2)

To a solution of LDA (2 M, 810 mL, 1.62 mol) in THF (2.6 L) at −70° C. under an atmosphere of nitrogen was added a solution of D1 (160 g, 736 mmol) in THF (160 mL) in portions for 30 mins at −70° C. After 1 hour, 2-methylpropanal (106 g, 1.47 mol) in THF (90 mL) at −70° C. over 30 mins. After 1 hour, the reaction mixture was poured into a solution of sat. NH$_4$Cl and extracted with EtOAc. The combined organics were washed with brine, dried over Na$_2$SO$_4$, filtered and concentrated to give the title compound. $^1$H NMR: (400 MHz, CDCl$_3$) δ 5.15-5.17 (m, 1H), 4.88 (br. s, 1H), 4.01-4.03 (m, 1H), 3.73 (s, 3H), 3.57-3.58 (m, 1H), 2.65-2.68 (m, 1H), 2.28 (br. s, 1H), 1.67-1.71 (m, 2H), 1.43 (s, 9H), 1.17-1.20 (m, 3H), 0.91-0.92 (m, 6H).

Step 2: Preparation of methyl 3-acetoxy-2-((R)-1-((tert-butoxycarbonyl)amino) ethyl)-4-methylpentanoate (D3)

To a solution of D2 (166 g, 574 mmol) in DCM (1.66 L) at 25° C. was added pyridine (926 mL, 11.5 mol), followed by Ac$_2$O (117 g, 1.15 mol) and DMAP (7.01 g, 57.4 mmol) at 25° C. under an atmosphere of nitrogen. After 2 hours, the reaction mixture was concentrated to give the title compound for use in the next step without purification.

Step 3: Preparation of methyl (R,E)-2-(1-((tert-butoxycarbonyl)amino)ethyl)-4-methyl pent-2-enoate (D4)

To a solution of D3 (200 g, 604 mmol) in THF (3.00 L) at 0° C. under an atmosphere of nitrogen was added t-BuOK (203 g, 1.81 mol) in portions over 30 min. After 2 hours at 0° C., the reaction mixture was poured into sat. NH4Cl and extracted with EtOAc. The combined organics were washed with brine, dried over Na$_2$SO$_4$, filtered and concentrated. The residue was purified by silica gel chromatography (petroleum ether:EtOAc=50:1-20:1-10:1) to give the title compound. $^1$H NMR (400 MHz, CDCl$_3$) δ 6.52 (d, J=10.4 Hz, 1H), 5.60-6.62 (m, 1H), 4.82-4.90 (m, 1H), 3.74 (s, 3H), 2.83-2.92 (m, 1H), 1.41 (s, 9H), 1.31 (d, J=7.2 Hz, 3H), 1.01 (dd, J=6.4 Hz, 16.4 Hz, 6H).

Step 4: Preparation of methyl (R)-2-((R)-1-((tert-butoxycarbonyl)amino)ethyl)-4-methylpentanoate (D5)

To a suspension of Pd/C (7.5 g) in MeOH (1.50 L) at 25° C. was added D4 (37 g, 136 mmol). The suspension was degassed and purged with H$_2$ 3 times then stirred under 50 Psi H$_2$ at 25° C. After 2 hours, the reaction mixture was filtered and the filter cake was washed with MeOH. The organic solution was concentrated and purified by silica gel chromatography (petroleum ether:EtOAc=100:1-50:1) to give the title compound. $^1$H NMR (400 MHz, CDCl$_3$) δ 5.20 (d, J=8.8 Hz, 1H), 3.81 (br. s, 1H), 3.63 (s, 3H), 2.50-2.54 (m, 1H), 1.48-1.53 (m, 2H), 1.40 (s, 9H), 1.28-1.38 (m, 1H), 1.06 (d, J=6.4 Hz, 2H), 0.81-0.84 (m, 6H).

Step 5: Preparation of tert-butyl ((2R,3R)-3-(hydroxymethyl)-5-methylhexan-2-yl) carbamate (D6)

To a solution of D5 (43 g, 157 mmol) in THF (430 mL) at 0° C. under an atmosphere of nitrogen was added LAH (8.95 g, 236 mmol) in portions at 0° C. over 30 mins. After 1 hour, added H$_2$O (9 mL) dropwise at 0° C. over 10 mins, then 15% NaOH aqueous (9 mL) dropwise at 0° C. over 10 mins, then H$_2$O (18 mL) dropwise at 0° C. over 10 mins, and finally Na$_2$SO$_4$ (60 g). After stirring 30 minutes, the suspension was filtered and the filter caker was washed with EtOAc. The filtrate was concentrated to give the title compound that was used in the next step without purification. $^1$H NMR (400 MHz, CDCl$_3$) δ 4.72 (br. s, 1H), 3.64-3.75 (m, 2H), 3.52-3.55 (m, 1H), 2.74 (br. s, 1H), 1.68 (br. s, 1H), 1.45 (s, 9H), 1.32 (br. s, 1H), 1.19 (d, J=6.8 Hz, 2H), 1.07 (br. s, 1H), 0.90 (dd, J=6.8 Hz, 24.8 Hz, 6H).

Step 6: Preparation of tert-butyl ((2R,3S)-3-((1,3-dioxoisoindolin-2-yl)methyl)-5-methylhexan-2-yl) carbamate (D7)

To a solution of D6 (37 g, 151 mmol) in THF (1.48 L) was added isoindoline-1,3-dione (44.4 g, 302 mmol) and PPh$_3$ (79.1 g, 302 mmol) at 25° C. under at atmosphere of nitrogen. The mixture was cooled to 0° C. and DIAD (39.6 g, 196 mmol, 38.1 mL) was added dropwise over 30 mins. After 2 hours, the mixture was concentrated and purified by silica gel chromatography (petroleum ether:EtOAc=50:1-30:1-8:1) to give the title compound. $^1$H NMR (400 MHz, CDCl$_3$) δ 7.82-7.84 (m, 2H), 7.70-7.71 (m, 2H), 4.69 (br. s, 1H), 3.75 (br. s, 1H), 3.48-3.68 (m, 2H), 2.13 (br. s, 1H), 1.72-1.79 (m, 1H), 1.24-1.39 (m, 9H), 1.11-1.16 (m, 5H), 0.86-1.08 (m, 6H).

Step 7: Preparation of tert-butyl ((2R,3S)-3-(aminomethyl)-5-methylhexan-2-yl) carbamate (Intermediate 10)

To a solution of D7 (78 g, 208 mmol) in EtOH (800 mL) at 25° C. was added NH$_2$NH$_2$.H$_2$O (134 g, 2.67 mol, 130 mL) and the mixture was heated to 70° C. After 2 hours, the suspension was cooled to 25° C. and filtered. The filter cake was washed with EtOH, concentrated and purified by silica gel chromatography (petroleum ether:EtOAc=10:1-4:1-2:1) to give the title compound. $^1$H NMR (400 MHz, CDCl$_3$) δ 5.74-5.75 (m, 1H), 3.69-3.76 (m, 2H), 2.84-2.88 (m, 1H), 2.69-2.73 (m, 1H), 1.63-1.70 (m, 1H), 1.63 (s, 9H), 1.60-1.61 (m, 4H), 1.17-1.20 (m, 3H), 0.86-0.90 (m, 6H).

IonWorks® Experimental Procedure

Compounds were tested on human Nav1.7 and Nav1.5 channels stably expressed in HEK 293 cells. Sodium current measurements on IonWorks Quattro: An automated patch-clamp assay on the IonWorks Quattro platform (Molecular Devices) was used to measure state-dependent inhibition of human Nav1.7 and 1.5 channels. Cells were sealed on a planar substrate using the Population Patch Plate (PPC) technology. Electrical access was obtained using both nystatin and amphotericin. A double-pulse protocol was used for the determination of IC$_{50}$ values for inactivated state block. Nav1.7 and Nav1.5 expressing cells were voltage clamped at −100 mV and −110 mV, respectively. A depolarizing prepulse to −10 mV (Nav1.7) or −30 mV (Nav1.5) for 1000 ms followed by a 10 ms repolarization to −100 mV (Nav1.7) or −110 mV (Nav1.5) was given to generate fractional channel inactivation of 50%, followed by a 10 ms test pulse to −10 mV (Nav1.7) or −30 mV (Nav1.5) to measure peak current in control conditions and after compound addition. The following recording solutions were used (mM). External: 150 NaCl, 2 $CaCl_2$, 5 KCl, 1 Mg $Cl_2$, 10 HEPES, 12 Dextrose; internal: 120 CsF, 30 CsCl, 10 EGTA, 5 HEPES, 5 NaF, 2 $MgCl_2$.

For all electrophysiology experiments, offline analysis was used to determine percent inhibition as a function of drug concentration. $IC_{50}$ values were determined by fitting to the Hill equation.

The various compounds presented in the Examples and Tables above were assayed for activity and selectivity using the foregoing IonWorks® technique. The results are reported in the following paragraph in a format expressing the identification of the compound with reference Example and compound (e.g. Ex 1-04 is Example 1, compound 4) followed by the observed potency in nM and the ratio of $Na_v$ 1.7 potency:$Na_v$ 1.5 potency as described here. Thus, Ex1-04: 1.7=9.6/ratio=3440 identifies the compound 4 of Example 1 as having 9.6 nM potency for the Nav 1.7 sodium ion channel (as measured by IonWorks®) and a ratio of 3440 $Na_v$ 1.7 potency:$Na_v$ 1.5 potency, determined by IonWorks® measurement. The following results are reported:

IonWorks® Data

Ex 1-04: 1.7=9.6/ratio >3440; Ex 1-05: 1.7=10/ratio >3300; Ex 1-06: 1.7=15/ratio >2200; Ex 1-07: 1.7=18/ratio >1800; Ex 1-10: 1.7=28/ratio >1180; Ex 1-15: 1.7=29/ratio >1140; Ex 1-27: 1.7=31/ratio >1070; Ex 1-28: 1.7=8.4/ratio >3930; Ex 1-29: 1.7=52/ratio >635; Ex 1-30: 1.7=19/ratio >1740; Ex 4-05 racemic: 1.7=11/ratio >3000; Ex 4-05 Enantiomer B: 1.7=12/ratio >2750; Ex 5-03: 1.7=34/ratio >970; Ex 5-04: 1.7=12/ratio >2750; Ex 7-6: 1.7=34/ratio >970; Ex 7-7: 1.7=80/ratio >410; Ex 7-8: 1.7=10/ratio >3300; Ex 7-9: 1.7=29/ratio >1140; Ex 7-10: 1.7=16/ratio >2060; Ex 7-11: 1.7=9.9/ratio >3300; Ex 8-09: 1.7=18/ratio >1830; Ex 8-10: 1.7=16/ratio >2060; Ex 8-12: 1.7=21/ratio >1570; Ex 12-07: 1.7=6/ratio >5500; Ex 13-02: 1.7=14/ratio >2360; Ex 14-04: 1.7=14/ratio >2360; Ex 15-05: 1.7=12/ratio >2750; Ex 16-01: 1.7=15/ratio >589; Ex 16-04: 1.7=11/ratio >3000; Ex 16-05: 1.7=5/ratio 3400; Ex 16-06: 1.7=8.1/ratio >4070; Ex 16-08: 1.7=15/ratio >2200; Ex 16-09: 1.7=9.2/ratio >3590; Ex 16-12: 1.7=13/ratio >2540; Ex 16-13: 1.7=12/ratio 2538; Ex 16-14: 1.7=39/ratio >846; Ex 16-15: 1.7=5.1/ratio >6470; Ex 16-16: 1.7=8.7/ratio >3800; Ex 16-17: 1.7=8.3/ratio >3980; Ex 16-18: 1.7=18/ratio >1833; Ex 16-19: 1.7=11/ratio >3000; Ex 16-20: 1.7=80/ratio >412; Ex 16-21: 1.7=31/ratio >1046; Ex 16-22: 1.7=38/ratio >868; Ex 16-24: 1.7=21/ratio >1571; Ex 16-25: 1.7=26/ratio >1270; Ex 16-26: 1.7=28/ratio >1180; Ex 16-27: 1.7=19/ratio >1737; Ex 16-28: 1.7=25/ratio >1320; Ex 16-29: 1.7=56/ratio >589; Ex 16-30: 1.7=14/ratio >2357; Ex 16-32: 1.7=49/ratio >673; Ex 16-33: 1.7=12/ratio >2750; Ex 16-34: 1.7=29/ratio >1140; Ex 16-35: 1.7=14/ratio >2360; Ex 16-36: 1.7=15/ratio >2200; Ex 16-37: 1.7=19/ratio >1740; Ex 16-41: 1.7=14/ratio >2360; Ex 16-48: 1.7=8.8/ratio >3750; Ex 16-49: 1.7=14/ratio >2360; Ex 16-50: 1.7=11/ratio >3000; Ex 16-55: 1.7=18/ratio >1833; Ex 16-56: 1.7=12/ratio >2750; Ex 16-57: 1.7=7.5/ratio >4400; Ex 16-58: 1.7=37/ratio >892; Ex 16-59: 1.7=17/ratio >1941; Ex 16-60: 1.7=11/ratio >3000; Ex 16-61: 1.7=21/ratio >1570; Ex 16-62: 1.7=36/ratio >917; Ex 16-63: 1.7=56/ratio >589; Ex 16-64: 1.7=23/ratio >1430; Ex 16-65: 1.7=28/ratio >1180; Ex 16-66: 1.7=16/ratio >2060; Ex 16-67: 1.7=16/ratio >2060; Ex 16-68: 1.7=20/ratio >1650; Ex 16-69: 1.7=18/ratio >1830; Ex 16-70: 1.7=8.5/ratio >2710; Ex 16-71: 1.7=7/ratio >4710; Ex 16-72: 1.7=11/ratio >3000; Ex 16-73: 1.7=19/ratio >1740; Ex 16-74: 1.7=77/ratio >429; Ex 16-75: 1.7=41/ratio >805; Ex 16-76: 1.7=17/ratio >1940; Ex 16-77: 1.7=24/ratio >1380; Ex 16-78: 1.7=12/ratio >2750; Ex 16-79: 1.7=5.4/ratio=4260; Ex 16-80: 1.7=3.1/ratio >10600; Ex 16-81: 1.7=4.9/ratio >6700; Ex 16-82: 1.7=3.3/ratio >10000; Ex 16-83: 1.7=4.7/ratio >7020; Ex 16-84: 1.7=6.1/ratio >5400; Ex 16-85: 1.7=4.5/ratio >7330; Ex 16-86: 1.7=39/ratio >850; Ex 16-88: 1.7=9.6/ratio >3400; Ex 16-89: 1.7=12/ratio >2750; Ex 16-90: 1.7=5.1/ratio >6470; Ex 16-91: 1.7=14/ratio >2360; Ex 16-92: 1.7=3.4/ratio >9700; Ex 16-93: 1.7=41/ratio >800; Ex 16-94: 1.7=7.3/ratio=3150; Ex 16-95: 1.7=35/ratio >940; Ex 16-96: 1.7=15/ratio >2200; Ex 16-97: 1.7=18/ratio >1830; Ex 16-98: 1.7=8.6/ratio >3840; Ex 16-99: 1.7=5.9/ratio=3900; Ex 16-100: 1.7=15/ratio >2200

What is claimed is:

1. A compound of Formula A:

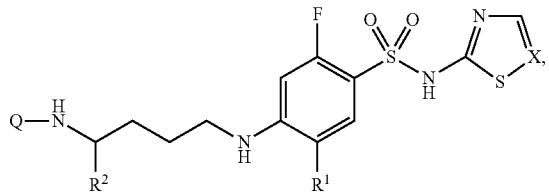

Formula A or a pharmaceutically acceptable salt thereof,
wherein:
$R^1$ is —Cl, —Br, or —F;
$R^2$ is —H or —$CH_3$;
X is:
—N═; or
—C($R^3$)═, wherein $R^3$ is: (i) —H; (ii) —Cl; or (iii) —F; and
Q is:
(a) a moiety of the formula:

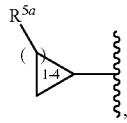

wherein one of $R^{5a}$ is $NH_2$ and the others are —H; or
(b) a moiety of the formula:

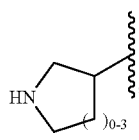

(c) a moiety of the formula:

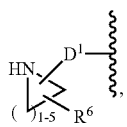

wherein
- $D^1$ is a linear- or branched-alkyl, or a geminal-cycloalkyl moiety of up to 6 carbon atoms; and
- $R^6$ is optionally present as a single substituent and is linear or branched alkyl of up to 4 carbon atoms, which is optionally substituted on one or more carbon atoms thereof with one or more —F; or
- (d) $R^4$—NH-$D^2$-, wherein $R^4$ is —H, lower alkyl, or lower cycloalkyl and $D^2$ is a linear alkyl of at least two up to 6 carbon atoms, a branched-alkyl of up to 6 carbon atoms, or a geminal-cycloalkyl moiety of up to 8 carbon atoms.

2. The compound of claim 1, or a pharmaceutically acceptable salt thereof, wherein X is —CH=.

3. The compound of claim 1, or a pharmaceutically acceptable salt thereof, wherein X is —C(Cl)=.

4. The compound of claim 1, or a pharmaceutically acceptable salt thereof, wherein X is —C(F)=.

5. The compound of claim 1, or a pharmaceutically acceptable salt thereof, wherein X is —N=.

6. The compound of claim 1, or a pharmaceutically acceptable salt thereof, wherein Q is $R^4$—NH-$D^2$-, wherein $R^4$ is —H, lower alkyl, or lower cycloalkyl and $D^2$ is linear- or branched-alkyl, or a geminalcycloalkyl moiety of up to 6 carbon atoms.

7. The compound of claim 6, or a pharmaceutically acceptable salt thereof, wherein $D^2$ is a geminalcycloalky of the formula:

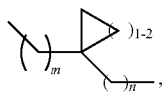

wherein m and n are 0 or 1 and m+n is at least 1.

8. The compound of claim 1, or a pharmaceutically acceptable salt thereof, wherein Q is a moiety of the formula:

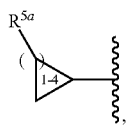

wherein one of $R^{5a}$ is $NH_2$ and the others are —H.

9. The compound of claim 1, or a pharmaceutically acceptable salt thereof, wherein Q is a moiety of the formula:

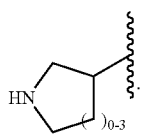

10. The compound of claim 1, or a pharmaceutically acceptable salt thereof, wherein Q is a moiety of the formula:

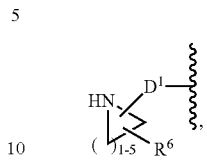

wherein
- $D^1$ is a linear- or branched-alkyl, or a geminal-cycloalkyl moiety of up to 6 carbon atoms; and
- $R^6$ is optionally present as a single substituent and is linear or branched alkyl of up to 4 carbon atoms, which is optionally substituted on one or more carbon atoms thereof with —$CF_3$.

11. The compound of claim 1, or a pharmaceutically acceptable salt thereof, wherein Q is:

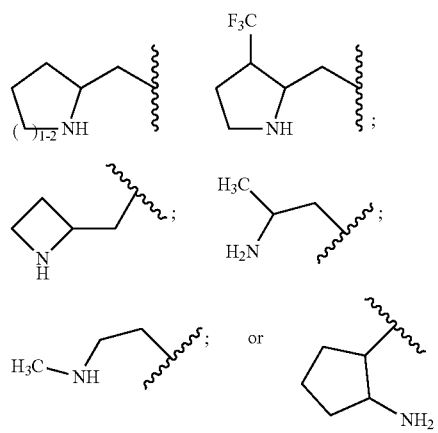

12. A compound, or a pharmaceutically acceptable salt thereof, selected from the group consisting of:

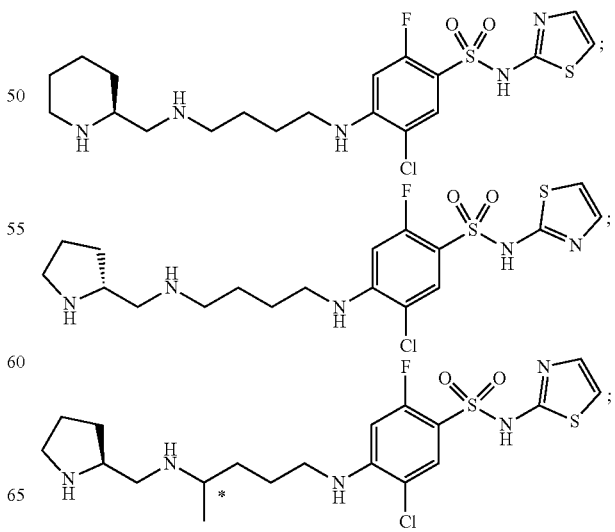

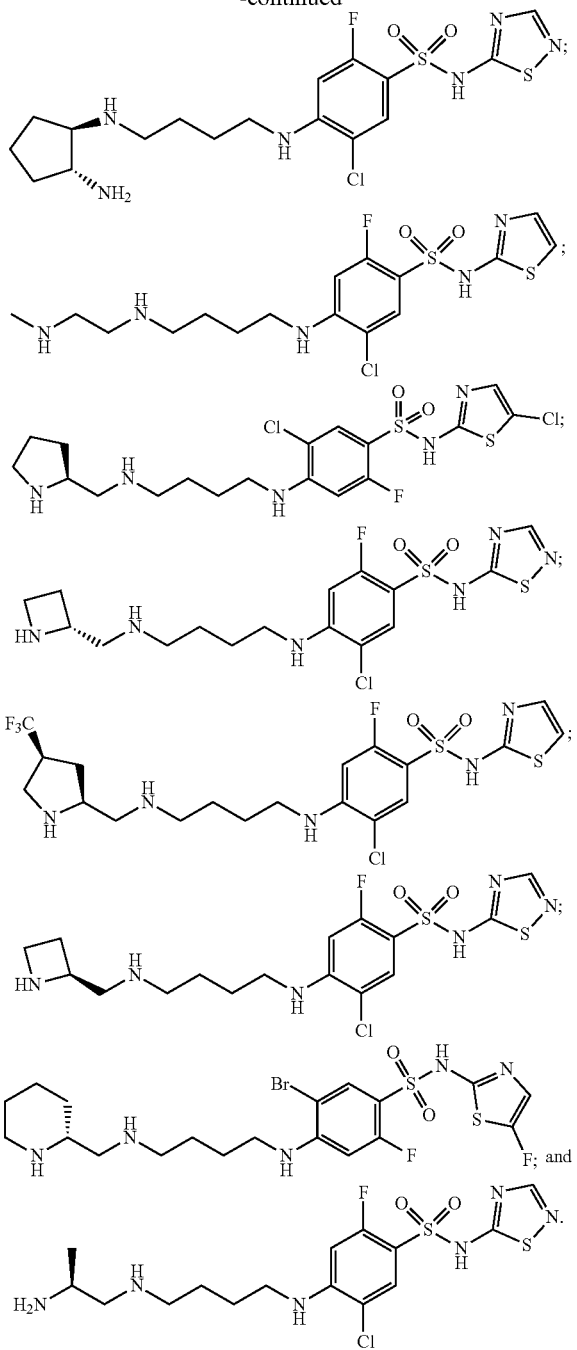

13. A compound which is:

5-chloro-2-fluoro-4-[(4-{[(2S)-piperidin-2-ylmethyl]amino}butyl)amino]-N-1,3-thiazol-2-ylbenzenesulfonamide;

5-chloro-2-fluoro-4-[(4-{[(2R)-piperidin-2-ylmethyl]amino}butyl)amino]-N-1,3-thiazol-2-ylbenzenesulfonamide;

5-chloro-2-fluoro-4-[(4-{[(2S)-pyrrolidin-2-ylmethyl]amino}butyl)amino]-N-1,3-thiazol-2-ylbenzenesulfonamide;

4-[(4-{[(1S,2S)-2-aminocyclohexyl]amino}butyl)amino]-5-chloro-2-fluoro-N-1,3-thiazol-2-ylbenzenesulfonamide;

4-({4-[(2-amino-1,1-dimethylethyl)amino]butyl}amino)-5-chloro-2-fluoro-N-1,3-thiazol-2-ylbenzenesulfonamide;

4-({4-[(2-aminoethyl)(methyl)amino]butyl}amino)-5-chloro-2-fluoro-N-1,3-thiazol-2-ylbenzenesulfonamide;

5-chloro-2-fluoro-4-{[4-({(1S)-1-[(2S)-pyrrolidin-2-yl]ethyl}amino)butyl]amino}-N-1,3-thiazol-2-ylbenzenesulfonamide;

4-[(4-{[(1R,2R)-2-aminocyclohexyl]amino}butyl)amino]-5-chloro-2-fluoro-N-1,3-thiazol-2-ylbenzenesulfonamide;

4-[(4-{[(1S,2R)-2-aminocyclopentyl]amino}butyl)amino]-5-chloro-2-fluoro-N-1,3-thiazol-2-ylbenzenesulfonamide;

4-[(4-{[(1R,2S)-2-aminocyclohexyl]amino}butyl)amino]-5-chloro-2-fluoro-N-1,3-thiazol-2-ylbenzenesulfonamide;

4-({4-[(2-aminoethyl)amino]butyl}amino)-5-chloro-2-fluoro-N-1,3-thiazol-2-ylbenzenesulfonamide;

5-chloro-2-fluoro-4-({4-[(3R)-pyrrolidin-3-ylamino]butyl}amino)-N-1,3-thiazol-2-ylbenzenesulfonamide;

5-chloro-2-fluoro-4-({4-[(3S)-pyrrolidin-3-ylamino]butyl}-amino)-N-1,3-thiazol-2-ylbenzenesulfonamide;

$N^1$-(2-chloro-5-fluoro-4-((thiazol-2-ylmethyl)sulfonyl)phenyl)-$N^4$-((S)-pyrrolidin-2-ylmethyl)pentane-1,4-diamine;

(R) $N^1$-(2-chloro-5-fluoro-4-((thiazol-2-ylmethyl)sulfonyl)phenyl)-$N^4$-((S)-pyrrolidin-2-ylmethyl)pentane-1,4-diamine;

(S) N-(2-chloro-5-fluoro-4-((thiazol-2-ylmethyl)sulfonyl)phenyl)-$N^4$-((S)-pyrrolidin-2-ylmethyl)pentane-1,4-diamine;

4-((4-((azetidin-3-ylmethyl)amino)butyl)amino)-5-chloro-2-fluoro-N-(thiazol-2-yl)benzenesulfonamide;

5-chloro-2-fluoro-4-[(4-{[2-(methylamino)ethyl]amino}butyl)amino]-N-1,3-thiazol-2-ylbenzenesulfonamide;

(R)-5-chloro-2-fluoro-4-((4-((pyrrolidin-2-ylmethyl)amino)butyl)amino)-N-(thiazol-2-yl)benzenesulfonamide;

2,5-difluoro-4-[(4-{[(2S)-pyrrolidin-2-ylmethyl]amino}butyl)amino]-N-1,2,4-thiadiazol-5-ylbenzenesulfonamide;

5-chloro-2-fluoro-4-[(4-{[(2S)-pyrrolidin-2-ylmethyl]amino}butyl)amino]-N-1,2,4-thiadiazol-5-ylbenzenesulfonamide;

5-chloro-N-(5-chloro-1,3-thiazol-2-yl)-2-fluoro-4-[(4-{[(2S)-pyrrolidin-2-ylmethyl]amino}butyl)amino]benzenesulfonamide;

5-bromo-2-fluoro-4-[(4-{[(2S)-pyrrolidin-2-ylmethyl]amino}butyl)amino]-N-1,3-thiazol-2-ylbenzenesulfonamide;

5-chloro-2-fluoro-N-(5-fluoro-1,3-thiazol-2-yl)-4-[(4-{[(2S)-pyrrolidin-2-ylmethyl]amino}butyl)amino]benzenesulfonamide;

5-chloro-2-fluoro-4-{[4-({[(2S,4S)-4-methylpyrrolidin-2-yl]methyl}amino)butyl]amino 1-N-1,3-thiazol-2-ylbenzenesulfonamide;

5-chloro-2-fluoro-4-{[4-(1[(2S,5S)-5-methylpyrrolidin-2-yl]methyl}amino)butyl]amino 1-N-1,3-thiazol-2-ylbenzenesulfonamide;

5-chloro-2-fluoro-N-1,3-thiazol-2-yl-4-{[4-(1[(2S,4S)-4-(trifluoromethyl)pyrrolidin-2-yl]methyl 1 amino)butyl]amino}benzenesulfonamide;

4-[(4-{[(1R,2R)-2-aminocyclo-pentyl]amino}butyl) amino]-5-chloro-2-fluoro-N-1,2,4-thiadiazol-5-yl-benzenesulfonamide;
4-[(4-{[(2R)-azetidin-2-ylmethyl]-amino}butyl)amino]-5-chloro-2-fluoro-N-1,2,4-thiadiazol-5-yl-benzenesulfonamide;
4-[(4-{[(2S)-azetidin-2-ylmethyl]-amino}butyl)amino]-5-chloro-2-fluoro-N-1,2,4-thiadiazol-5-ylbenzene-sulfonamide;
4-[(4-{[(2S)-2-aminopropyl]amino}butyl)amino]-5-chloro-2-fluoro-N-1,2,4-thiadiazol-5-ylbenzenesulfonamide;
4-{[4-(azetidin-3-ylamino)butyl]-amino}-5-chloro-2-fluoro-N-1,2,4-thiadiazol-5-ylbenzenesulfonamide;
5-bromo-2-fluoro-N-(5-fluoro-1,3-thiazol-2-yl)-4-[(4-{[(2R)-piperidin-2-ylmethyl]amino}butyl)amino]benzene-sulfonamide;
4-[(4-{[(1R,2R)-2-aminocyclopentyl]-amino}butyl) amino]-5-chloro-2-fluoro-N-(5-fluoro-1,3-thiazol-2-yl)benzene-sulfonamide;
4-[(4-{[(2R)-2-aminopropyl]amino}-butyl)amino]-5-chloro-2-fluoro-N-(5-fluoro-1,3-thiazol-2-yl)benzenesulfonamide;
4-[(4-{[(1R)-2-amino-1-methylethyl]-amino}butyl) amino]-5-chloro-2-fluoro-N-1,3-thiazol-2-ylbenzenesulfonamide;
4-[(4-{[(1R,2R)-2-aminocyclopentyl]-amino}butyl) amino]-5-chloro-2-fluoro-N-1,3-thiazol-2-ylbenzenesulfonamide;
4-[(4-{[(2S)-2-aminopropyl]-amino}butyl)amino]-5-chloro-2-fluoro-N-1,3-thiazol-2-ylbenzenesulfonamide;
5-chloro-2-fluoro-N-(5-fluoro-1,3-thiazol-2-yl)-4-[(4-[(2R)-pyrrolidin-2-yl-methyl]amino-butyl)-amino] benzenesulfonamide;
5-chloro-2-fluoro-4-{[4-({2-[(2R)-pyrrolidin-2-yl] ethyl}-amino)-butyl]-amino}-N-1,3-thiazol-2-yl-benzenesulfonamide;
5-chloro-2-fluoro-4-[(4-{[(2R)-piperidin-2-yl-methyl] amino}butyl)-amino]-N-1,2,4-thiadiazol-5-yl-benzenesulfonamide;
5-chloro-2-fluoro-N-(5-fluoro-1,3-thiazol-2-yl)-4-[(4-{[(2R)-piperidin-2-yl-methyl]amino}butyl)-amino] benzenesulfonamide;
5-chloro-2-fluoro-4-[(4-{[(2R)-pyrrolidin-2-yl-methyl] amino}butyl)amino]-N-1,2,4-thiadiazol-5-yl-benzenesulfonamide;
5-chloro-2-fluoro-N-(5-fluoro-1,3-thiazol-2-yl)-4-{[4-({2-[(2R)-pyrrolidin-2yl]-ethyl}amino)butyl]-amino}benzenesulfonamide;
5-chloro-2-fluoro-4-({4-[(3R)-pyrrolidin-3-ylamino]-butyl}amino)-N-1,2,4-thiadiazol-5-ylbenzene-sulfonamide;
5-chloro-2-fluoro-4-{[4-({2-[(2R)-pyrrolidin-2-yl] ethyl}-amino)butyl]amino}-N-1,2,4-thiadiazol-5-yl-benzene-sulfonamide;
5-chloro-2-fluoro-4-{[4-({2-[(2S)-pyrrolidin-2-yl]ethyl}-amino)butyl]amino}-N-1,2,4-thiadiazol-5-ylbenzene-sulfonamide;
4-{[4-(azetidin-3-ylamino)-butyl]amino}-5-chloro-2-fluoro-N-(5-fluoro-1,3-thiazol-2-yl)benzene-sulfonamide;
5-chloro-2-fluoro-N-(5-fluoro-1,3-thiazol-2-yl)-4-{[4-({2-[(2S)-pyrrolidin-2-yl]ethyl}amino)butyl] amino}benzenesulfonamide;

4-[(4-{[(1R)-3-amino-1-methylpropyl]amino}butyl) amino]-5-chloro-2-fluoro-N-(5-fluoro-1,3-thiazol-2-yl)-benzenesulfonamide;
4-[(4-{[(1R)-3-amino-1-methylpropyl]amino}butyl) amino]-5-chloro-2-fluoro-N-1,3-thiazol-2-ylbenzenesulfonamide;
4-({4-[(3-amino-1,1-dimethylpropyl)amino] butyl}amino)-5-chloro-2-fluoro-N-(5-fluoro-1,3-thiazol-2-yl)-benzenesulfonamide;
5-chloro-2-fluoro-N-(5-fluoro-1,3-thiazol-2-yl)-4-[(4-{[3-(methylamino)-propyl]amino}butyl)amino]-benzenesulfonamide;
4-[(4-{[(1R)-3-amino-1-methylpropyl]amino}butyl)-amino]-5-chloro-2-fluoro-N-1,2,4-thiadiazol-5-yl-benzenesulfonamide;
4-[(4-{[(3R)-3-amino-butyl]amino}butyl)amino]-5-chloro-2-fluoro-N-(5-fluoro-1,3-thiazol-2-yl)benzenesulfonamide;
4-({4-[(3-aminopropyl)-amino]butyl}amino)-5-chloro-2-fluoro-N-1,2,4-thiadiazol-5-ylbenzene-sulfonamide;
4-({4-[(2-aminoethyl)-amino]butyl}amino)-5-chloro-2-fluoro-N-1,2,4-thiadiazol-5-ylbenzene-sulfonamide;
4-[(4-{[(3R)-3-aminobutyl]-amino}butyl)amino]-5-chloro-2-fluoro-N-1,3-thiazol-2-ylbenzene-sulfonamide;
4-({4-[(3-aminopropyl)amino]-butyl}amino)-5-chloro-2-fluoro-N-(5-fluoro-1,3-thiazol-2-yl)benzene-sulfonamide;
5-bromo-2-fluoro-N-(5-fluoro-1,3-thiazol-2-yl)-4-({4-[(3R)-pyrrolidin-3-yl-amino]butyl}amino)benzene-sulfonamide;
5-bromo-2-fluoro-4-({4-[(3R)-pyrrolidin-3-ylamino]-butyl}amino)-N-1,3-thiazol-2-ylbenzenesulfonamide;
4-{[4-(azepan-3-ylamino)-butyl]amino}-5-chloro-2-fluoro-N-1,3-thiazol-2-yl-benzenesulfonamide;
5-chloro-2-fluoro-4-[(4-{[2-(methylamino)ethyl]amino}-butyl)amino]-N-1,2,4-thiadiazol-5-ylbenzene-sulfonamide;
5-chloro-N-(5-chloro-1,3-thiazol-2-yl)-2-fluoro-4-[(4-{[2-(methylamino)ethyl]-amino}butyl)amino]benzene-sulfonamide;
5-bromo-2-fluoro-4-[(4-{[2-(methylamino)ethyl]amino}-butyl)amino]-N-1,3-thiazol-2-ylbenzenesulfonamide;
5-bromo-2-fluoro-4-[(4-{[3-(methylamino)propyl] amino}butyl)amino]-N-1,3-thiazol-2-ylbenzenesulfonamide;
5-bromo-2-fluoro-N-(5-fluoro-1,3-thiazol-2-yl)-4-[(4-{[3-(methylamino)-propyl]amino}butyl)amino]-benzenesulfonamide;
4-({4-[(2-aminoethyl)-amino]butyl}amino)-5-chloro-2-fluoro-N-(5-fluoro-1,3-thiazol-2-yl)benzene-sulfonamide;
5-chloro-2-fluoro-4-{[4-({3-[(2-fluoroethyl)amino]-propyl}amino)butyl]amino}-N-1,2,4-thiadiazol-5-yl-benzenesulfonamide;
4-[(4-{[(1R)-2-amino-1-methylethyl]amino}butyl)-amino]-5-chloro-2-fluoro-N-(5-fluoro-1,3-thiazol-2-yl)-benzenesulfonamide;
4-[(4-{[(1R)-2-amino-1-methylethyl]amino}butyl)-amino]-5-chloro-2-fluoro-N-1,2,4-thiadiazol-5-yl-benzenesulfonamide;
4-({4-[(2-amino-1,1-dimethylethyl)amino]butyl}amino)-5-chloro-2-fluoro-N-(5-fluoro-1,3-thiazol-2-yl)benzenesulfonamide;
4-[(4-{[1-(aminomethyl)cyclobutyl]amino}butyl) amino]-5-chloro-2-fluoro-N-(5-fluoro-1,3-thiazol-2-yl)benzenesulfonamide;

4-[(4-{[(1-aminocyclopropyl)methyl]amino}butyl)amino]-5-chloro-2-fluoro-N-(5-fluoro-1,3-thiazol-2-yl)benzenesulfonamide;

4-[(4-{[(1R,2S)-2-aminocyclopentyl]amino}butyl)amino]-5-chloro-2-fluoro-N-(5-fluoro-1,3-thiazol-2-yl)benzenesulfonamide;

5-chloro-2-fluoro-N-(5-fluoro-1,3-thiazol-2-yl)-4-[(4-{[(2R)-2-(methylamino)propyl]-amino}butyl)amino]benzenesulfonamide;

4-[(4-{[(1S)-2-amino-1-methylethyl]amino}butyl)amino]-5-chloro-2-fluoro-N-(5-fluoro-1,3-thiazol-2-yl)benzenesulfonamide;

4-[(4-{[(1S)-2-amino-1-methylethyl]amino}butyl)amino]-5-chloro-2-fluoro-N-1,2,4-thiadiazol-5-ylbenzenesulfonamide;

4-[(4-{[(1S)-2-amino-1-methylethyl]amino}butyl)amino]-5-chloro-2-fluoro-N-1,3-thiazol-2-ylbenzenesulfonamide;

4-[(4-{[(1-aminocyclobutyl)methyl]amino}butyl)amino]-5-chloro-2-fluoro-N-(5-fluoro-1,3-thiazol-2-yl)benzenesulfonamide;

4-[(4-{[(1S,2S)-2-aminocyclopentyl]amino}butyl)amino]-5-chloro-2-fluoro-N-1,2,4-thiadiazol-5-ylbenzenesulfonamide;

4-[(4-{[(1S,2S)-2-aminocyclopentyl]amino}butyl)amino]-5-chloro-2-fluoro-N-(5-fluoro-1,3-thiazol-2-yl)benzenesulfonamide;

4-[(4-{[(1S,2S)-2-aminocyclopentyl]amino}butyl)amino]-5-chloro-2-fluoro-N-1,3-thiazol-2-ylbenzenesulfonamide;

4-[(4-{[(2R)-azetidin-2-ylmethyl]amino}butyl)amino]-5-chloro-2-fluoro-N-(5-fluoro-1,3-thiazol-2-yl)benzenesulfonamide;

4-[(4-{[(2S)-azetidin-2-ylmethyl]amino}butyl)amino]-5-chloro-2-fluoro-N-1,3-thiazol-2-ylbenzenesulfonamide;

4-[(4-{[(2R)-azetidin-2-ylmethyl]amino}butyl)amino]-5-chloro-2-fluoro-N-1,3-thiazol-2-ylbenzenesulfonamide;

4-[(4-{[(2S)-azetidin-2-ylmethyl]amino}butyl)amino]-5-bromo-2-fluoro-N-1,2,4-thiadiazol-5-ylbenzenesulfonamide;

4-[(4-{[(2R)-azetidin-2-ylmethyl]amino}butyl)amino]-5-bromo-2-fluoro-N-1,2,4-thiadiazol-5-ylbenzenesulfonamide;

4-[4-[[(1R)-3-amino-1-methyl-propyl]amino]butylamino]-5-bromo-2-fluoro-N-(1,2,4-thiadiazol-5-yl)benzenesulfonamide;

4-[4-[[(2S)-2-aminopropyl]amino]butylamino]-5-bromo-2-fluoro-N-(1,2,4-thiadiazol-5-yl)benzenesulfonamide;

4-[4-[(2-aminocyclobutyl)amino]butylamino]-5-chloro-2-fluoro-N-(1,2,4-thiadiazol-5-yl)benzenesulfonamide;

4-((4-(((1R,2R)-2-aminocyclobutyl)amino)butyl)amino)-5-chloro-2-fluoro-N-(1,2,4-thiadiazol-5-yl)benzenesulfonamide;

4-((4-(((1S,2S)-2-aminocyclobutyl)amino)butyl)amino)-5-chloro-2-fluoro-N-(1,2,4-thiadiazol-5-yl)benzenesulfonamide;

4-((4-(((S)-2-((R)-1-aminoethyl)-4-methylpentyl)amino)butyl)amino)-5-chloro-2-fluoro-N-(5-fluorothiazol-2-yl)benzenesulfonamide;

4-((4-(((S)-2-((R)-1-aminoethyl)-4-methylpentyl)amino)butyl)amino)-5-chloro-2-fluoro-N-(1,2,4-thiadiazol-5-yl)benzenesulfonamide;

4-[4-[[(1R,2R)-2-aminocyclopentyl]amino]butylamino]-2,5-difluoro-N-(1,2,4-thiadiazol-5-yl)benzenesulfonamide;

4-[4-(2-aminoethylamino)butylamino]-5-bromo-2-fluoro-N-(1,2,4-thiadiazol-5-yl)benzenesulfonamide;

4-[4-[(1-aminocyclopropyl)methylamino]butylamino]-5-bromo-2-fluoro-N-(1,2,4-thiadiazol-5-yl)benzenesulfonamide;

5-bromo-2-fluoro-4-[4-[2-(methylamino)ethylamino]butylamino]-N-(1,2,4-thiadiazol-5-yl)benzenesulfonamide;

5-bromo-2-fluoro-4-[4-[3-(methylamino)propylamino]butylamino]-N-(1,2,4-thiadiazol-5-yl)benzenesulfonamide;

5-bromo-4-[4-[2-(ethylamino)ethylamino]butylamino]-2-fluoro-N-(1,2,4-thiadiazol-5-yl)benzenesulfonamide;

4-[4-[[(1S,2R)-2-aminocyclopentyl]amino]butylamino]-5-bromo-2-fluoro-N-(1,2,4-thiadiazol-5-yl)benzenesulfonamide;

4-[4-[[(1R,2R)-2-aminocyclopentyl]amino]butylamino]-5-bromo-2-fluoro-N-(1,2,4-thiadiazol-5-yl)benzenesulfonamide;

4-[4-[[(1S,3S)-3-aminocyclopentyl]amino]butylamino]-5-bromo-2-fluoro-N-(1,2,4-thiadiazol-5-yl)benzenesulfonamide;

5-bromo-2-fluoro-4[4-[(3-methylpyrrolidin-3-yl)amino]butylamino]-N-(1,2,4-thiadiazol-5-yl)benzenesulfonamide;

4-[4-(3-aminopropylamino)butylamino]-5-bromo-2-fluoro-N-(1,2,4-thiadiazol-5-yl)benzenesulfonamide;

4-[4-[[1-(aminomethyl)cyclopropyl]amino]butylamino]-5-bromo-2-fluoro-N-(1,2,4-thiadiazol-5-yl)benzenesulfonamide;

4-[4-[[(2R)-2-aminopropyl]amino]butylamino]-5-bromo-2-fluoro-N-(1,2,4-thiadiazol-5-yl)benzenesulfonamide;

(S)-5-bromo-2-fluoro-4-((4-(pyrrolidin-3-ylamino)butyl)amino)-N-(1,2,4-thiadiazol-5-yl)benzenesulfonamide; or 4-[(4-{[(1R)-2-amino-1-methylethyl]amino}butyl)amino]-5-bromo-2-fluoro-N-1,2,4-thiadiazol-5-ylbenzenesulfonamide, or a pharmaceutically acceptable salt of any thereof.

14. A composition comprising at least one compound of claim 13, or a pharmaceutically acceptable salt thereof, and at least one pharmaceutically acceptable excipient.

15. A The composition of claim 14 comprising additionally an effective amount of at least one other pharmaceutically active ingredient which is: (i) an opioid agonist or antagonist; (ii) a calcium channel antagonist; (iii) an NMDA receptor agonist or antagonist; (iv) a COX-2 selective inhibitor; (v) an NSAID (non-steroidal anti-inflammatory drug); or (vi) paracetamol (APAP), and a pharmaceutically acceptable carrier.

16. A method of treating a pain disorder, or cough, or acute itch or chronic itch disorder comprising administering to a patient in need thereof a therapeutically effective amount of a composition of claim 14.

17. A method of treating pain disorder comprising administering to a patient in need thereof a therapeutically effective amount of a composition of claim 14 wherein the pain disorder is acute pain, perioperative pain or postoperative pain.

18. A composition comprising at least one compound of claim 1, or a pharmaceutically acceptable salt thereof, and at least one pharmaceutically acceptable excipient.

* * * * *